US009768396B2

(12) United States Patent
Inoue et al.

(10) Patent No.: US 9,768,396 B2
(45) Date of Patent: Sep. 19, 2017

(54) IRIDIUM COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Yui Yamada, Kanagawa (JP); Nobuharu Ohsawa, Tochigi (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 608 days.

(21) Appl. No.: 13/722,050

(22) Filed: Dec. 20, 2012

(65) Prior Publication Data

US 2013/0161598 A1 Jun. 27, 2013

(30) Foreign Application Priority Data

Dec. 23, 2011 (JP) ................................. 2011-282431

(51) Int. Cl.
| | | |
|---|---|---|
| H01L 51/54 | (2006.01) | |
| C09K 11/06 | (2006.01) | |
| H01L 51/00 | (2006.01) | |
| C07F 15/00 | (2006.01) | |
| H01L 51/50 | (2006.01) | |

(52) U.S. Cl.
CPC ...... *H01L 51/0085* (2013.01); *C07F 15/0033* (2013.01); *C09K 11/06* (2013.01); *C09K 2211/1044* (2013.01); *C09K 2211/1074* (2013.01); *C09K 2211/185* (2013.01); *H01L 51/0072* (2013.01); *H01L 51/0074* (2013.01); *H01L 51/5016* (2013.01); *H01L 2251/308* (2013.01)

(58) Field of Classification Search
None
See application file for complete search history.

(56) References Cited

U.S. PATENT DOCUMENTS

| | | | |
|---|---|---|---|
| 6,097,147 A | 8/2000 | Baldo et al. | |
| 6,830,828 B2 | 12/2004 | Thompson et al. | |
| 6,902,830 B2 | 6/2005 | Thompson et al. | |
| 7,001,536 B2 | 2/2006 | Thompson et al. | |
| 7,291,406 B2 | 11/2007 | Thompson et al. | |
| 7,537,844 B2 | 5/2009 | Thompson et al. | |
| 7,667,228 B2 | 2/2010 | Okuda et al. | |
| 7,883,787 B2 | 2/2011 | Thompson et al. | |
| 7,993,494 B2 | 8/2011 | Inoue et al. | |
| 8,084,145 B2 | 12/2011 | Inoue et al. | |
| 8,106,390 B2 | 1/2012 | Okuda et al. | |
| 8,164,090 B2 | 4/2012 | Iwasaki et al. | |
| 8,178,874 B2 | 5/2012 | Okuda et al. | |
| 8,980,444 B2 | 3/2015 | Nishiura et al. | |
| 8,986,856 B2 | 3/2015 | Nishiura et al. | |
| 2005/0221123 A1 | 10/2005 | Inoue et al. | |
| 2007/0129545 A1 | 6/2007 | Inoue et al. | |
| 2007/0244320 A1 | 10/2007 | Inoue et al. | |
| 2008/0149923 A1 | 6/2008 | Ohsawa et al. | |
| 2008/0233432 A1 | 9/2008 | Inoue et al. | |
| 2008/0286604 A1 | 11/2008 | Inoue et al. | |
| 2008/0305361 A1 | 12/2008 | Inoue et al. | |
| 2008/0312437 A1 | 12/2008 | Inoue et al. | |
| 2009/0015143 A1 | 1/2009 | Inoue et al. | |
| 2009/0039776 A1 | 2/2009 | Yamada et al. | |
| 2010/0105902 A1 | 4/2010 | Inoue et al. | |
| 2010/0145044 A1 | 6/2010 | Inoue et al. | |
| 2010/0181905 A1 | 7/2010 | Inoue et al. | |
| 2010/0219407 A1 | 9/2010 | Kamatani et al. | |
| 2011/0082296 A1 | 4/2011 | Inoue et al. | |
| 2011/0112296 A1 | 5/2011 | Thompson et al. | |
| 2011/0187265 A1 | 8/2011 | De Cola et al. | |
| 2011/0198988 A1 | 8/2011 | Inoue et al. | |
| 2011/0210316 A1 | 9/2011 | Kadoma et al. | |
| 2011/0220882 A1 | 9/2011 | Inoue et al. | |
| 2011/0245495 A1 | 10/2011 | Inoue et al. | |
| 2011/0309345 A1 | 12/2011 | Balaganesan et al. | |
| 2012/0098417 A1 | 4/2012 | Inoue et al. | |

(Continued)

FOREIGN PATENT DOCUMENTS

| | | |
|---|---|---|
| CN | 102099365 A | 6/2011 |
| EP | 1 647 554 A2 | 4/2006 |

(Continued)

OTHER PUBLICATIONS

Machine translation of JP 2011-253980 (Dec. 15, 2011).*
U.S. Appl. No. 61/619,063, filed Apr. 2, 2012.*
Bredereck, H. et al., Formamide-Reactions, VIII, A New Pyrimidine-Synthesis, Chem. Ber. (Chemische Berichte), vol. 90, 1957, pp. 942-952 (English translation, pp. 1-17).
Kawanishi,Y. et al., "Dependence of Spectroscopic, Electrochemical, and Excited-State Properties of Tris Chelate Ruthenium(II) Complexes on Ligand Structure," Inorganic Chemistry, vol. 28, No. 15, 1989, pp. 2968-2975.

(Continued)

*Primary Examiner* — Marie R. Yamnitzky
(74) *Attorney, Agent, or Firm* — Husch Blackwell LLP

(57) ABSTRACT

A tris-type iridium complex in which a ligand having a distinctive nitrogen-containing five-membered heterocyclic skeleton is coordinated is provided. The ligand has a nitrogen-containing five-membered heterocyclic skeleton composed of 2 to 4 nitrogen atoms and one or more carbon atoms. In the skeleton, an aryl group is bonded to a carbon atom on both sides of which nitrogen atoms are positioned, and a tricycloalkyl group having a bridge structure and having 9 or 10 carbon atoms is bonded to one of the two nitrogen atoms positioned on both the sides of the carbon atom. The tricycloalkyl group having a bridge structure and having 9 or 10 carbon atoms may be an adamantyl group or a noradamantyl group.

18 Claims, 18 Drawing Sheets

(56) References Cited

U.S. PATENT DOCUMENTS

| | | | |
|---|---|---|---|
| 2012/0169219 A1 | 7/2012 | Okuda et al. | |
| 2012/0193613 A1 | 8/2012 | Kadoma et al. | |
| 2012/0197020 A1 | 8/2012 | Osaka et al. | |
| 2012/0205632 A1 | 8/2012 | Shitagaki et al. | |
| 2012/0205687 A1 | 8/2012 | Yamazaki et al. | |
| 2012/0206035 A1 | 8/2012 | Shitagaki et al. | |
| 2012/0217487 A1 | 8/2012 | Yamazaki et al. | |
| 2012/0242219 A1 | 9/2012 | Seo et al. | |
| 2012/0248421 A1 | 10/2012 | Yamazaki et al. | |
| 2012/0256535 A1 | 10/2012 | Seo et al. | |
| 2012/0273769 A1 | 11/2012 | Abe et al. | |
| 2012/0274201 A1 | 11/2012 | Seo et al. | |
| 2013/0099216 A1* | 4/2013 | Ikemizu et al. | 257/40 |
| 2015/0014675 A1* | 1/2015 | Feldman et al. | 257/40 |

FOREIGN PATENT DOCUMENTS

| | | |
|---|---|---|
| EP | 2 336 142 A2 | 6/2011 |
| JP | 2005-255890 | 9/2005 |
| JP | 2006-259112 A | 9/2006 |
| JP | 2007-137872 | 6/2007 |
| JP | 2008-069221 A | 3/2008 |
| JP | 2009-23938 | 2/2009 |
| JP | 2009-40728 | 2/2009 |
| JP | 2009-114137 | 5/2009 |
| JP | 2010-93070 | 4/2010 |
| JP | 2011-121874 A | 6/2011 |
| JP | 2011-121875 A | 6/2011 |
| JP | 2011-121877 A | 6/2011 |
| JP | 2011-190242 A | 9/2011 |
| JP | 2011-213715 A | 10/2011 |
| JP | 2011-219442 A | 11/2011 |
| JP | 2011-528328 | 11/2011 |
| JP | 2011-253980 A | 12/2011 |
| JP | 2012-4526 | 1/2012 |
| JP | 2012-36164 | 2/2012 |
| JP | 2015-519306 | 7/2015 |
| JP | 2015-193644 A | 11/2015 |
| KR | 10-2011-0040941 | 4/2010 |
| WO | WO 00/70655 A2 | 11/2000 |
| WO | WO 2005/007767 A2 | 1/2005 |
| WO | WO 2007/060826 A1 | 5/2007 |
| WO | WO 2009/011447 A2 | 1/2009 |
| WO | WO 2009/060995 A1 | 5/2009 |
| WO | WO 2010/007107 A1 | 1/2010 |
| WO | WO 2011/070989 A1 | 6/2011 |
| WO | WO 2011/070991 A1 | 6/2011 |
| WO | WO 2011/070992 A1 | 6/2011 |
| WO | WO 2011/158544 A1 * | 12/2011 |
| WO | WO 2013/151989 A1 | 10/2013 |

OTHER PUBLICATIONS

Caygill, G.B. et al., "Cyclometallated Compounds IV. Cyclopalladation of Phenylpyrimidines and X-ray Structure of a Doubly Cyclopalladated Derivative of 4,6-Diphenylpyrimidine,", Journal of Organometallic Chemistry, vol. 382, No. 3, Feb. 13, 1990, pp. 455-469.

Berger, R.M. et al., "Unusual Electrochemical and Spectroscopic Behavior in a Ligand-Bridged Binuclear Complex of Ruthenium (II): tetrakis (2,2'-bipyridine)- (μ-2,4,6-tris(2-pyridyl)triazine)diruthenium(II)," Inorganica Chimica Acta, vol. 241, 1996, pp. 1-4.

Inoue, H. et al., "A Reaction of Singlet Oxygen with an Unsaturated Organic Molecule, 6.1.4, Quencher and Photosensitizer," *Basic Chemistry Course Photochemistry I*, Maruzen Co., Ltd., Sep. 30, 1999, pp. 106-110 (with English abstract).

Niu,Y.-H. et al., "Highly Efficient Red Electrophosphorescent Devices Based on an Iridium Complex with Trifluoromethyl-Substituted Pyrimidine Ligand," Applied Physics Letters, vol. 85, No. 9, Aug. 30, 2004, pp. 1619-1621.

Zhang, G-L et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with English translation).

Singh, S.K. et al., "Tuned Helical Array of RhIII/IrIII Cp Complexes with Polypyridyl Ligands," European Journal of Inorganic Chemistry, No. 19, 2006, pp. 3954-3961.

Schwalbe, M. et al., "Ruthenium Polypyridine Complexes of tris-(2-pyridyl)-1,3,5-triazine-Unusual Building Blocks for the Synthesis of Photochemical Molecular Devices," Dalton Transactions, The Royal Society of Chemistry, 2009, pp. 4012-4022.

Chen, Y. et al., "Aggregation-Induced Emission of Ruthenium(II) polypyridyl Complex [Ru(bpy)2(pzta)]2+," Inorganic Chemistry Communications, vol. 13, Oct. 1, 2010, pp. 1140-1143.

Mydlak, M. et al, "Positively Charged Iridium (III) Triazole Derivatives as Blue Emitters for Light-Emitting Electrochemical Cells," Advanced Functional Materials, vol. 20, No. 11, 2010, pp. 1812-1820.

Kozhevnikov, V.N. et al., "Highly Luminescent Mixed-Metal Pt(II)/Ir(III) Complexes: Bis-Cyclometalation of 4,6-Diphenylpyrimidine As a Versatile Route to Rigid Multimetallic Assemblies," Inorganic Chemistry, vol. 50, No. 13, 2011, pp. 6304-6313.

Tonelli, M. et al., "Pharmacophore Modeling, Resistant Mutant Isolation, Docking, and MM-PBSA Analysis: Combined Experimental/Computer-Assisted Approaches to Identify New Inhibitors of the Bovine Viral Diarrhea Virus (BVDV)," Bioorganic & Medicinal Chemistry, Mar. 15, 2010, vol. 18, No. 6, pp. 2304-2316.

STN International HCAPLUS database, CAS Registry Record. (copyright 2016) RN: 120873-41-8, 120873-50-9, 120873-33-8, 120873-59-8, 120873-67-8.

Kevill, D.N. et al., "Synthesis of 5-Substituted 1-(1-adamantyl) Tetrazoles and Related Compounds," Journal of Organic Chemistry, 1970, vol. 35, No. 8, pp. 2526-2529.

* cited by examiner

FIG. 6A
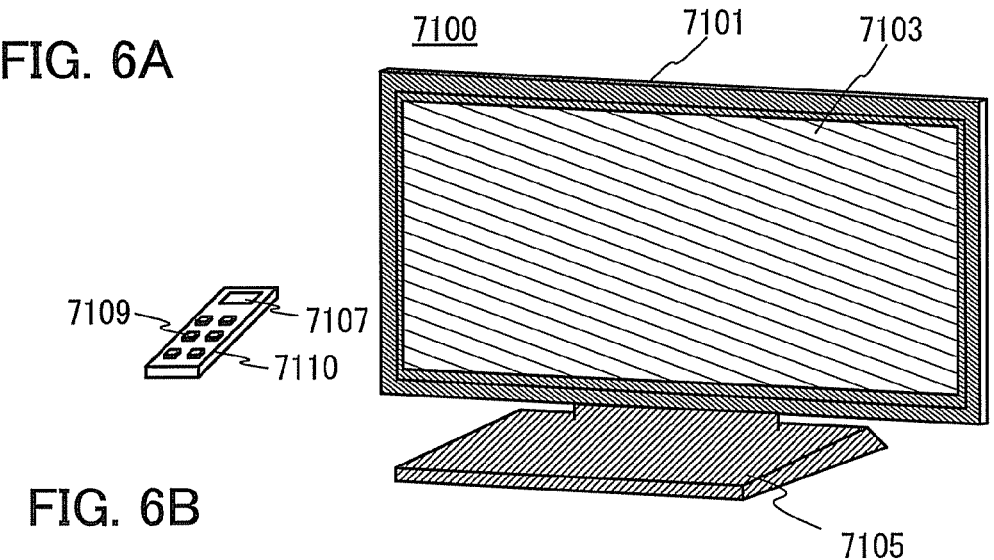
FIG. 6B
FIG. 6C
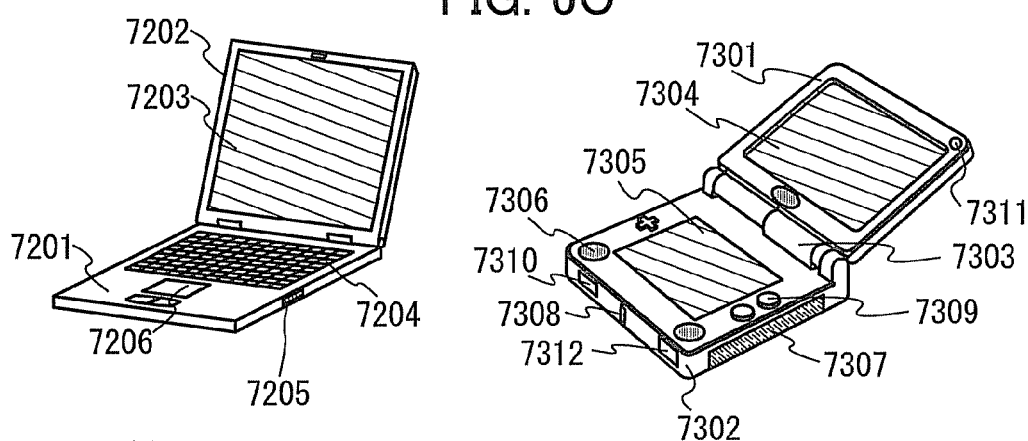
FIG. 6D
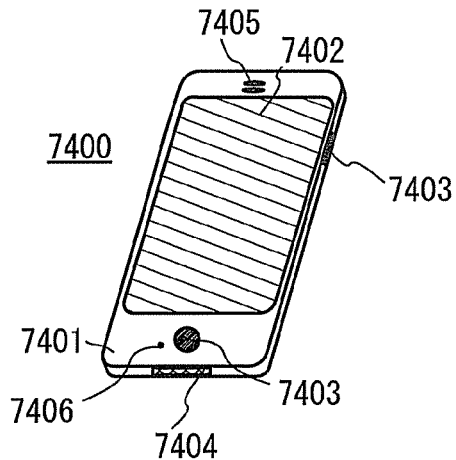

IRIDIUM COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a novel iridium complex that is capable of converting a triplet excited state into luminescence. In addition, the present invention relates to a light-emitting element, a light-emitting device, an electronic device, and a lighting device each using the iridium complex.

2. Description of the Related Art

In recent years, a light-emitting element which uses an organic or inorganic compound having a light-emitting property as a light-emitting material has been actively developed. In particular, a light-emitting element called an EL (electroluminescence) element has attracted attention as a next-generation flat panel display element because it has a simple structure in which a light-emitting layer containing a light-emitting material is provided between electrodes, and characteristics such as feasibility of being thin, lightweight, and highly responsive to input signals, and able to be driven with direct current at a low voltage. In addition, a display using such a light-emitting element has a feature that it is excellent in image quality such as contrast, and has a wide viewing angle. Further, since such a light-emitting element can perform planar light emission, the light-emitting element is considered to be applicable to a light source such as a backlight of a liquid crystal display and lighting.

In an EL element in which an organic compound having a light-emitting property is used as a light-emitting substance, by applying a voltage with a light-emitting layer interposed between electrodes, electrons and holes injected from the electrodes recombine to put the light-emitting substance into an excited state, and light is emitted when the light-emitting substance returns to a ground state from the excited state. The excited states of the light-emitting substance may be a singlet excited state (S*) and a triplet excited state (T*), and the statistical generation ratio thereof in the element is considered to be S*:T*=1:3.

In general, the ground state of an organic compound having a light-emitting property is a singlet state. Therefore, in light emission from a singlet excited state (S*), which is called fluorescence, electron transition occurs between the same spin multiplicities. In contrast, in light emission from a triplet excited state (T*), which is called phosphorescence, electron transition occurs between different spin multiplicities.

In an organic compound having a light-emitting property and emitting fluorescence (hereinafter referred to as fluorescent compound), in general, phosphorescence is not observed at room temperature, and only fluorescence is observed. Accordingly, the internal quantum efficiency in a light-emitting element using a fluorescent compound is presumed to have a theoretical limit of 25% based on S*:T*=1:3 unless a special measure (e.g., utilization of thermally activated delayed fluorescence) is taken.

In contrast, internal quantum efficiency in a light-emitting element using an organic compound having a light-emitting property and emitting phosphorescence (hereinafter referred to as phosphorescent compound) can be 100% in theory when light emission led from intersystem crossing from S* to T* is taken into account. For this reason, the light-emitting element using a phosphorescent compound has been actively developed in order to achieve a highly efficient light-emitting element.

As a phosphorescent compound, an organometallic complex having iridium or the like as a central metal has attracted attention. Development has enabled phosphorescent compounds to emit light with various wavelengths from red to blue; however, for phosphorescence, i.e., light emission from a triplet excited state which is at a lower energy level than a singlet excited state, an organometallic complex having a wider energy gap is necessary for obtaining green to blue light emission with short wavelengths. Such substances are difficult to develop and the number thereof is still limited.

Patent Document 1 discloses an iridium complex in which an imidazole derivative is a ligand.

REFERENCE

Patent Document

[Patent Document 1] PCT International Publication No. 2005/007767

SUMMARY OF THE INVENTION

Iridium complexes which include a ligand having a nitrogen-containing five-membered heterocyclic skeleton such as an imidazole derivative and a triazole derivative readily emit short-wavelength phosphorescence, and thus have attracted attention in development of blue phosphorescent materials.

As cyclometallated iridium complexes, bis-type complexes in which two identical ligands are coordinated and tris-type complexes in which three identical ligands are coordinated are well known. An iridium complex disclosed in the above patent document as an example, in which an imidazole derivative is a ligand, is what is called a bis-type complex in which two imidazole derivatives and the other ligand are coordinated to iridium.

In general, a complex formation reaction for a bis-type complex proceeds via a chlorine-bridged Binuclear complex. Because the reaction is conducted under relatively mild conditions, problems such as decomposition of a complex or a ligand during reaction are not readily caused.

However, in the case of an iridium complex which is a tris-type complex and includes a ligand having a nitrogen-containing five-membered heterocyclic skeleton, in its synthesis process, depending on the structure of the ligand, the ligand may be decomposed to make formation of the objective complex extremely difficult.

In view of the above, an object of one embodiment of the present invention is to provide a novel iridium complex capable of emitting short-wavelength phosphorescence (phosphorescence with a wavelength shorter than that of green light). Specifically, an object of one embodiment of the present invention is to provide a novel iridium complex capable of emitting short-wavelength phosphorescence by having a tris-type structure which includes a ligand having a nitrogen-containing five-membered heterocyclic skeleton.

Another object of one embodiment of the present invention is to provide a light-emitting element which efficiently emits light in the green to blue wavelength region by using such an iridium complex. A further object of one embodiment of the present invention is to provide a light-emitting device, an electronic device, and a lighting device with reduced power consumption or improved light-emitting quality by using the light-emitting element.

The present inventors have successfully synthesized a tris-type iridium complex in which a ligand having a distinctive nitrogen-containing five-membered heterocyclic skeleton is coordinated. The ligand has a nitrogen-containing five-membered heterocyclic skeleton composed of 2 to 4 nitrogen atoms and one or more carbon atoms. In the skeleton, an aryl group is bonded to a carbon atom on both sides of which nitrogen atoms are positioned, and a tricycloalkyl group having a bridge structure and having 9 or 10 carbon atoms is bonded to one of the two nitrogen atoms positioned on both the sides of the carbon atom. Further, in this ligand, the other of the two nitrogen atoms positioned on both the sides of the carbon atom to which the aryl group is bonded (i.e., the nitrogen atom to which the tricycloalkyl group is not bonded) is coordinated to iridium, and one of carbon atoms of the aryl group is bonded to the iridium; thus, a complex is formed. An iridium complex that is one embodiment of the present invention is a tris-type complex in which three ligands having the above structure are coordinated to iridium.

A tris-type iridium complex in which a ligand having a nitrogen-containing five-membered heterocyclic skeleton is coordinated is difficult to synthesize depending on its structure, and a complex is not readily obtained; however, by using a ligand which has the above structure, a tris-type complex in which a ligand having a nitrogen-containing five-membered heterocyclic skeleton is coordinated can be obtained.

In addition, the present inventors have found that this iridium complex emits green to blue phosphorescence with a short wavelength. Specifically, what is characteristic of phosphorescence of this iridium complex is that its emission spectrum extends to a relatively short wavelength region of 450 nm or less. This characteristic spectrum is derived from the above-described structure (a structure which has a nitrogen-containing five-membered heterocyclic skeleton composed of 2 to 4 nitrogen atoms and one or more carbon atoms; in the skeleton, an aryl group is bonded to a carbon atom on both sides of which nitrogen atoms are positioned, and a tricycloalkyl group, having a bridge structure and having 9 or 10 carbon atoms is bonded to one of the two nitrogen atoms positioned on both the sides of the carbon atom; the other nitrogen atom (i.e., the nitrogen atom to which the tricycloalkyl group is not bonded) is coordinated to iridium; and one of carbon atoms of the aryl group is bonded to the iridium); therefore, a light-emitting material having the above structure and emitting light originating from the above structure is one embodiment of the present invention.

Further, the present inventors have found that a light-emitting element including the above-described iridium complex between a pair of electrodes emits light in the green to blue wavelength region with high efficiency by application of a voltage. Since the characteristics of this light-emitting element are derived from the above structure, a light-emitting element which includes a light-emitting material having the above structure and emitting light originating from the above structure, specifically a light-emitting element which includes the light-emitting material as a light-emitting substance, is one embodiment of the present invention.

One embodiment of the present invention is an iridium complex represented by General Formula (G1).

[Chemical formula 1]

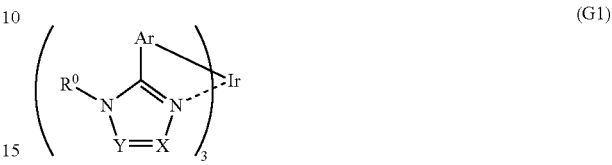

(G1)

In General Formula (G1), Ar represents a substituted or unsubstituted arylene group having 6 to 12 carbon atoms, and $R^0$ represents a tricycloalkyl group having a bridge structure and having 9 or 10 carbon atoms. X and Y separately represent carbon or nitrogen. When X or Y represents carbon, the carbon may have a substituent. When both X and Y represent carbon atoms, the substituents may be bonded to each other (may share a divalent substituent) to form a ring, and the ring may form a fused structure. Note that Y preferably represents carbon, in which case the lifetime of a light-emitting element which uses the iridium complex as a light-emitting substance is likely to be long.

Thus, another embodiment of the present invention is an iridium complex represented by General Formula (G2).

[Chemical formula 2]

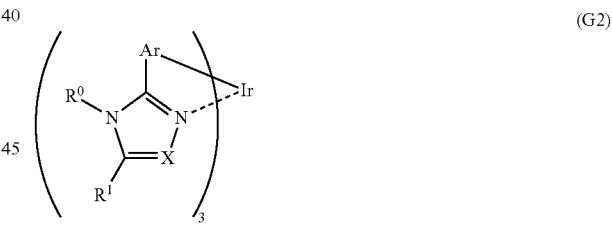

(G2)

In General Formula (G2), Ar represents a substituted or unsubstituted arylene group having 6 to 12 carbon atoms. $R^0$ represents a tricycloalkyl group having a bridge structure and having 9 or 10 carbon atoms, and $R^1$ represents any one of hydrogen, an alkyl group having 1 to 6 carbon atoms, and a phenyl group. X represents carbon or nitrogen. When X represents carbon, the carbon may have a substituent. $R^1$ and X may be bonded to form a ring, and the ring may form a fused structure.

The iridium complex represented by General Formula (G2) has the advantage of emitting phosphorescence with a shorter wavelength in the case where Ar represents an o-phenylene group.

Thus, a further embodiment of the present invention is an iridium complex represented by General Formula (G3).

[Chemical formula 3]

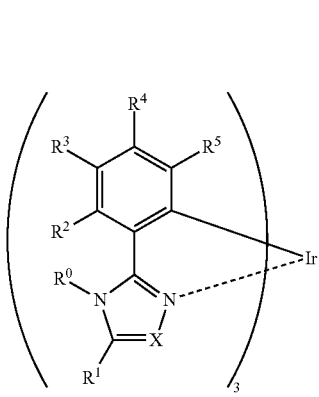

(G3)

In General Formula (G3), R⁰ represents a tricycloalkyl group having a bridge structure and having 9 or 10 carbon atoms, and $R^1$ to $R^5$ separately represent any one of hydrogen, an alkyl group having 1 to 6 carbon atoms, and a phenyl group.

The iridium complex represented by General Formula (G3) has the advantage of emitting phosphorescence with a shorter wavelength in the case where X represents nitrogen. Thus, a still further embodiment of the present invention is an iridium complex represented by General Formula (G4).

[Chemical formula 4]

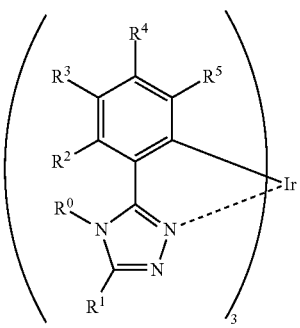

(G4)

In General Formula (G4), R⁰ represents a tricycloalkyl group having a bridge structure and having 9 or 10 carbon atoms, and $R^1$ to $R^5$ separately represent any one of hydrogen, an allyl group having 1 to 6 carbon atoms, and a phenyl group.

The iridium complex represented by General Formula (G4) has the advantage of allowing a light-emitting element to have high emission efficiency in the case where X represents carbon. Thus, a yet still further embodiment of the present invention is an iridium complex represented by General Formula (G5).

[Chemical formula 5]

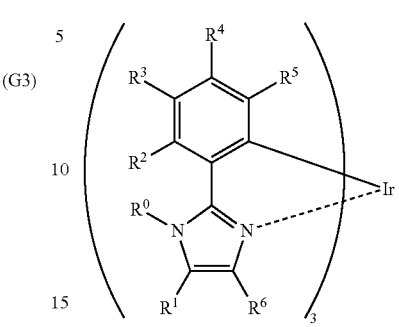

(G5)

In General Formula (G5), R⁰ represents a tricycloalkyl group having a bridge structure and having 9 or 10 carbon atoms, and $R^1$ to $R^6$ separately represent any one of hydrogen, an alkyl group having 1 to 6 carbon atoms, and a phenyl group.

A yet still further embodiment of the present invention is an iridium complex represented by General Formula (G6).

[Chemical formula 6]

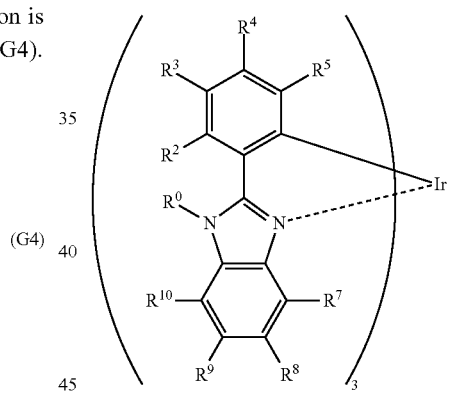

(G6)

In General Formula (G6), R⁰ represents a tricycloalkyl group having a bridge structure and having 9 or 10 carbon atoms, and $R^2$ to $R^5$ and $R^7$ to $R^{10}$ separately represent any one of hydrogen, an allyl group having 1 to 6 carbon atoms, and a phenyl group.

In the iridium complex having any of the above structures, the tricycloalkyl group having a bridge structure and having 9 or 10 carbon atoms can be an adamantyl group or a noradamantyl group; an adamantyl group is particularly preferable for its high availability. As an adamantyl group, there are a 1-adamantyl group and a 2-adamantyl group; a 2-adamantyl group is preferable in view of quantum efficiency, color purity, and sublimation temperatures.

Yet still further embodiments of the present invention are iridium complexes represented by the following general formulae.

[Chemical formula 7]

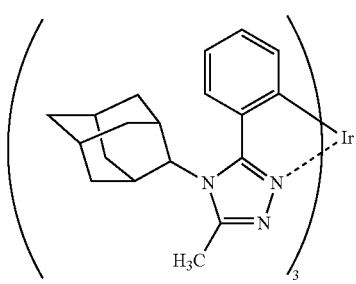
(100)

[Chemical formula 8]

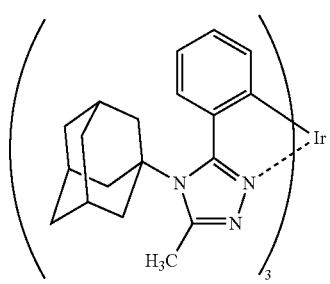
(101)

[Chemical formula 9]

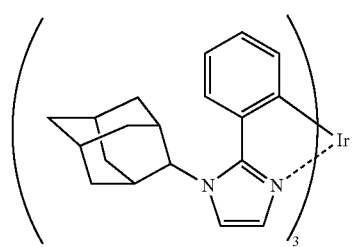
(118)

[Chemical formula 10]

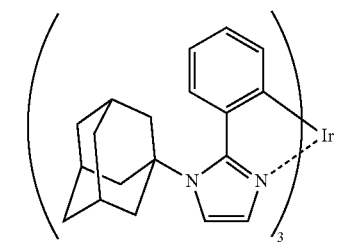
(119)

[Chemical formula 11]

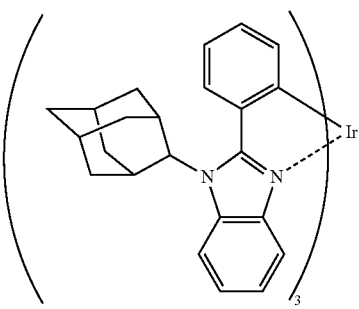
(136)

-continued

[Chemical formula 12]

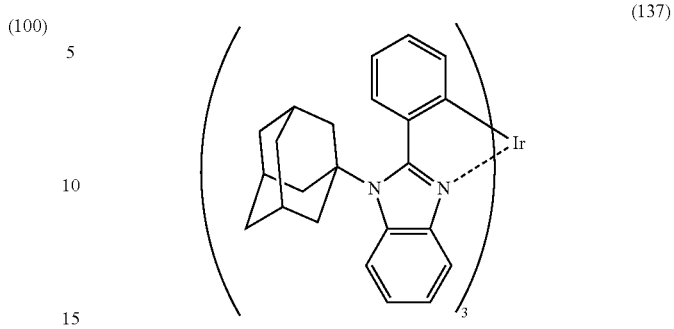
(137)

A yet still further embodiment of the present invention is a light-emitting element including, between a pair of electrodes, any of the iridium complexes described above. In particular, any of the iridium complexes described above is preferably contained in a light-emitting layer.

A light-emitting device, an electronic device, and a lighting device each using the above light-emitting element also belong to the category of the present invention. Note that the light-emitting device in this specification includes, in its category, an image display device, a light-emitting device, and a light source. In addition, the light-emitting device includes, in its category, all of a module in which a connector such as a flexible printed circuit (FPC), a tape automated bonding (TAB) tape or a tape carrier package (TCP) is connected to a panel, a module in which a printed wiring board is provided on the tip of a TAB tape or a TCP, and a module in which an integrated circuit (IC) is directly mounted on a light-emitting element by a chip on glass (COG) method.

An iridium complex having the above structure is a novel iridium complex capable of emitting phosphorescence. The iridium complex is capable of emitting short-wavelength phosphorescence by having a tris-type structure which includes a ligand having a nitrogen-containing five-membered heterocyclic skeleton.

According to one embodiment of the present invention, a light-emitting element which can be fabricated at low cost and which emits light in the wavelength region of blue-green to blue with high efficiency can be provided. In addition, an inexpensive light-emitting device, an inexpensive electronic device, and an inexpensive lighting device each using the light-emitting element can be provided.

According to one embodiment of the present invention, a light-emitting element using the iridium complex, and a light-emitting device, an electronic device, and a lighting device each using the light-emitting element can be provided.

BRIEF DESCRIPTION OF THE DRAWINGS

FIGS. 6A to 6D each illustrate an example of an electronic device.

DETAILED DESCRIPTION OF THE INVENTION

Figure 1:
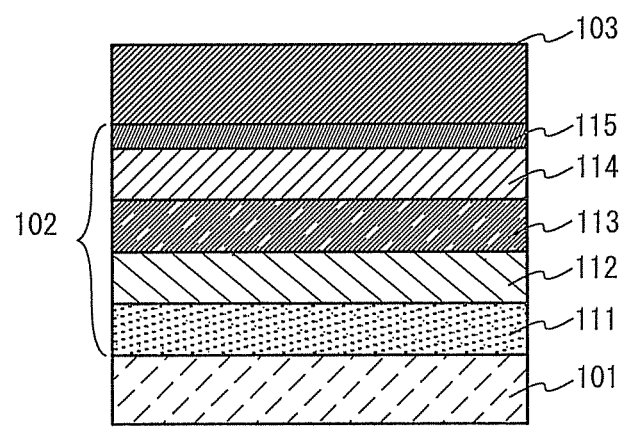
FIG. 1 illustrates an example of a light-emitting element.

Embodiments will now be described with reference to drawings in detail. Note that the invention is not limited to the following description, and it will be easily understood by those skilled in the art that various changes and modifications can be made without departing from the spirit and scope of the invention. Therefore, the invention should not be construed as being limited to the description in the following embodiments. Note that in the structures of the invention described below, the same portions or portions having similar functions are denoted by the same reference numerals in different drawings, and description of such portions is not repeated.

(Embodiment 1)

In this embodiment, an iridium complex of one embodiment of the present invention will be described.

The iridium complex in this embodiment is a tris-type iridium complex in which a ligand having a distinctive structure with a nitrogen-containing five-membered heterocyclic skeleton is coordinated. The ligand has a nitrogen-containing five-membered heterocyclic skeleton composed of 2 to 4 nitrogen atoms and one or more carbon atoms. In the skeleton, an aryl group is bonded to a carbon atom on both sides of which nitrogen atoms are positioned, and a tricycloalkyl group having a bridge structure and having 9 or 10 carbon atoms is bonded to one of the nitrogen atoms positioned on both the sides of the carbon atom to which the aryl group is bonded. Further, in this ligand, the other of the two nitrogen atoms positioned on both the sides of the carbon atom to which the aryl group is bonded (i.e., the nitrogen atom to which the tricycloalkyl group is not bonded) is coordinated to iridium, and one of carbon atoms of the aryl group is bonded to the iridium; thus, a complex is formed. The iridium complex in this embodiment is a tris-type complex in which three ligands having the above structure are coordinated to iridium.

A tris-type iridium complex in which a ligand having a nitrogen-containing five-membered heterocyclic skeleton is coordinated is difficult to synthesize depending on its structure, and a complex is not readily obtained. For example, if a tricycloalkyl group in the ligand of the iridium complex having the above structure is a methyl group, the ligand is likely to be decomposed in a complex formation reaction between the iridium and the ligand, which, leads to an extremely low yield of the complex. In contrast, decomposition of the ligand of the iridium complex having the aforementioned structure is suppressed in a complex formation reaction, so that a complex can be obtained. In addition, as compared to an iridium complex which includes an aryl group such as a phenyl group instead of the tricycloalkyl group in the aforementioned structure, conjugation is less extended in the iridium complex in this embodiment, which allows emission of phosphorescence with a shorter wavelength.

As already stated, an iridium complex having the above structure emits green to blue phosphorescence with a short wavelength. Such a substance which emits phosphorescence in a short wavelength region is very rare. Further, what is characteristic of an iridium complex having the above structure is that the tail of its emission spectrum on a short wavelength side extends to a relatively short wavelength region of 450 nm or less. Although the wavelength of phosphorescence to be emitted by a substance that emits phosphorescence in a short wavelength region is relatively easily extended by devising a molecular structure of the substance, it is extremely difficult to reduce the wavelength. Also in view of this point, the iridium complex in this embodiment, whose emission spectrum extends from the short wavelength region, is valuable.

As the nitrogen-containing five-membered heterocyclic skeleton of the ligand of the iridium complex, an imidazole skeleton, a 1,2,4-triazole skeleton, or a tetrazole skeleton can be used. The aryl group bonded to the carbon atom on both the sides of which the nitrogen atoms are positioned is an aryl group having 6 to 12 carbon atoms. Specifically, a phenyl group, a biphenyl group, a naphthyl group, and the like can be given. Any of such aryl groups can have, as a substituent, an aryl group having 1 to 6 carbon atoms. Further, when carbon other than the carbon atom to which the aryl group is bonded exists in the nitrogen-containing five-membered heterocyclic skeleton, the carbon may have a substituent. When the nitrogen-containing five-membered heterocyclic skeleton is an imidazole skeleton, substituents of adjacent carbon atoms may be bonded to form a ring. Moreover, the ring may form a fused structure to form a benzimidazole skeleton.

Specific examples of the tricycloalkyl group having a bridge structure and having 9 or 10 carbon atoms in the ligand of the iridium complex include an adamantyl group and a noradamantyl group. Between them, an adamantyl group is preferably selected for its stability and high availability. Note that as an adamantyl group, there are a 1-adamantyl group and a 2-adamantyl group which are different in a bonding position; a 2-adamantyl group is preferably introduced in the complex because in that case, light emitted from the complex can have higher quantum yield and phosphorescence with a high color purity whose spectrum is sharp can be obtained.

More specifically, an iridium complex having the above structure according to this embodiment is represented by General Formula (G1) below.

[Chemical formula 13]

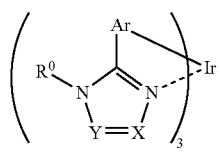

(G1)

In General Formula (G1), Ar represents an arylene group having 6 to 12 carbon atoms. Specific examples of the arylene group include a phenylene group, a biphenyldiol group, and a naphthyl group. Any of such arylene groups can have, as a substituent, an alkyl group having 1 to 6 carbon atoms. Specific examples of an alkyl group having 1 to 6 carbon atoms include a methyl group, an ethyl group, a propyl group, an isopropyl group, a butyl group, a sec-butyl group, an isobutyl group, a tert-butyl group, a pentyl group, a hexyl group, and a cyclohexyl group.

In General Formula (G1), $R^0$ represents a tricycloalkyl group having a bridge structure and having 9 or 10 carbon atoms. As specific examples, an adamantyl group and a noradamantyl group can be given. An adamantyl group is preferably selected for its stability and high availability. As an adamantyl group, there are a 1-adamantyl group and a 2-adamantyl group which are different in a bonding position; a 2-adamantyl group is preferably introduced in the complex because in that case, light emitted from the complex can have higher quantum yield and phosphorescence with a high color purity whose spectrum is sharp can be obtained.

In the formula, X and Y separately represent carbon or nitrogen. When one or both of X and Y represent carbon, the carbon may have a substituent. As the substituent, an alkyl group having 1 to 6 carbon atoms or a phenyl group can be used. When both X and Y represent carbon atoms, the substituents may be bonded to each other (i.e., X and Y may share divalent substituents) to form a ring. Further, when both X and Y represent carbon atoms, these carbon atoms may be fused to a benzene ring. Specific examples of an alkyl group having 1 to 6 carbon atoms include a methyl group, an ethyl group, a propyl group, an isopropyl group, a butyl group, a sec-butyl group, an isobutyl group, a tert-butyl group, a pentyl group, a hexyl group, and a cyclohexyl group.

Note that Y in the iridium complex preferably represents carbon, in which case the lifetime of a light-emitting element which uses the iridium complex as a light-emitting substance is likely to be long. In other words, the iridium complex represented by General Formula (G2) is preferable.

[Chemical formula 14]

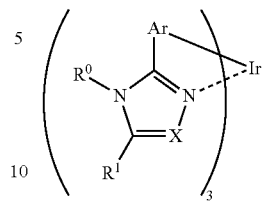

(G2)

In the iridium complex represented by General Formula (G2), Ar and $R^0$ are similar to those in General Formula (G1). X represents carbon or nitrogen. When X represents carbon, the carbon may have a substituent. As the substituent, an alkyl group having 1 to 6 carbon atoms or a phenyl group can be used. Further, $R^1$ represents an alkyl group having 1 to 6 carbon atoms or a phenyl group, and the phenyl group may have, as a substituent, an alkyl group having 1 to 6 carbon atoms. $R^1$ and X may be bonded to form a ring. Further, they may be fused to a benzene ring. Specific examples of an alkyl group having 1 to 6 carbon atoms include a methyl group, an ethyl group, a propyl group, an isopropyl group, a butyl group, a sec-butyl group, an isobutyl group, a tert-butyl group, a pentyl group, a hexyl group, and a cyclohexyl group.

Conjugation is less extended in the iridium complex represented by General Formula (G2) in the case where Ar represents an o-phenylene group, so that the iridium complex has the advantage of emitting phosphorescence with a shorter wavelength. In other words, the iridium complex represented by General Formula (G3) is preferable.

[Chemical formula 15]

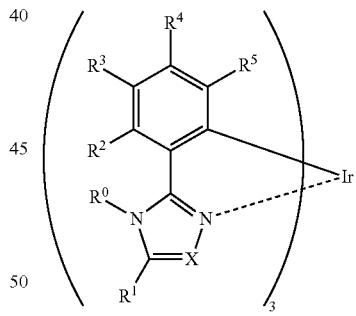

(G3)

In the iridium complex represented by General Formula (G3), $R^0$, $R^1$, and X are similar to those in General Formula (G2). $R^2$ to $R^5$ separately represent any one of hydrogen, an alkyl group having 1 to 6 carbon atoms, and a phenyl group. Specific examples of an alkyl group having 1 to 6 carbon atoms include a methyl group, an ethyl group, a propyl group, an isopropyl group, a butyl group, a sec-butyl group, an isobutyl group, a tert-butyl group, a pentyl group, a hexyl group, and a cyclohexyl group.

The iridium complex represented by General Formula (G3) has the advantage of emitting phosphorescence with a shorter wavelength in the case where X represents nitrogen. This iridium complex is an iridium complex represented by General Formula (G4).

[Chemical formula 16]

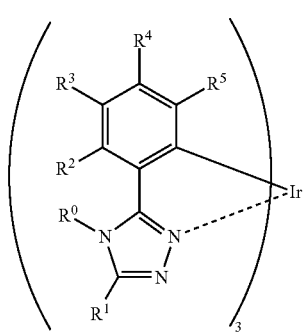

(G4)

In General Formula (G4), $R^0$ to $R^5$ are similar to those in General Formula (G3).

The iridium complex represented by General Formula (G3) has the advantage of allowing a light-emitting element to have high emission efficiency in the case where X represents carbon. This iridium complex is an iridium complex represented by General Formula (G5) or (G6).

[Chemical formula 17]

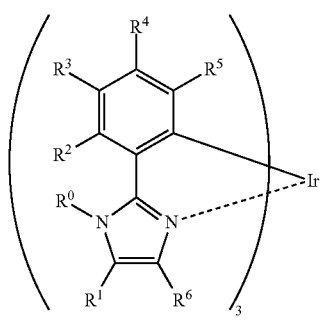

(G5)

In General Formula (G5), $R^0$ to $R^5$ are similar to those in General Formula (G3). $R^6$ represents any one of hydrogen, an alkyl group having 1 to 6 carbon atoms, and a phenyl group. The phenyl group may have, as a substituent, an alkyl group having 1 to 6 carbon atoms. Specific examples of an alkyl group having 1 to 6 carbon atoms include a methyl group, an ethyl group, a propyl group, an isopropyl group, a butyl group, a sec-butyl group, an isobutyl group, a tert-butyl group, a pentyl group, a hexyl group, and a cyclohexyl group.

In General Formula (G5), $R^1$ and $R^6$ may be bonded to each other to form a ring.

The ring formed by the bonded $R^1$ and $R^6$ may form a fused structure. The iridium complex can be represented by General Formula (G6).

[Chemical formula 18]

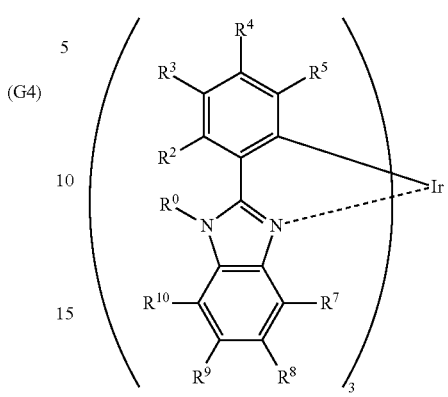

(G6)

In General Formula (G6), $R^0$ and $R^2$ to $R^5$ are similar to those in General Formula (G3). $R^7$ to $R^{10}$ separately represent hydrogen or an alkyl group having 1 to 6 carbon atoms. Specific examples of an alkyl group having 1 to 6 carbon atoms include a methyl group, an ethyl group, a propyl group, an isopropyl group, a butyl group, a sec-butyl group, an isobutyl group, a tert-butyl group, a pentyl group, a hexyl group, and a cyclohexyl group.

Next, an example of a synthesis method of the iridium complex in this embodiment will be described. The ligand of the iridium complex which is represented by General Formula (G0) can be synthesized by different synthesis methods depending on the number of nitrogen atoms of the five-membered ring; accordingly, four synthesis methods of the ligands with different structures will be described. Note that nitrogen-containing five-membered ring derivatives whose synthesis methods will be described below and which are represented by General Formulae (G0-4), (G0-5), (G0-6), and (G0-7) are substances included in the category of the nitrogen-containing five-membered ring derivative represented by General Formula (G0).

[Chemical formula 19]

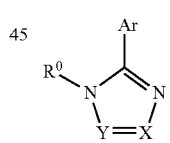

(G0)

In General Formula (G0), Ar represents an arylene group having 6 to 12 carbon atoms, and $R^0$ represents a tricycloalkyl group having a bridge structure and having 9 or 10 carbon atoms. X and Y separately represent carbon or nitrogen. When X or Y represents carbon, the carbon may have a substituent. When both X and Y represent carbon atoms, a benzene ring may be fused to the carbon atoms. When X and Y have substituents, the substituents may be bonded to each other to form a ring.

Synthesis Method of Nitrogen-Containing
Five-Membered Ring Derivative Represented by
General Formula (G0-4)

First, an example of a synthesis method of the nitrogen-containing five-membered ring derivative represented by General Formula (G0-4) will be described.

[Chemical formula 20]

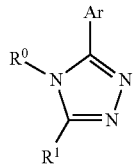

(G0-4)

In General Formula (G0-4), Ar represents an arylene group having 6 to 12 carbon atoms. Further, $R^0$ represents a tricycloalkyl group having a bridge structure and having 9 or 10 carbon atoms, and $R^1$ represents any one of hydrogen, an alkyl group having 1 to 6 carbon atoms, and a phenyl group.

As shown in Scheme (a-4), a thioether compound including an aryl group (Ar) and $R^0$ or an N-substituted thioamide compound including an aryl group (Ar) and $R^0$ (A1-4) is reacted with a hydrazide compound including $R^1$ (A2-4), whereby the nitrogen-containing five-membered ring derivative represented by General Formula (G0-4) can be obtained.

[Chemical formula 21]

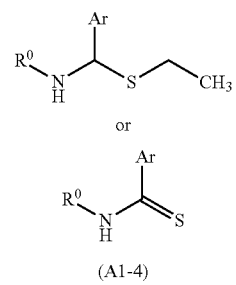 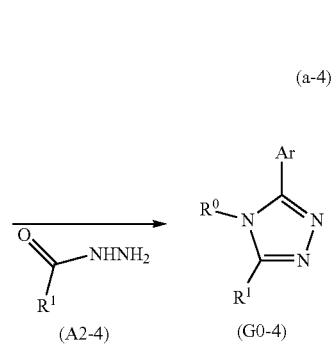

(a-4)

In Scheme (a-4), Ar represents an arylene group having 6 to 12 carbon atoms. Further, $R^0$ represents a tricycloalkyl group having a bridge structure and having 9 or 10 carbon atoms, and $R^1$ represents any one of hydrogen, an alkyl group having 1 to 6 carbon atoms, and a phenyl group.

The synthesis method of the nitrogen-containing five-membered ring derivative represented by General Formula (G0-4) is not limited to the method shown in Scheme (a-4). For example, there is another example of a synthesis method in which a thioether compound containing $R^1$ and $R^0$ or an N-substituted thioamide compound containing $R^1$ and $R^0$ is reacted with an aryl hydrazide compound.

As shown in Scheme (a'-4), there is also a method in which a dihydrazide compound (A1'-4) and a primary amine compound (A2'-4) are reacted with each other.

[Chemical formula 22]

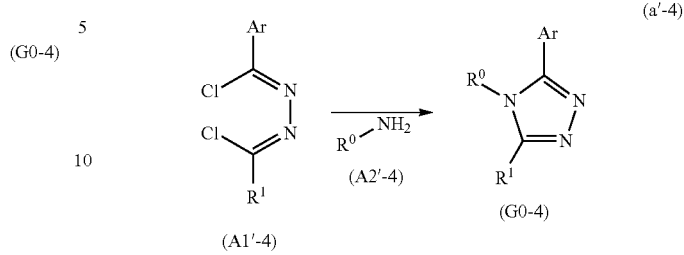

(a'-4)

In Scheme (a'-4), Ar represents an arylene group having 6 to 12 carbon atoms. Further, $R^0$ represents a tricycloalkyl group having a bridge structure and having 9 or 10 carbon atoms, and $R^1$ represents any one of hydrogen, an alkyl group having 1 to 6 carbon atoms, and a phenyl group.

Synthesis Method of Nitrogen-Containing Five-Membered Ring Derivative Represented by General Formula (G0-5)

Next, an example of a synthesis method of the nitrogen-containing five-membered ring derivative represented by General Formula (G0-5) will be described.

[Chemical formula 23]

(G0-5)

In General Formula (G0-5), Ar represents an arylene group having 6 to 12 carbon atoms. Further, $R^0$ represents a tricycloalkyl group having a bridge structure and having 9 or 10 carbon atoms, and $R^1$ and $R^6$ separately represent any one of hydrogen, an allyl group having 1 to 6 carbon atoms, and a phenyl group.

As shown in Scheme (a-5), an arylaldehyde compound including Ar (A1-5), a 1,2-diketone compound including $R^1$ and $R^6$ (A2-5), and a primary amine compound including $R^0$ (A3-5) are reacted with each other in the presence of ammonium acetate, whereby the nitrogen-containing five-membered ring derivative represented by General Formula (G0-5) can be obtained.

[Chemical formula 24]

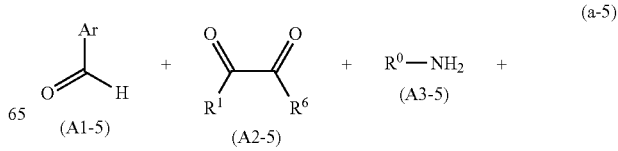

(a-5)

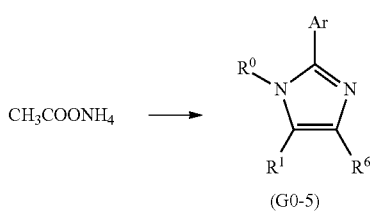

In Scheme (a-5), Ar represents an arylene group having 6 to 12 carbon atoms. Further, $R^0$ represents a tricycloalkyl group having a bridge structure and having 9 or 10 carbon atoms, and $R^1$ and $R^6$ separately represent any one of hydrogen, an alkyl group having 1 to 6 carbon atoms, and a phenyl group.

As shown in Scheme (a'-5), there is also a method in which an aryl imidazole compound (A1'-5) and a halide including $R^0$ (A2'-5) are reacted with each other.

[Chemical formula 25]

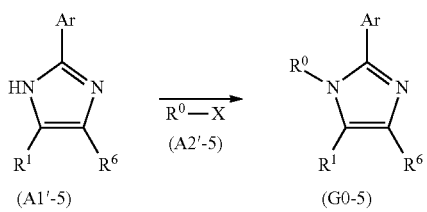

In Scheme (a'-5), Ar represents an arylene group having 6 to 12 carbon atoms. Further, $R^0$ represents a tricycloalkyl group having a bridge structure and having 9 or 10 carbon atoms, and $R^1$ and $R^6$ separately represent any one of hydrogen, an alkyl group having 1 to 6 carbon atoms, and a phenyl group. Further, X represents a halogeno group.

Synthesis Method of Nitrogen-Containing Five-Membered Ring Derivative Represented by General Formula (G0-6)

Next, an example of a synthesis method of the nitrogen-containing five-membered ring derivative represented by General Formula (G0-6) will be described.

[Chemical formula 26]

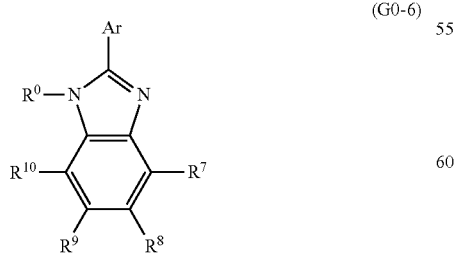

In General Formula (G0-6), Ar represents an arylene group having 6 to 12 carbon atoms. Further, $R^0$ represents a tricycloalkyl group having a bridge structure and having 9 or 10 carbon atoms, and $R^7$ to $R^{10}$ separately represent any one of hydrogen, an alkyl group having 1 to 6 carbon atoms, and a phenyl group.

As shown in Scheme (a-6), an arylaldehyde compound or aromatic acid chloride (A1-6) and an o-phenylenediamine derivative (A2-6) whose N-position is substituted with $R^0$ are reacted with each other, whereby the nitrogen-containing five-membered ring derivative represented by General Formula (G0-6) can be obtained.

[Chemical formula 27]

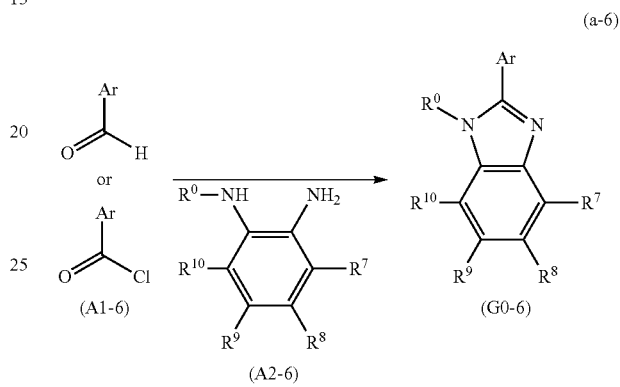

In Scheme (a-6), Ar represents an arylene group having 6 to 12 carbon atoms. Further, $R^0$ represents a tricycloalkyl group having a bridge structure and having 9 or 10 carbon atoms, and $R^7$ to $R^{10}$ separately represent any one of hydrogen, an alkyl group having 1 to 6 carbon atoms, and a phenyl group.

Synthesis Method of Nitrogen-Containing Five-Membered Ring Derivative Represented by General Formula (G0-7)

Lastly, an example of a synthesis method of the nitrogen-containing five-membered ring derivative represented by General Formula (G0-7) will be described.

[Chemical formula 28]

In General Formula (G0-7), Ar represents an arylene group having 6 to 12 carbon atoms, and $R^0$ represents a tricycloalkyl group having a bridge structure and having 9 or 10 carbon atoms.

As shown in Scheme (a-7), by a cycloaddition reaction between an equivalent of a nitrile whose N-position is substituted with $R^0$ (A1-7) and azide, the nitrogen-containing five-membered ring derivative represented by General Formula (G0-7) can be obtained.

[Chemical formula 29]

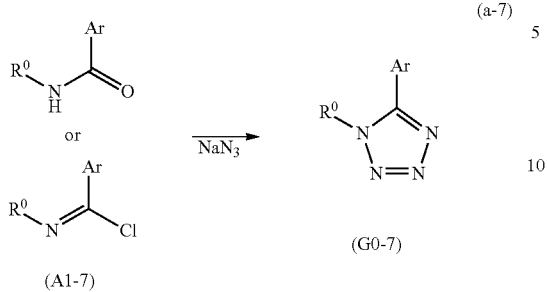

In Scheme (a-7), Ar represents an arylene group having 6 to 12 carbon atoms, and R⁰ represents a tricycloalkyl group having a bridge structure and having 9 or 10 carbon atoms.

Following the description of the synthesis methods of the ligand, a synthesis method of the complex will be described.

Synthesis Method of Organometallic Complex of One Embodiment of the Present Invention Represented by General Formula (G1)

The organometallic complex of one embodiment of the invention represented by General Formula (G1) can be synthesized by Synthesis Scheme (b). That is, the nitrogen-containing five-membered ring derivative represented by General Formula (G0) is mixed with an iridium compound which contains a halogen (e.g., iridium chloride, iridium bromide, iridium iodide, or ammonium hexachloroiridate) or with an iridium organometallic complex compound (e.g., an acetylacetonate complex, a diethylsulfide complex, a μ-halogen bridged dinuclear complex in which the nitrogen-containing five-membered ring derivative represented by General Formula (G0) is a ligand, or a μ-oxo bridged dinuclear complex in which the nitrogen-containing five-membered ring derivative represented by General Formula (G0) is a ligand) and the mixture is then heated, so that an organometallic complex having the structure represented by General Formula (G1) can be obtained. Further, this heating process may be performed after the nitrogen-containing five-membered ring derivative represented by General Formula (G0) and the iridium compound which contains a halogen or the iridium organometallic complex compound are dissolved in an alcohol-based solvent (e.g., glycerol, ethylene glycol, 2-methoxy ethanol, 2-ethoxyethanol, or phenol), and an appropriate base may be added. There is no particular limitation on a heating means, and an oil bath, a sand bath, or an aluminum block may be used. Alternatively, microwaves can be used as a heating means.

[Chemical formula 30]

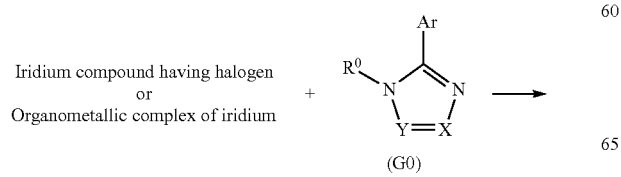

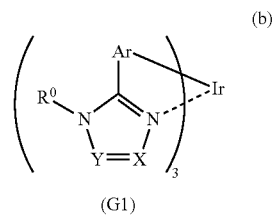

The iridium complex represented by General Formula (G1) can be synthesized as described above.

As specific examples of iridium complexes represented by General Formula (G1), iridium complexes represented by Structural Formulae (100) to (156) can be given. Note that the present invention is not limited to the iridium complexes represented by these structural formulae.

[Chemical formula 31]

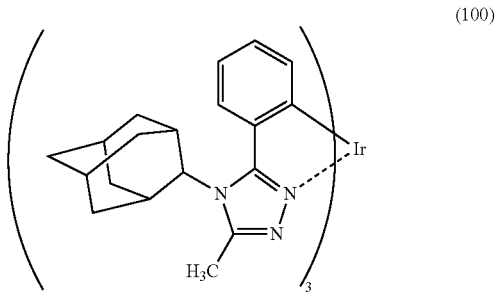

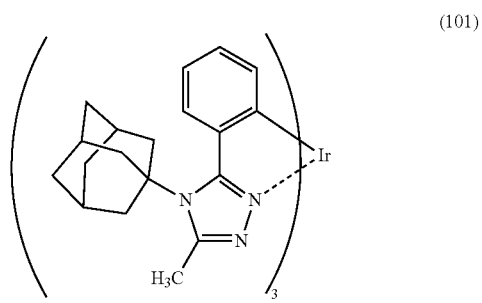

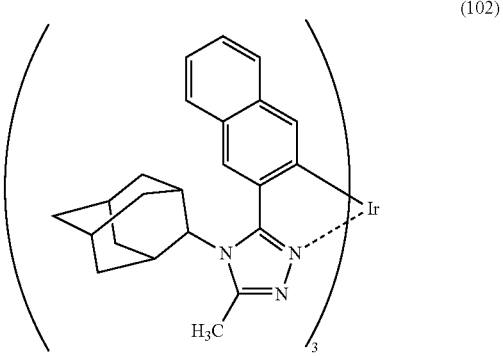

(103) 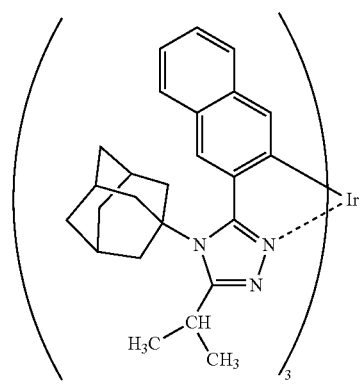
(104) 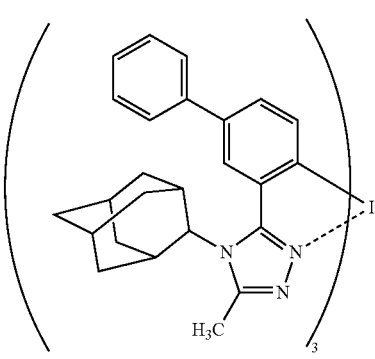
(105) 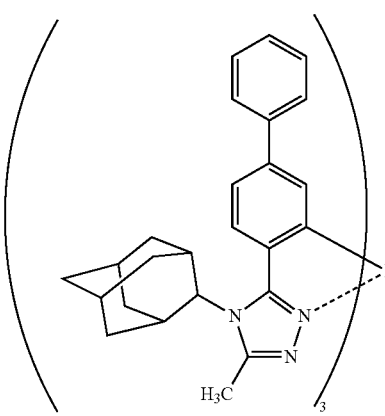
[Chemical formula 32]
(106) 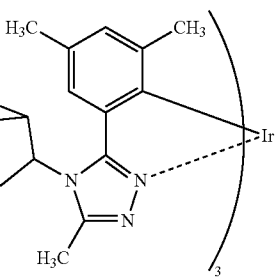
(107) 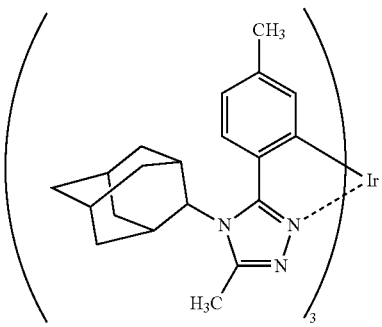
(108) 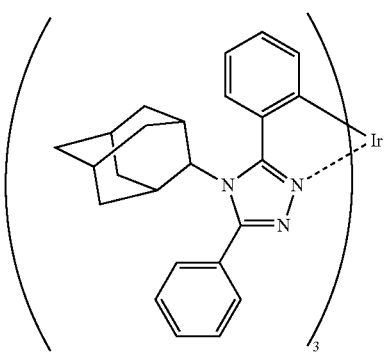
(109) 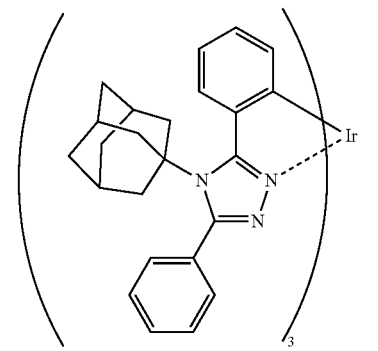
(110) 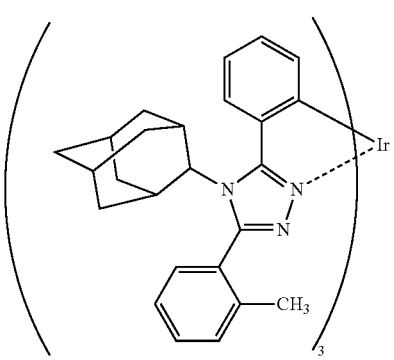

[Chemical formula 33]
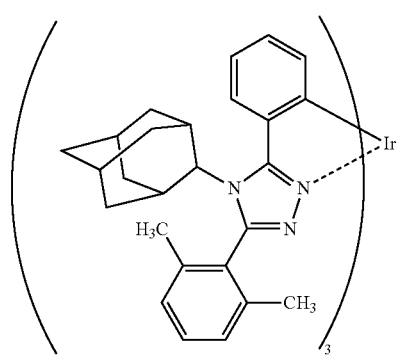
(111)
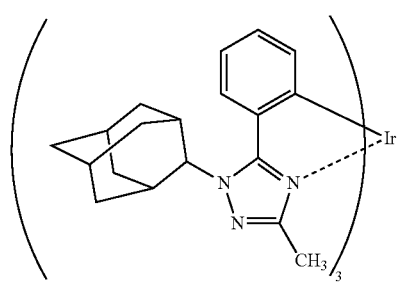
(112)
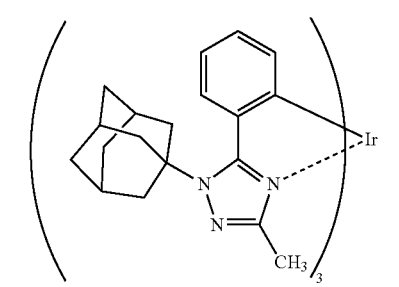
(113)
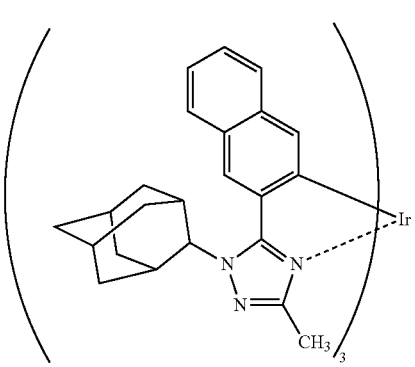
(114)
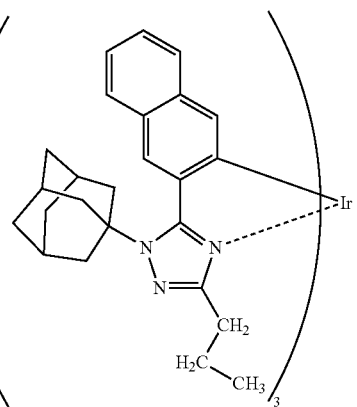
(115)
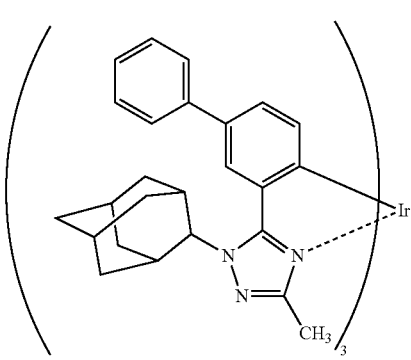
(116)
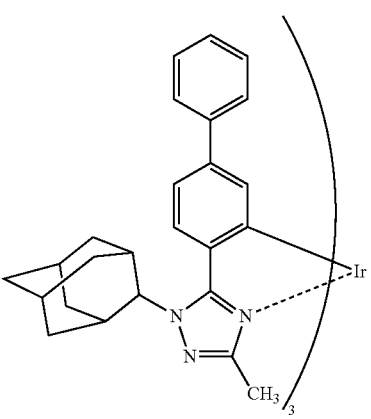
(117)
[Chemical formula 34]
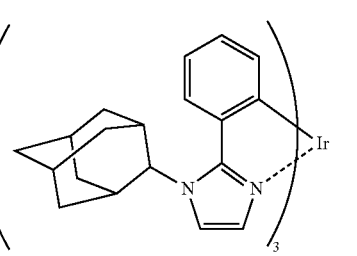
(118)

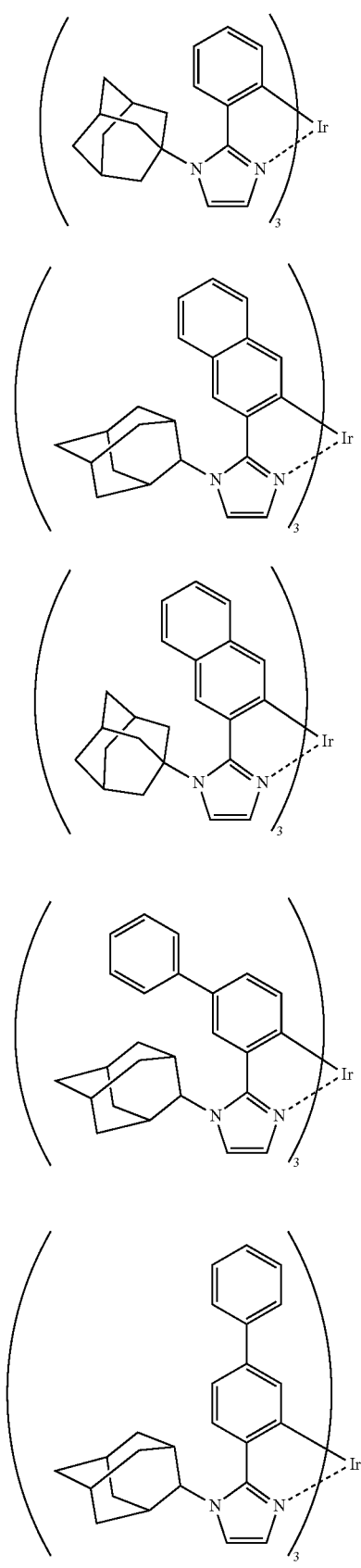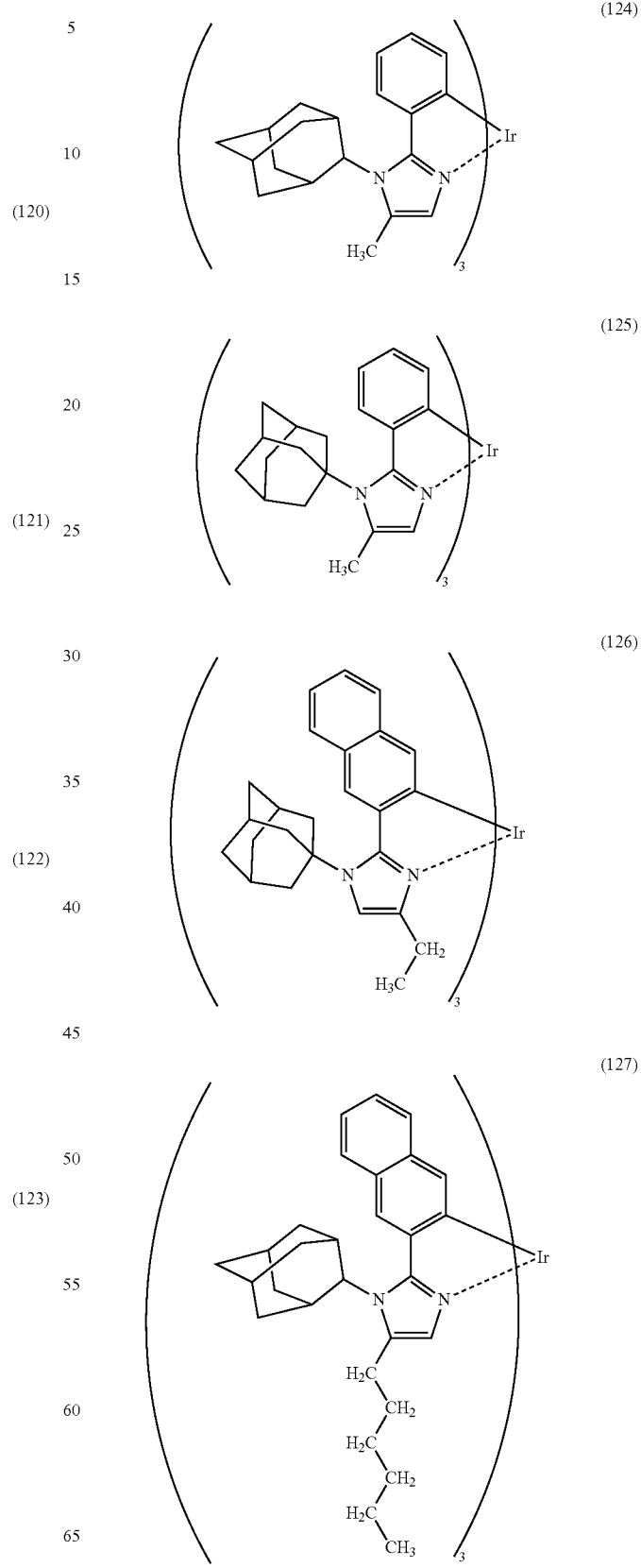

(128)
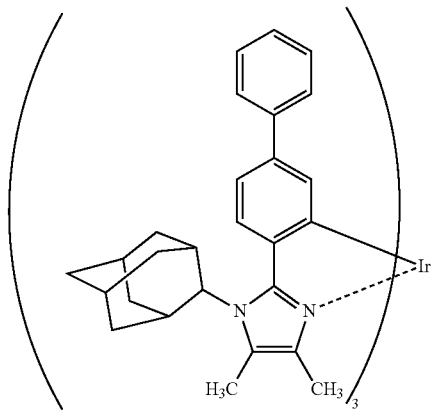
(129)
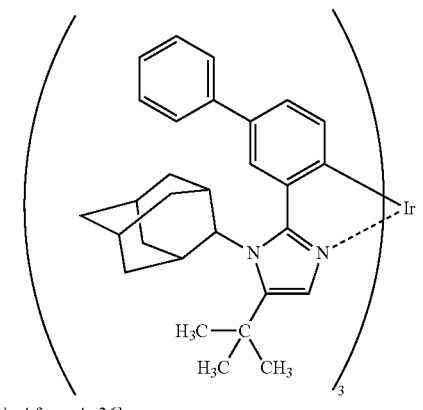
[Chemical formula 36]
(130)
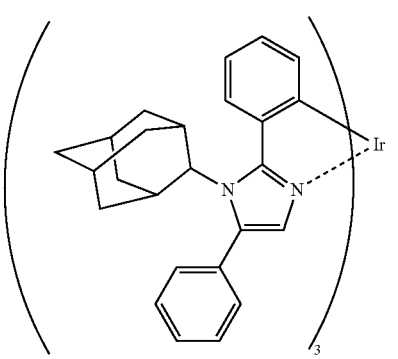
(131)
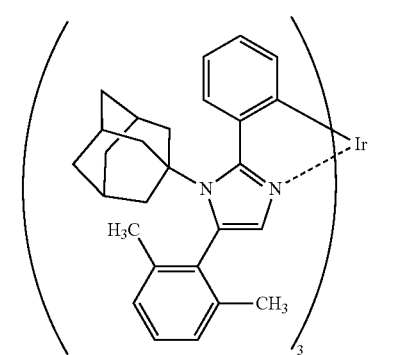
(132)
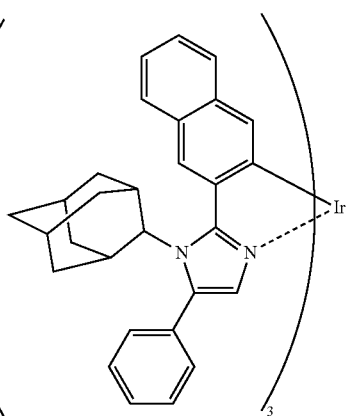
(133)
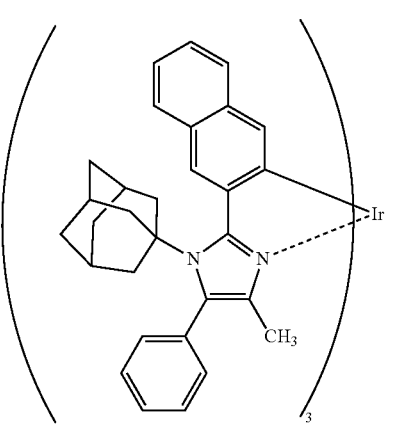
(134)
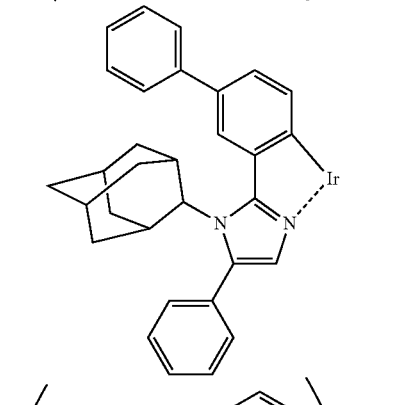
(135)
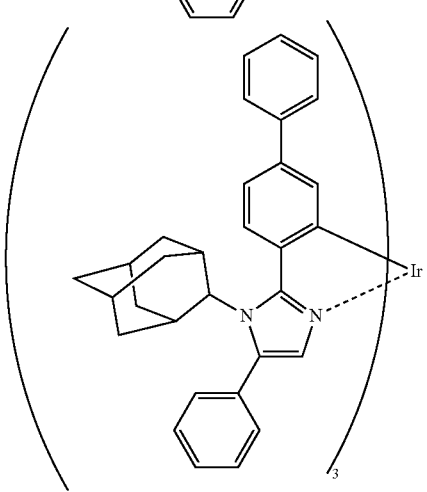

[Chemical formula 37]
(136)
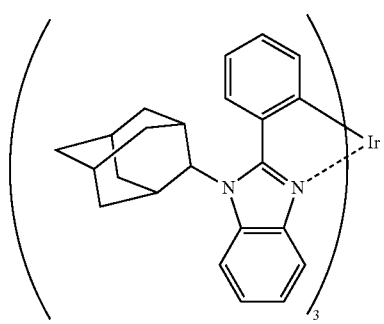
(137)
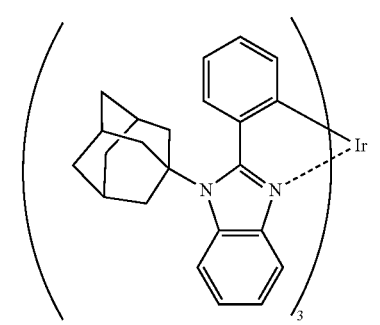
(138)
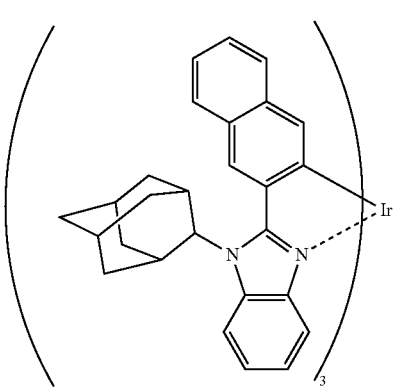
(139)
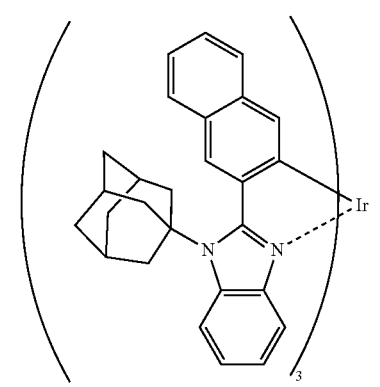
(140)
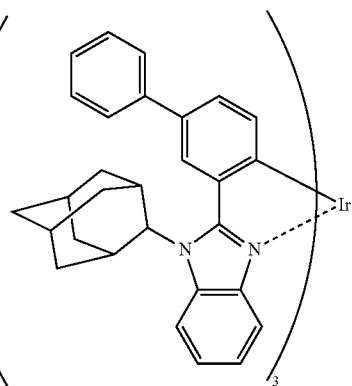
(141)
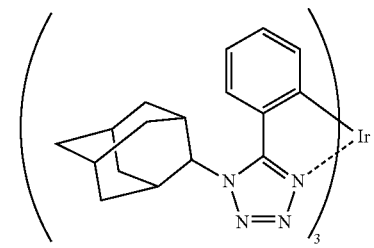
[Chemical formula 38]
(142)
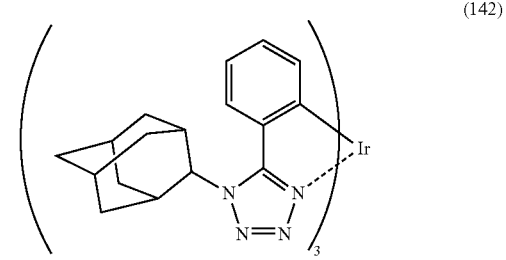
(143)
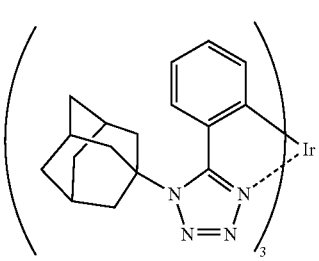

(144) 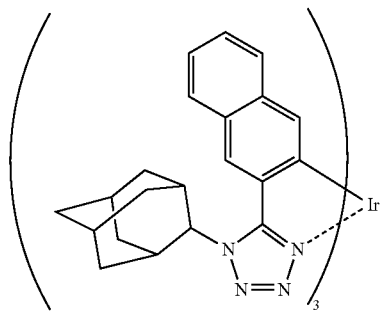
(145) 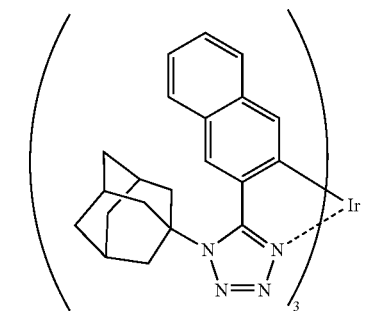
(146) 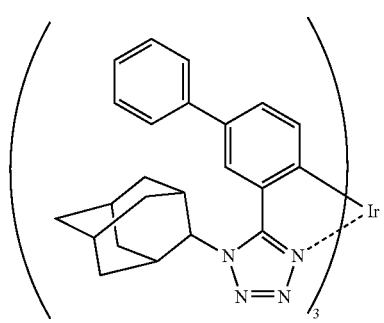
(147) 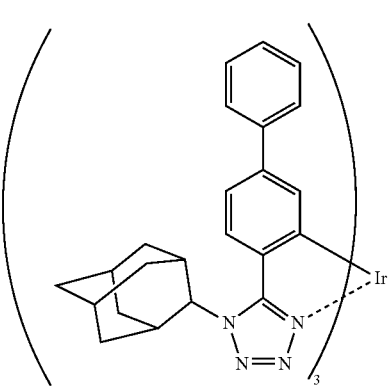
[Chemical formula 39]
(148) 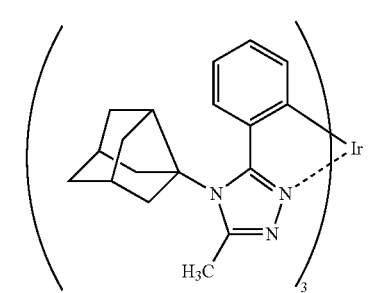
(149) 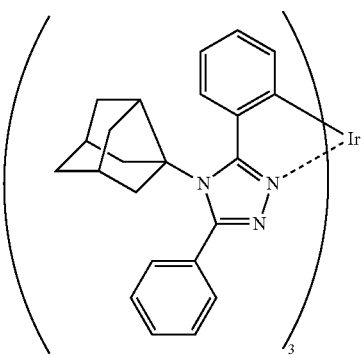
(150) 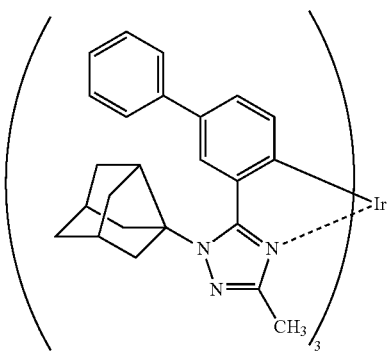
(151) 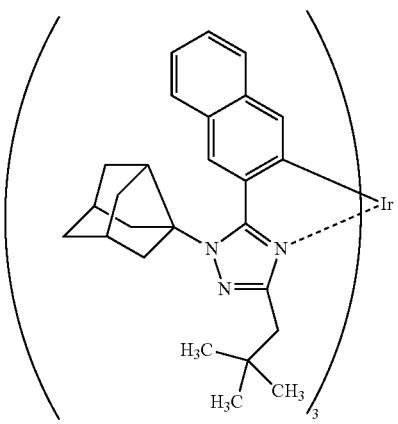
(152) 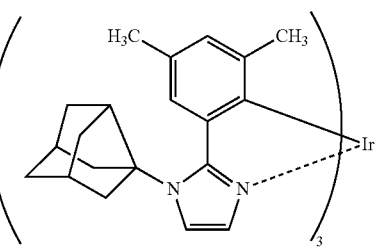

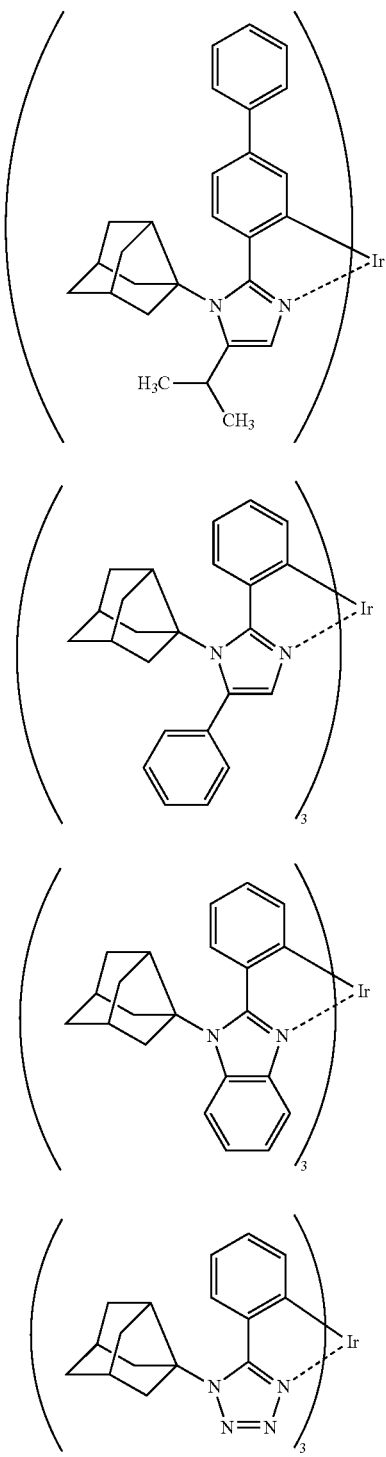

Depending on the type of the ligand, there can be stereoisomers of the iridium complexes represented by Structural Formulae (100) to (156), and such isomers are included in the category of the iridium complex of one embodiment of the present invention.

The above-described iridium complexes each of which is one embodiment of the present invention are novel substances capable of emitting blue phosphorescence.

(Embodiment 2)

In this embodiment, a light-emitting element using the iridium complex which is described in Embodiment 1 is described. Specifically, a light-emitting element in which the iridium complex is used for a light-emitting layer is described with reference to FIG. 1.

In a light-emitting element described in this embodiment, as illustrated in FIG. 1, an EL layer 102 including a light-emitting layer 113 is provided between a pair of electrodes (a first electrode 101 and a second electrode 103), and the EL layer 102 includes a hole-injection layer 111, a hole-transport layer 112, an electron-transport layer 114, an electron-injection layer 115, and the like in addition to the light-emitting layer 113.

In this embodiment, the first electrode 101 functions as an anode, and the second electrode 103 functions as a cathode. Note that when at least one of the first electrode 101 and the second electrode 103 has a light-transmitting property, light emitted from the EL layer 102 can be extracted to the outside to be used.

By application of a voltage to such a light-emitting element, holes injected from the first electrode 101 side and electrons injected from the second electrode 103 side recombine in the light-emitting layer 113 to raise the iridium complex to an excited state. Then, light is emitted when the iridium complex in the excited state returns to the ground state. Thus, the iridium complex in this embodiment functions as a light-emitting substance in the light-emitting element.

Note that the hole-injection layer 111 in the EL layer 102 is a layer containing a substance with a high hole-injection property, or a layer including a composite material containing a substance with a high hole-transport property and an acceptor substance. When the hole-injection layer is a layer including the composite material, electrons are extracted from the substance with a high hole-transport property by the acceptor substance and thus holes are generated. Thus, holes are injected from the hole-injection layer 111 into the light-emitting layer 113 through the hole-transport layer 112.

A specific example in which the light-emitting element described in this embodiment is fabricated is described.

As the first electrode 101 and the second electrode 103, a metal, an alloy, an electrically conductive compound, a mixture thereof, and the like can be used.

It is preferred that the first electrode 101 as the anode be formed using any of metals, alloys, and conductive compounds with a high work function (specifically, 4.0 eV or higher), a mixture thereof, or the like. Specifically, for example, indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide (IWZO), or the like is given. Films of these conductive metal oxides are generally formed by a sputtering method. For example, a film of indium oxide-zinc oxide can be formed by a sputtering method using a target obtained by adding 1 wt % to 20 wt % of zinc oxide to indium oxide. Moreover, a film of indium oxide containing tungsten oxide and zinc oxide (IWZO) can be formed by a sputtering method using a target in which 0.5 wt % to 5 wt % of tungsten oxide and 0.1 wt % to 1 wt % of zinc oxide with respect to indium oxide are included. Note that instead of a sputtering method, a sol-gel method can be applied and used to form the first electrode 101. Besides, as a material used for the first electrode 101, the following can be given: gold (Au), platinum (Pt), nickel (Ni), tungsten (W), chromium (Cr), molybdenum (Mo), iron (Fe), cobalt (Co), copper (Cu), palladium (Pd), a nitride of a metal material (e.g., titanium nitride), and the like. Graphene can also be used. Note that when a composite material described later is used for the hole-injection layer 111, any of a metal such as aluminum, an alloy, an electrically conductive compound, and a mixture thereof which have a small work function can also be used as the anode.

For the cathode, any of metals, alloys, electrically conductive compounds, and mixtures thereof which have a low work function (specifically, a work function of 3.8 eV or less) or the like can be used. Specific examples of such a cathode material include an element belonging to Group 1 or 2 of the periodic table, i.e., an alkali metal such as lithium (Li) or cesium (Cs), or an alkaline earth metal such as magnesium (Mg), calcium (Ca), or strontium (Sr); an alloy containing any of these (such as MgAg or AlLi); a rare earth metal such as europium (Eu) or ytterbium (Yb); an alloy containing such a rare earth metal; and the like. Any of a variety of conductive materials such as Al, Ag, ITO, indium oxide-tin oxide containing silicon or silicon oxide can be used for the cathode regardless of a work function when comprised in a stacked layer including a film of an alkali metal compound, an alkaline earth metal compound, or a rare earth metal compound (e.g., lithium fluoride (LiF), lithium oxide ($LiO_x$), cesium fluoride (CsF), calcium fluoride ($CaF_2$), or erbium fluoride ($ErF_3$)). Films of these conductive materials can be formed by a sputtering method, an ink-jet method, a spin coating method, or the like.

The hole-injection layer 111 is a layer which is provided in contact with the anode and contains a substance having a high hole-injection property. The hole-injection layer 111 can be formed using molybdenum oxide, vanadium oxide, ruthenium oxide, tungsten oxide, manganese oxide, or the like. Alternatively, the hole-injection layer 111 can be formed using a phthalocyanine-based compound such as phthalocyanine (abbreviation: $H_2Pc$) or copper phthalocyanine (abbreviation: CuPc); an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD); a polymer such as poly(ethylenedioxythiophene)/poly(styrenesulfonic acid) (PEDOT/PSS); or the like.

Alternatively, the hole-injection layer 111 can be formed using a composite material in which a substance exhibiting an acceptor property with respect to a substance having a high hole-transport property is contained in the substance having a high hole-transport property. Note that when the composite material in which a substance exhibiting an acceptor property is contained in a substance having a high hole-transport property is provided in contact with the anode, a material for forming the anode can be selected regardless of its work function. In other words, besides a material with a high work function, a material with a low work function may also be used for the anode. As the substance exhibiting an acceptor property, 7,7,8,8-tetracyano-2,3,5,6-tetrafluoroquinodimethane (abbreviation: $F_4$-TCNQ), chloranil, and the like are given. In addition, a transition metal oxide is given. Moreover, oxides of metals that belong to Group 4 to Group 8 of the periodic table can also be used. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air, has a low hygroscopic property, and is easily handled.

As the substance having a high hole-transport property used for the composite material, any of a variety of compounds such as an aromatic amine compound, a carbazole derivative, an aromatic hydrocarbon, and a high molecular compound (e.g., an oligomer, a dendrimer, or a polymer) can be used. The organic compound used for the composite material is preferably an organic compound having a high hole-transport property. Specifically, a substance having a hole mobility of $10^{-6}$ $cm^2/Vs$ or higher is preferably used. Note that any other substance may also be used as long as the hole-transport property thereof is higher than the electron-transport property thereof. The organic compounds that can be used for the composite material are specifically given below.

As the aromatic amine compounds, for example, there are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

As the carbazole derivatives which can be used for the composite material, the followings are given specifically: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like.

Other examples of the carbazole derivatives which can be used for the composite material include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene.

Examples of the aromatic hydrocarbon which can be used for the composite material include 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; and 2,5,8,11-tetra(tert-butyl)perylene. Besides those, pentacene, coronene, or the like can be used. In particular, the aromatic hydrocarbon which has a hole mobility of $1 \times cm^2/Vs$ or higher and which has 14 to 42 carbon atoms is particularly preferable.

The aromatic hydrocarbon which can be used for the composite material may have a vinyl skeleton. As the aromatic hydrocarbon having a vinyl group, 4,4'-bis(2,2-diphenylvinyl)biphenyl (abbreviation: DPVBi) and 9,10-bis[4-(2,2-diphenylvinyl)phenyl]anthracene (abbreviation: DPVPA) are given, for example.

Moreover, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), or poly[N,N'- bis(4-butylphenyl)-N,N'-bis(phenyl)benzidine (abbreviation: Poly-TPD) can also be used.

Note that a layer formed using such a composite material can be very suitably used for optical design that is performed to control the light extraction efficiency, directivity, or the like of light emitted from the light-emitting layer 113 because the drive voltage hardly varies even when the layer formed using the composite material is formed to be thick or thin.

The hole-transport layer 112 is formed using a substance with a high hole-transport property. As a substance with a high hole-transport property, for example, aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), and 4-phenyl-4'-(9-phenylfluoren-9-yl)triphenylamine (abbreviation: BPAFLP) can be used. The substances mentioned here are mainly ones that have a hole mobility of $10^{-6}$ $cm^2$/Vs or higher. Any of the organic compounds given above as examples of the substance having a high hole-transport property in the composite material can also be used for the hole-transport layer 112. Note that any other substance may also be used as long as the hole-transport property thereof is higher than the electron-transport property thereof. The layer containing a substance with a high hole-transport property is not limited to a single layer, and a stacked layer in which two or more layers containing any of the above-described substances are stacked may be used.

Further, for the hole-transport layer 112, a high molecular compound such as poly(N-vinylcarbazole) (abbreviation: PVK), or poly(4-vinyltriphenylamine) (abbreviation: PVTPA) can be used.

The light-emitting layer 113 contains the iridium complex described in Embodiment 1 as a guest material serving as a light-emitting substance and a substance that has higher triplet excitation energy than this iridium complex as a host material.

Preferable examples of the substance (i.e., host material) used for dispersing the above-described iridium complex include: any of compounds having an arylamine skeleton, such as 2,3-bis(4-diphenylaminophenyl)quinoxaline (abbreviation: TPAQn) and NPB, carbazole derivatives such as CBP and 4,4',4''-tris(N-carbazolyl)triphenylamine (abbreviation: TCTA), and metal complexes such as bis[2-(2-hydroxyphenyl)pyridinato]zinc (abbreviation: $Znpp_2$), bis [2-(2-hydroxyphenyl)benzoxazolato]zinc (abbreviation: $Zn(BOX)_2$), bis(2-methyl-8-quinolinolato)(4-phenylphenolato)aluminum (abbreviation: BAlq), and tris(8-quinolinolato)aluminum (abbreviation: $Alq_3$). Alternatively, a high molecular compound such as PVK can be used.

Note that in the case where the light-emitting layer 113 contains the above-described iridium complex (guest material) and the host material, green to blue phosphorescence with high emission efficiency can be obtained from the light-emitting layer 113.

The electron-transport layer 114 is a layer containing a substance having a high electron-transport property. For the electron-transport layer 114, metal complexes such as $Alq_a$, tris(4-methyl-8-quinolinolato)aluminum (abbreviation: $Almq_3$), bis(10-hydroxybenzo[h]quinolinato)beryllium (abbreviation: $BeBq_2$), BAlq, $Zn(BOX)_2$, or bis[2-(2-hydroxyphenyl)benzothiazolato]zinc (abbreviation: $Zn(BTZ)_2$) can be used. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butyl-phenyl)-4-phenyl-5-(4-biphenylyl)-1,2,4-triazole (abbreviation: TAZ), 3-(4-tert-butyl-phenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)](abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly ones that have an electron mobility of $10^{-6}$ $cm^2$/Vs or higher. Note that any other substance may also be used for the electron-transport layer as long as the electron-transport property thereof is higher than the hole-transport property thereof.

Further, the electron-transport layer 114 is not limited to a single layer, and a stacked layer in which two or more layers containing any of the above-described substances are stacked may be used.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride ($CaF_2$), or lithium oxide ($LiO_x$), can be used. Alternatively, a rare earth metal compound such as erbium fluoride ($ErF_3$) can be used. Further alternatively, the substances for forming the electron-transport layer 114, which are described above, can be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, for example, the substances for forming the electron-transport layer 114 (e.g., a metal complex and a heteroaromatic compound), which are described above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, alkali metal oxide or alkaline earth metal oxide such as lithium oxide, calcium oxide, barium oxide, and the like can be given. A Lewis base such as magnesium oxide can alternatively be used. An organic compound such as tetrathiafulvalene (abbreviation: TTF) can alternatively be used.

Note that each of the above-described hole-injection layer 111, hole-transport layer 112, light-emitting layer 113, electron-transport layer 114, and electron-injection layer 115 can be formed by a method such as an evaporation method (e.g., a vacuum evaporation method), an ink-jet method, or a coating method.

In the above-described light-emitting element, current flows due to a potential difference generated between the first electrode 101 and the second electrode 103, and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element can emit phosphorescence originating from the iridium complex described in Embodiment 1 and thus can have higher efficiency than a light-emitting element using a fluorescent compound.

Note that the light-emitting element described in this embodiment is an example of a light-emitting element fabricated using the iridium complex described in Embodiment 1. Further, as a light-emitting device including the above light-emitting element, a passive matrix light-emitting device and an active matrix light-emitting device can be manufactured. It is also possible to manufacture a light-emitting device with a microcavity structure including a light-emitting element which is a different light-emitting element from the above light-emitting elements as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

(Embodiment 3)

In this embodiment, as one embodiment of the present invention, a light-emitting element in which two or more kinds of organic compounds as well as a phosphorescent iridium complex are used for a light-emitting layer is described.

Figure 2:
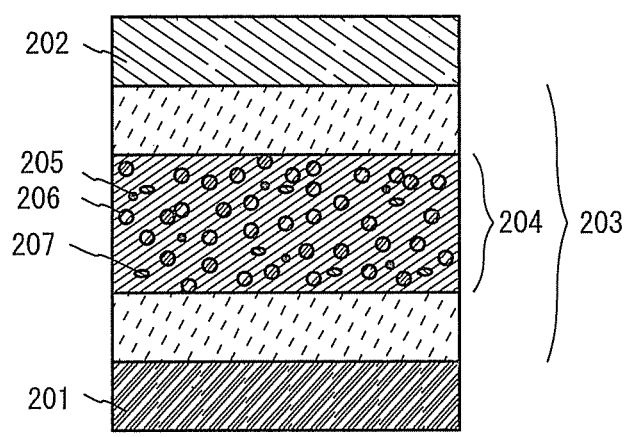
FIG. 2 illustrates an example of a light-emitting element.

A light-emitting element described in this embodiment includes an EL layer 203 between a pair of electrodes (a first electrode 201 and a second electrode 202) as illustrated in FIG. 2. Note that the EL layer 203 includes at least a light-emitting layer 204 and may include a hole-injection layer, a hole-transport layer, an electron-transport layer, an electron-injection layer, and the like. Note that substances for the hole-injection layer, the hole-transport layer, the electron-transport layer, and the electron-injection layer can be similar to the substances for the hole-injection layer 111, the hole-transport layer 112, the electron-transport layer 114, and the electron-injection layer 115, respectively, which are described in Embodiment 2.

In this embodiment, the first electrode 201 functions as an anode, and the second electrode 202 functions as a cathode. Note that the first electrode 201 and the second electrode 202 respectively correspond to the first electrode 101 and the second electrode 103 described in Embodiment 2.

The light-emitting layer 204 described in this embodiment contains a phosphorescent compound 205 using the iridium complex described in Embodiment 1, a first organic compound 206, and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

It is preferable that a triplet excitation energy level ($T_1$ level) of each of the first organic compound 206 and the second organic compound 207 be higher than that of the phosphorescent compound 205. The reason for this is that when the $T_1$ level of the first organic compound 206 or the second organic compound 207 is lower than that of the phosphorescent compound 205, the triplet excitation energy of the phosphorescent compound 205, which contributes to light emission, is transferred to the first organic compound 206 or the second organic compound 207 and accordingly the emission efficiency decreases.

Here, it is preferable that an emission spectrum of a host material (a fluorescence spectrum or a phosphorescence spectrum) largely overlap with an absorption spectrum of a guest material (specifically, a spectrum in an absorption band on the longest wavelength (lowest energy) side).

However, in general, it is difficult to obtain an overlap between a fluorescence spectrum of a host material and an absorption spectrum in an absorption band on the longest wavelength (lowest energy) side of a guest material. The reason for this is that fluorescence is emitted from an energy level higher than that of phosphorescence, and the $T_1$ level of a host material whose fluorescence spectrum has a wavelength close to an absorption spectrum of a guest material on the longest wavelength side is lower than the $T_1$ level of the guest material.

Thus, in this embodiment, a combination of the first organic compound 206 and the second organic compound 207 preferably forms an exciplex (also referred to as excited complex). In that case, the first organic compound 206 and the second organic, compound 207 form an exciplex by obtaining energy by recombination of electrons and holes at the time of recombination of carriers (electrons and holes) in the light-emitting layer 204. Fluorescence from the exciplex has a spectrum on a longer wavelength side than a fluorescence spectrum of the first organic compound 206 alone or the second organic compound 207 alone. Therefore, energy transfer from a singlet excited state can be maximized while the $T_1$ levels of the first organic compound and the second organic compound are kept higher than the $T_1$ level of the guest material.

For the phosphorescent compound 205, the phosphorescent organometallic iridium complex described in Embodiment 1 is used. Although the combination of the first organic compound 206 and the second organic compound 207 can be determined such that an exciplex is formed, a combination of a compound which is likely to accept electrons (a compound having an electron-trapping property) and a compound which is likely to accept holes (a compound having a hole-trapping property) is preferably employed.

As examples of a compound which is likely to accept electrons, the following can be given: 2-[3-(dibenzothiophen-4-yl)phenyl]dibenzo[f,h]quinoxaline (abbreviation: 2mDBTPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-

(dibenzothiophen-4-yl)phenyl]dibenzo[f,h]quinoxaline (abbreviation: 6mDBTPDBq-II).

As examples of a compound which is likely to accept holes, the following can be given: 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N-bis(9-phenylcarbazol-3-yl)-N,N'-diphenylbenzene-1,3-diamine (abbreviation: PCA2B), N-(9,9-dimethyl-2-N',N'-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N-(3-methylphenyl)-N-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound 206 to the second organic compound 207 is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of the light-emitting element.

Note that in another structure of the present invention, the light-emitting layer 204 can be formed using a host molecule having a hole-trapping property and a host molecule having an electron-trapping property as the two kinds of organic compounds other than the phosphorescent compound 205 that is the guest material so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

As a light-emitting device including the above light-emitting element, a passive matrix light-emitting device and an active matrix light-emitting device can be manufactured. It is also possible to manufacture a light-emitting device with a microcavity structure including a light-emitting element which is a different light-emitting element from the above light-emitting elements as described in another embodiment.

Note that there is no particular limitation on the structure of the in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

(Embodiment 4)

In this embodiment, as one embodiment of the present invention, a light-emitting element (hereinafter referred to as tandem light-emitting element) in which a charge generation layer is provided between a plurality of EL layers will be described.

Figure 3A:
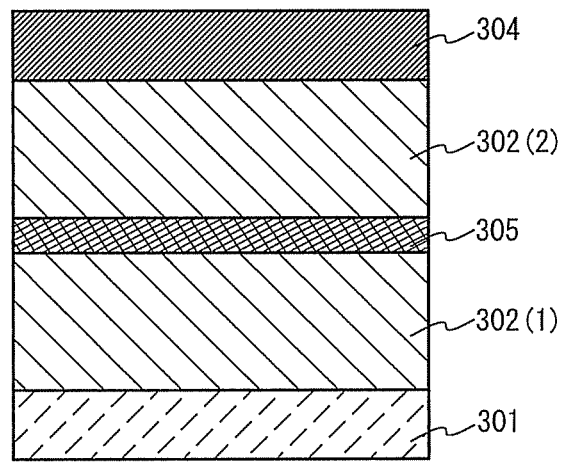
FIGS. 3A and 3B each illustrate an example of a light-emitting element.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those of the first electrode 101 and the second electrode 103 which are described in Embodiment 2.

In addition, although the plurality of EL layers (the first EL layer 302(1) and the second EL layer 302(2)) may have a structure similar to that of the EL layer described in Embodiment 2 or 3, any of the EL layers may have a structure similar to that of the EL layer described in Embodiment 2 or 3. In other words, the structures of the first EL layer 302(1) and the second EL layer 302(2) may be the same or different from each other and at least one of the first EL layer 302(1) and the second EL layer 302(2) has a structure similar to that of the EL layer described in Embodiment 2 or 3. Further, when the first EL layer 302(1) and the second EL layer 302(2) have different structures, one of them may have a known structure as long as the other of them has a structure similar to that of the EL layer described in Embodiment 2 or 3.

A charge generation layer 305 is provided between the EL layers (the first EL layer 302(1) and the second EL layer 302(2)). The charge generation layer 305 has a function of injecting electrons into one of the EL layers and injecting holes into the other of the EL layers when a voltage is applied between the first electrode 301 and the second electrode 304. Since the first electrode 301 is the anode and the second electrode 304 is the cathode, the charge generation layer 305 injects electrons into the first EL layer 302(1) and injects holes into the second EL layer 302(2).

Note that in terms of light extraction efficiency, the charge generation layer 305 preferably has a light-transmitting property with respect to visible light (specifically, the charge generation layer 305 has a visible light transmittance of 40% or more). Further, the charge generation layer 305 functions even if it has lower conductivity than the first electrode 301 or the second electrode 304.

The charge generation layer 305 may have either a structure (the composite material described in Embodiment 2) in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/Vs or higher. Note that substances other than the above substances may be used as long as they are organic compounds with a hole-transport property higher than an electron-transport property.

Further, as the electron acceptor, 7,7,8,8-tetracyano-2,3,5,6-tetrafluoroquinodimethane (abbreviation: F$_4$-TCNQ), chloranil, or the like can be used. Alternatively, a transition metal oxide can be used. Further alternatively, an oxide of metals that belong to Group 4 to Group 8 of the periodic table can be used. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air, has a low hygroscopic property, and is easily handled.

Note that the structure in which an electron acceptor is added to an organic compound having a high hole-transport property corresponds to the composite material described in Embodiment 2, and a structure similar to the composite material described in Embodiment 2 can be used; thus, the description is not repeated here. The description of the composite material in Embodiment 2 can be referred to.

On the other hand, in the case of the structure in which an electron donor is added to an organic compound having a high electron-transport property, as the organic compound having a high electron-transport property for example, a metal complex having a quinoline skeleton or a benzoquinoline skeleton, such as Alq, Almq$_3$, BeBq$_2$, or BAlq, or the like can be used. Alternatively, it is possible to use a metal complex having an oxazole-based ligand or a thiazole-based ligand, such as Zn(BOX)$_2$ or Zn(BTZ)$_2$. Further alternatively, instead of a metal complex, it is possible to use PBD, OXD-7, TAZ, BPhen, BCP, or the like. The substances mentioned here are mainly ones that have an electron mobility of $10^{-6}$ cm$^2$/Vs or higher. Note that substances other than the above substances may be used as long as they are organic compounds with an electron-transport property higher than a hole-transport property.

As the electron donor, it is possible to use an alkali metal, an alkaline earth metal, a rare earth metal, a metal belonging to Group 2 or 13 of the periodic table, or an oxide or a carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the electron donor.

Note that forming the charge generation layer 305 by using any of the above materials can suppress an increase in drive voltage caused by the stack of the EL layers.

Figure 3B:
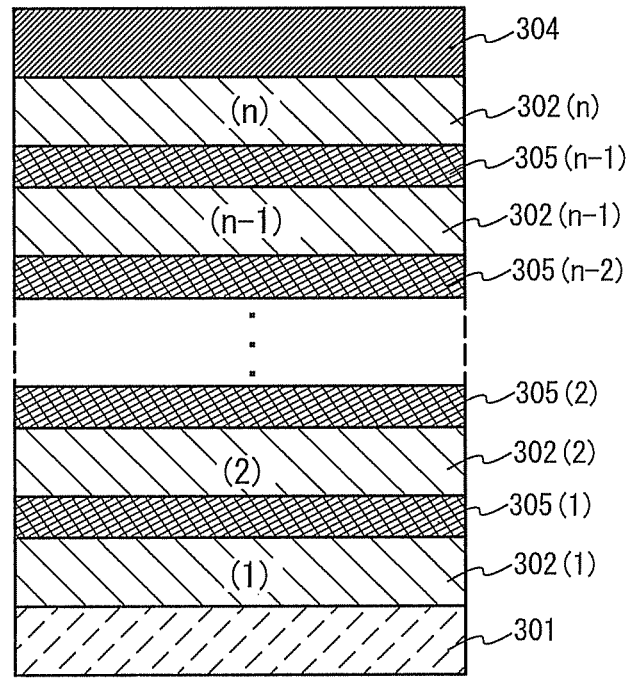

Although FIG. 3A illustrates the light-emitting element having two EL layers, the present invention can be similarly applied to a light-emitting element in which n EL layers (n is a natural number of three or more) are stacked as illustrated in FIG. 3B. In the case where a plurality of EL layers are included between a pair of electrodes as in the light-emitting element according to this embodiment, by provision of charge generation layers between the EL layers, light emission in a high luminance region can be obtained with current density kept low. Since the current density can be kept low, the element can have a long lifetime. Moreover, a light-emitting device having low driving voltage and lower power consumption can be obtained.

By making the EL layers emit light of different colors from each other, the light-emitting element can provide light emission of a desired color as a whole. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. In other words, when light obtained from a light-emitting substance and light of a complementary color are mixed, white light emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

(Embodiment 5)

In this embodiment, as a light-emitting device which is one embodiment of the present invention, a light-emitting device using the iridium complex described in Embodiment 1 is described.

Figure 4:
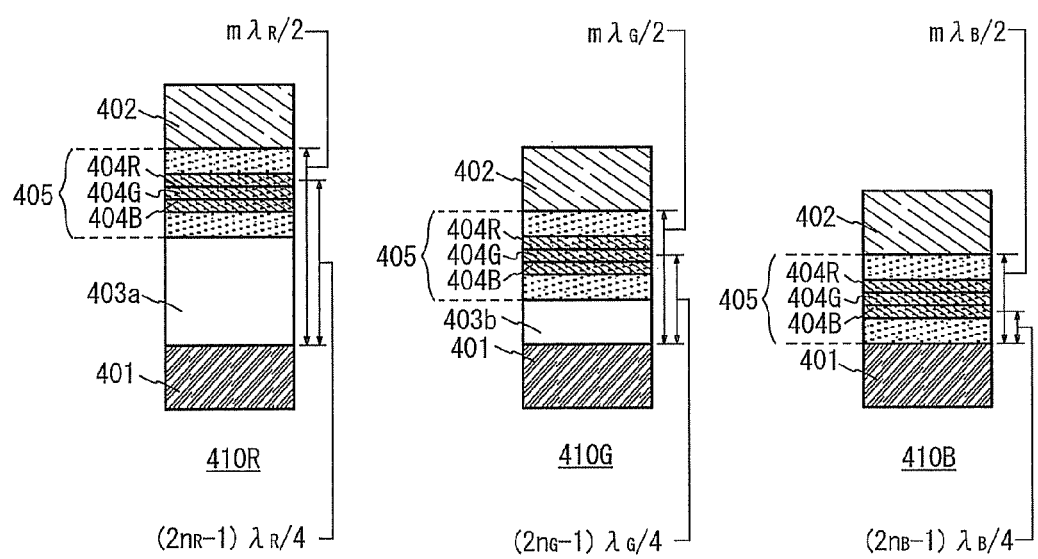
FIG. 4 illustrates an example of a light-emitting element.

A light-emitting device described in this embodiment has a micro optical resonator (microcavity) structure in which a light resonant effect between a pair of electrodes is utilized. The light-emitting device includes a plurality of light-emitting elements each of which has at least an EL layer 405 between a pair of electrodes (a reflective electrode 401 and a semi-transmissive and semi-reflective electrode 402) as illustrated in FIG. 4. Further, the EL layer 405 includes at least a light-emitting layer 404 serving as a light-emitting region and may further include a hole-injection layer, a hole-transport layer, an electron-transport layer, an electron-injection layer, a charge generation layer, and the like. Note that the light-emitting layer 404 contains the iridium complex described in Embodiment 1.

In this embodiment, a light-emitting device is described which includes light-emitting elements (a first light-emitting element 410R, a second light-emitting element 410G, and a third light-emitting element 410B) having different structures as illustrated in FIG. 4.

The first light-emitting element 410R has a structure in which a first transparent conductive layer 403a, an EL layer 405, and a semi-transmissive and semi-reflective electrode 402 are sequentially stacked over a reflective electrode 401. The second light-emitting element 410G has a structure in which a second transparent conductive layer 403b, the EL layer 405, and the semi-transmissive and semi-reflective electrode 402 are sequentially stacked over the reflective electrode 401. The third light-emitting element 410B has a structure in which the EL layer 405 and the semi-transmissive and semi-reflective electrode 402 are sequentially stacked over the reflective electrode 401.

Note that the reflective electrode 401, the EL layer 405, and the semi-transmissive and semi-reflective electrode 402 are common to the light-emitting elements (the first light-emitting element 410R, the second light-emitting element 410G, and the third light-emitting element 410B).

Further, the EL layer 405 includes a first light-emitting layer 404B, a second light-emitting layer 404G, and a third light-emitting layer 404R. Note that the first light-emitting layer 404B is presumed to emit light having a peak at a wavelength of about $\lambda_B$. The second light-emitting layer 404G is presumed to emit light having a peak at a wavelength of about $\lambda_G$. The third light-emitting layer 404R is presumed to emit light having a peak at a wavelength of about $\lambda_R$. From each of the light-emitting elements (the first light-emitting element 410R, the second light-emitting element 410G, and the third light-emitting element 410B), light emitted from the first light-emitting layer 404B, light emitted from the second light-emitting layer 404G, and light emitted from the third light-emitting layer 404R which overlap with each other can be obtained. Note that the above wavelengths satisfy the relation of $\lambda_B < \lambda_G < \lambda_R$.

Each of the light-emitting elements described in this embodiment has a structure in which the EL layer 405 is interposed between the reflective electrode 401 and the semi-transmissive and semi-reflective electrode 402. Light emitted in all directions from the light-emitting layers included in the EL layer 405 is partly reflected and resonated by the reflective electrode 401 and the semi-transmissive and semi-reflective electrode 402. Note that the reflective electrode 401 is formed using a conductive material having reflectivity, and a film whose visible light reflectivity is 40% to 100%, preferably 70% to 100%, and whose resistivity is $1 \times 10^{-2}$ Ωcm or lower is used. In addition, the semi-transmissive and semi-reflective electrode 402 is formed using a conductive material having reflectivity and a light-transmitting property, and a film whose visible light reflectivity is 20% to 80%, preferably 40% to 70%, and whose resistivity is $1 \times 10^{-2}$ Ωcm or lower is used.

In this embodiment, the thicknesses of the transparent conductive layers (the first transparent conductive layer 403a and the second transparent conductive layer 403b) provided in the first light-emitting element 410R and the second light-emitting element 410G, respectively, are varied between the light-emitting elements, whereby the light-emitting elements differ in the optical path length from the reflective electrode 401 to the semi-transmissive and semi-reflective electrode 402. In other words, lights each having a broad spectrum, which are emitted by the light-emitting elements, are resonated with the respective resonant wavelengths of the lights of the colors, so that lights with wavelengths which are different between the colors are intensified to be extracted.

Note that the optical path length (also referred to as optical distance) is expressed as a product of an actual distance and a refractive index, and in this embodiment, is a product of an actual thickness and n (refractive index). That is, an optical path length=actual thickness×n.

Note that the optical path length from the reflective electrode 401 to the semi-transmissive and semi-reflective electrode 402 is set to $m\lambda_R/2$ (m is a natural number of 1 or more) in the first light-emitting element 410R; the optical path length from the reflective electrode 401 to the semi-transmissive and semi-reflective electrode 402 is set to $m\lambda_G/2$ (m is a natural number of 1 or more) in, the second light-emitting element 410G; and the optical path length from the reflective electrode 401 to the semi-transmissive and semi-reflective electrode 402 is set to $m\lambda_B/2$ (m is a natural number of 1 or more) in the third light-emitting element 410B. That is, when the wavelength of light to extract is λ, the optical wavelength for resonation may be set to $m\lambda/2$ (m is a natural number of 1 or more).

In this manner, the light $(\lambda_R)$ emitted from the third light-emitting layer 404R included in the EL layer 405 is mainly intensified to be extracted from the first light-emitting element 410R, the light $(\lambda_G)$ emitted from the second light-emitting layer 404G included in the EL layer 405 is mainly intensified to be extracted from the second light-emitting element 410G, and the light $(\lambda_B)$ emitted from the first light-emitting layer 404B included in the EL layer 405 is mainly intensified to be extracted from the third light-emitting element 410B. Note that the light extracted from each of the light-emitting elements is emitted from the semi-transmissive and semi-reflective electrode 402 side.

Note that in the above structure, strictly speaking, the optical path length from the reflective electrode 401 to the semi-transmissive and semi-reflective electrode 402 can be the length from a reflection region in the reflective electrode 401 to a reflection region in the semi-transmissive and semi-reflective electrode 402. However, it is difficult to precisely determine the positions of the reflection regions in the reflective electrode 401 and the semi-transmissive and semi-reflective electrode 402; therefore, the above effect can be sufficiently obtained wherever the reflection regions may be set in the reflective electrode 401 and the semi-transmissive and semi-reflective electrode 402.

Further, the optical path length from the reflective electrode 401 to the third light-emitting layer 404R is preferably adjusted to $(2n_R-1)\lambda_R/4$, where $n_R$ is a natural number of 1 or more, because in the first light-emitting element 410R, light (first reflected light) that is first reflected by the reflective electrode 401 of the light emitted from the third light-emitting layer 404R considerably interferes with light (first incident light) that directly enters the semi-transmissive and semi-reflective electrode 402 from the third light-emitting layer 404R. By adjusting the optical path length, the phases of the first reflected light and the first incident light can be aligned with each other and the light emitted from the third light-emitting layer 404R can be further amplified.

Note that strictly speaking, the optical path length from the reflective electrode 401 to the third light-emitting layer 404R can be the optical path length from a reflection region in the reflective electrode 401 to a light-emitting region in the third light-emitting layer 404R. However, it is difficult to precisely determine the positions of the reflection region in the reflective electrode 401 and the light-emitting region in the third light-emitting layer 404R; therefore, it is presumed that the above effect can be sufficiently obtained wherever the reflection region and the light-emitting region may be set in the reflective electrode 401 and the third light-emitting layer 404R, respectively.

Next, the optical path length of the second light-emitting element 410G which emits light with the wavelength of $\lambda_G$ and that of the light-emitting element 410B which emits light with the wavelength of $\lambda_B$ are adjusted in a manner similar to that of the optical path length of light-emitting element 410R, whereby light emitted from each of the light-emitting elements can be amplified.

Note that although each of the light-emitting elements in the above-described structure includes a plurality of light-emitting layers in the EL layer, the present invention is not limited thereto; for example, the structure of the tandem light-emitting element which is described in Embodiment 4 can be combined, in which case a plurality of EL layers are provided so that a charge generation layer is interposed therebetween in one light-emitting element and one or more light-emitting layers are formed in each of the EL layers.

The light-emitting device described in this embodiment has a microcavity structure, in which lights with wavelengths which differ between the light-emitting elements can be extracted even when the light-emitting elements share the same EL layer, so that it is not needed to form light-emitting elements for the colors of R, G, and B. Therefore, higher-resolution display can be easily achieved. Further, with the use of color filters at the same time, light with higher color purity can be obtained and the light-emitting device can have high color reproductivity. In addition, emission intensity with a predetermined wavelength in the front direction can be increased, whereby power consumption can be reduced. The above structure is particularly useful in the case of being applied to a color display (image display device) including pixels of three or more colors but may also be applied to lighting or the like.

(Embodiment 6)

In this embodiment, a light-emitting device including a light-emitting element in which the iridium complex described in Embodiment 1 is used for a light-emitting layer is described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 5A and 5B.

Figure 5A:
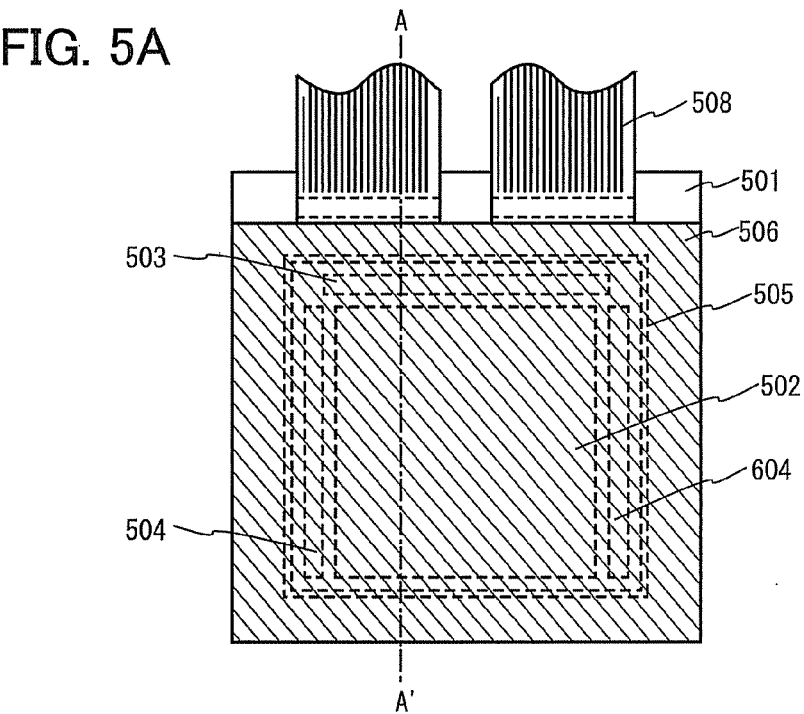
FIGS. 5A and 5B illustrate an example of an active matrix light-emitting device.
Figure 5B:
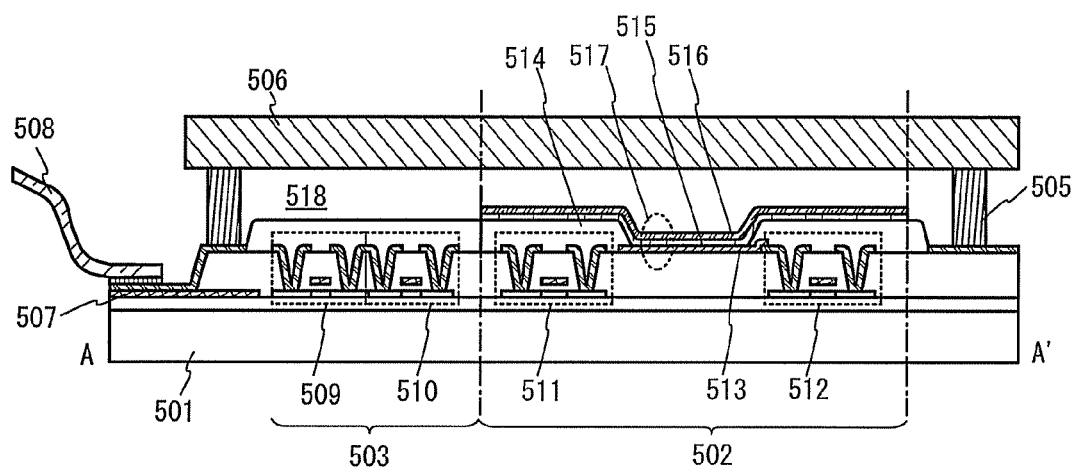

Note that FIG. 5A is a top view illustrating a light-emitting device and FIG. 5B is a cross-sectional view taken along the chain line A-A' in FIG. 5A. The active matrix light-emitting device according to this embodiment includes a pixel portion 502 provided over an element substrate 501, a driver circuit portion (a source line driver circuit) 503, and a driver circuit portion (a gate line driver circuit) 504. The pixel portion 502, the driver circuit portion 503, and the driver circuit portion 504 are sealed between the element substrate 501 and a sealing substrate 506 with a sealant 505.

In addition, a lead wiring 507 is provided over the element substrate 501. The lead wiring 507 is provided for connecting an external input terminal through which a signal (e.g., a video signal, a clock signal, a start signal, and a reset signal) or a potential from the outside is transmitted to the driver circuit portion 503 and the driver circuit portion 504. Here is shown an example in which a flexible printed circuit (FPC) 508 is provided as the external input terminal.

Although the FPC 508 is illustrated alone, this FPC may be provided with a printed wiring board (PWB). The light-emitting device in the present specification includes, in its category, not only the light-emitting device itself but also the light-emitting device provided with the FPC or the PWB.

Next, a cross-sectional structure is described with reference to FIG. 5B. The driver circuit portion and the pixel portion, are formed over the element substrate 501; here are illustrated the driver circuit portion 503 which is the source line driver circuit and the pixel portion 502.

The driver circuit portion 503 is an example where a CMOS circuit is formed, which is a combination of an n-channel TFT 509 and a p-channel TFT 510. Note that a circuit included in the driver circuit portion may be formed using various CMOS circuits, PMOS circuits, or NMOS circuits. Although this embodiment shows a driver integrated type in which the driver circuit is formed over the substrate, the driver circuit is not necessarily formed over the substrate, and may be formed outside the substrate.

The pixel portion 502 is formed of a plurality of pixels each of which includes a switching TFT 511, a current control TFT 512, and a first electrode 513 which is electrically connected to a wiring (a source electrode or a drain electrode) of the current control TFT 512. Note that an insulator 514 is formed to cover end portions of the first electrode 513. In this embodiment, the insulator 514 is formed using a positive photosensitive acrylic resin.

The insulator 514 preferably has a curved surface with curvature at an upper end portion or a lower end portion thereof in order to obtain favorable coverage by a film which is to be stacked over the insulator 514. For example, in the case of using a positive photosensitive acrylic resin as a material for the insulator 514, the insulator 514 preferably has a curved surface with a radius of curvature (0.2 µm to 3 µm) at the upper end portion. Note that the insulator 514 can be formed using either a negative photosensitive resin or a positive photosensitive resin. The material of the insulator 514 is not limited to an organic compound and an inorganic compound such as silicon oxide or silicon oxynitride can also be used.

An EL layer 515 and a second electrode 516 are stacked over the first electrode 513. In the EL layer 515, at least a light-emitting layer is provided which contains the iridium complex described in Embodiment 1. Further, in the EL layer 515, a hole-injection layer, a hole-transport layer, an electron-transport layer, an electron-injection layer, a charge generation layer, and the like can be provided as appropriate in addition to the light-emitting layer.

A light-emitting element 517 is formed of a stacked structure of the first electrode 513, the EL layer 515, and the second electrode 516. For the first electrode 513, the EL layer 515, and the second electrode 516, the materials described in Embodiment 2 can be used. Although not illustrated, the second electrode 516 is electrically connected to the FPC 508 which is an external input terminal.

Note that in this embodiment, the first electrode 513 functions as an anode, and the second electrode 516 functions as a cathode.

Although the cross-sectional view of FIG. 5B illustrates only one light-emitting element 517, a plurality of light-emitting elements are arranged in matrix in the pixel portion 502. Light-emitting elements which provide three kinds of light emission (R, G, and B) are selectively formed in the pixel portion 502, whereby a light-emitting device capable of full color display can be fabricated. Alternatively, a light-emitting device which is capable of full color display may be fabricated by a combination with color filters.

Further, the sealing substrate 506 is attached to the element substrate 501 with the sealant 505, whereby the light-emitting element 517 is provided in a space 518 surrounded by the element substrate 501, the sealing substrate 506, and the sealant 505. The space 518 may be filled with an inert gas (such as nitrogen or argon), or the sealant 505.

An epoxy-based resin is preferably used for the sealant 505. It is preferable that such a material do not transmit moisture or oxygen as much as possible. As the sealing substrate 506, a glass substrate, a quartz substrate, or a plastic substrate formed of fiberglass reinforced plastic (FRP), polyvinyl fluoride) (PVF), polyester, acrylic, or the like can be used.

As described above, an active matrix light-emitting device can be obtained.

Note that the structure described in this embodiment can be combined as appropriate with any of the structures described in the other embodiments.

(Embodiment 7)

In this embodiment, examples of a variety of electronic devices which are completed using a light-emitting device will be described with reference to FIGS. 6A to 6D. To the light-emitting device, the iridium complex described in Embodiment 1 is applied.

Examples of the electronic devices to which the light-emitting device is applied are a television device (also referred to as television or television receiver), a monitor of a computer or the like, a camera such as a digital camera or a digital video camera, a digital photo frame, a mobile phone (also referred to as cellular phone or cellular phone device), a portable game machine, a portable information terminal, an audio reproducing device, and a large-sized game machine such as a pachinko machine. Specific examples of these electronic devices are illustrated in FIGS. 6A to 6D.

FIG. 6A illustrates an example of a television set. In a television set 7100, a display portion 7103 is incorporated in a housing 7101. Images can be displayed on the display portion 7103, and the light-emitting device can be used for the display portion 7103. In addition, here, the housing 7101 is supported by a stand 7105.

Operation of the television set 7100 can be performed with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television set 7100 is provided with a receiver, a modem, and the like. With the receiver, a general television broadcast can be received. Furthermore, when the television set 7100 is connected to a communication network by wired or wireless connection via the modem, one-way (from a transmitter to a receiver) or two-way (between a transmitter and a receiver, between receivers, or the like) data communication can be performed.

FIG. 6B illustrates a computer having a main body 7201, a housing 7202, a display portion 7203, a keyboard 7204, an external connection port 7205, a pointing device 7206, and the like. Note that this computer is manufactured using the light-emitting device for the display portion 7203.

FIG. 6C illustrates a portable game machine having two housings, a housing 7301 and a housing 7302, which are connected with a joint portion 7303 so that the portable game machine can be opened or folded. A display portion 7304 is incorporated in the housing 7301, and a display portion 7305 is incorporated in the housing 7302. In addition, the portable game machine illustrated in FIG. 6C includes a speaker portion 7306, a recording medium insertion portion 7307, an LED lamp 7308, input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the light-emitting device is used for at least one of the display portion 7304 and the display portion 7305, and may include other accessories as appropriate. The portable game machine illustrated in FIG. 6C has a function of reading out a program or data stored in a storage medium to display it on the display portion, and a function of sharing information with another portable game machine by wireless communication. The functions of the portable game machine illustrated in FIG. 6C are not limited to these, and the portable game machine can have a variety of functions.

FIG. 6D illustrates an example of a mobile phone. A mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using the light-emitting device for the display portion 7402.

When the display portion 7402 of the mobile phone 7400 illustrated in FIG. 6D is touched with a finger or the like, data can be input to the mobile phone 7400. Further, operations such as making a call and composing an e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically switched by determining the orientation of the mobile phone 7400 (whether the mobile phone is placed horizontally or vertically for a landscape mode or a portrait mode).

The screen modes are switched by touching the display portion 7402 or operating the operation buttons 7403 of the housing 7401. The screen modes can also be switched depending on the kind of image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits near-infrared light in the display portion, an image of a finger vein, a palm vein, or the like can be taken.

As described above, the electronic devices can be obtained by application of the light-emitting device to which the iridium complex described in Embodiment 1 is applied. The light-emitting device has a remarkably wide application range, and can be applied to electronic devices in a variety of fields.

Note that the structure described in this embodiment can be combined as appropriate with any of the structures described in the other embodiments.

(Embodiment 8)

In this embodiment, examples of a lighting device to which a light-emitting device including the iridium complex described in Embodiment 1 is applied will be described with reference to FIG. 7.

Figure 7:
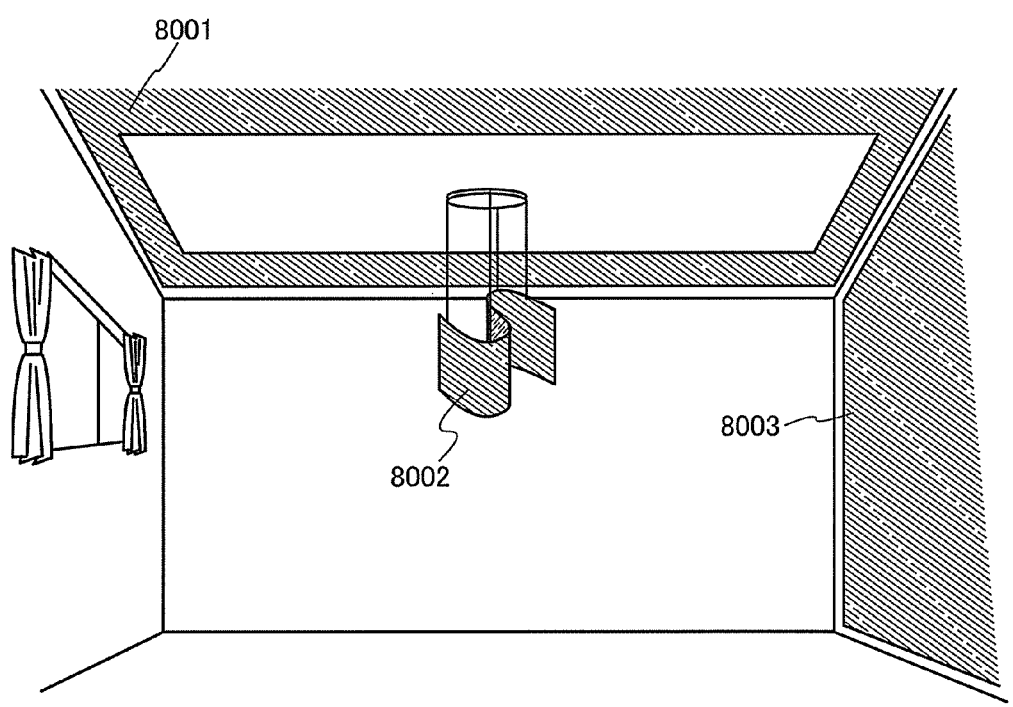
FIG. 7 illustrates examples of lighting devices.

FIG. 7 illustrates an example in which the light-emitting device is used as an indoor lighting device 8001. Since the light-emitting device can have a large area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

Note that the structure described in this embodiment can be combined as appropriate with any of the structures described in the other embodiments.

(Embodiment 9)

Figure 8:
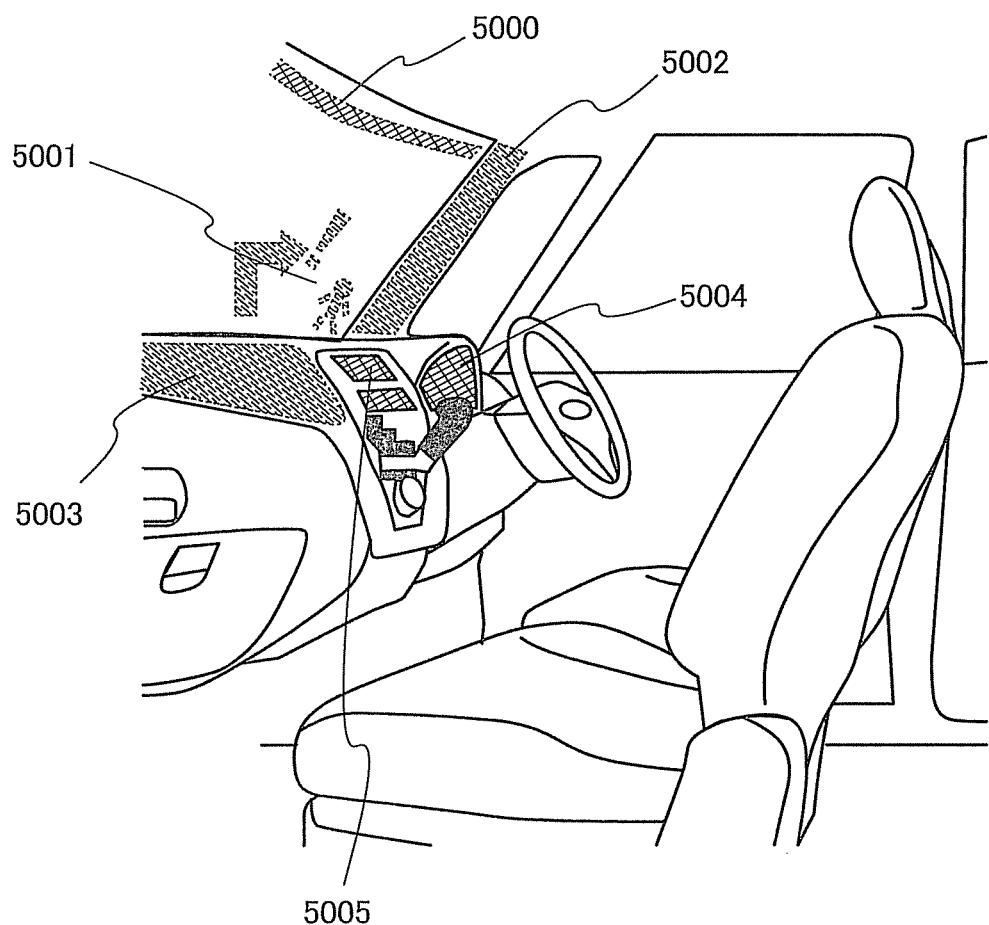
FIG. 8 illustrates examples of vehicle-mounted display devices.

The light-emitting element including the iridium complex described in Embodiment 1 can also be used for an automobile windshield or an automobile dashboard. FIG. 8 illustrates one mode in which the light-emitting elements including the iridium complex described in Embodiment 1 are used for an automobile windshield and an automobile dashboard. Displays 5000 to 5005 each include the light-emitting element including the iridium complex described in Embodiment 1.

The display 5000 and the display 5001 are display devices which are provided in the automobile windshield and in which the light-emitting elements including the iridium complex described in Embodiment 1 are incorporated. The light-emitting element including the iridium complex described in Embodiment 1 can be formed into what is called a see-through display device, through which the opposite side can be seen, by including a first electrode and a second electrode formed of electrodes having light-transmitting properties. Such see-through display devices can be provided even in the windshield of the car, without hindering the vision. Note that in the case where a transistor for driving or the like is provided, a transistor having a light-transmitting property, such as an organic transistor using an organic semiconductor material or a transistor using an oxide semiconductor, is preferably used.

The display 5002 is a display device which is provided in a pillar portion and in which the light-emitting element including the iridium complex described in Embodiment 1 is incorporated. The display 5002 can compensate for the view hindered by the pillar portion by showing an image taken by an imaging unit provided in the car body. Similarly, the display 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display 5004 and the display 5005 can provide a variety of kinds of information such as navigation data, a speedometer, a tachometer, a mileage, a fuel meter, a gear-shift indicator, and air-condition setting. The content or layout of the display can be changed freely by a user as appropriate. Note that such information can also be shown by the displays 5000 to 5003. The displays 5000 to 5005 can also be used as lighting devices.

A light-emitting element which includes the iridium complex described in Embodiment 1 can have high emission efficiency and low power consumption. In addition, the light-emitting element can be fabricated at low cost. Therefore, load on a battery is small even when a number of large screens such as the displays 5000 to 5005 are provided, which provides comfortable use. For that reason, the light-emitting device and the lighting device each of which includes the light-emitting element including the iridium complex described in Embodiment 1 can be suitably used as an in-vehicle light-emitting device and an in-vehicle lighting device. Moreover, the light-emitting device and the lighting device can be mounted at low cost.

Figure 9A:
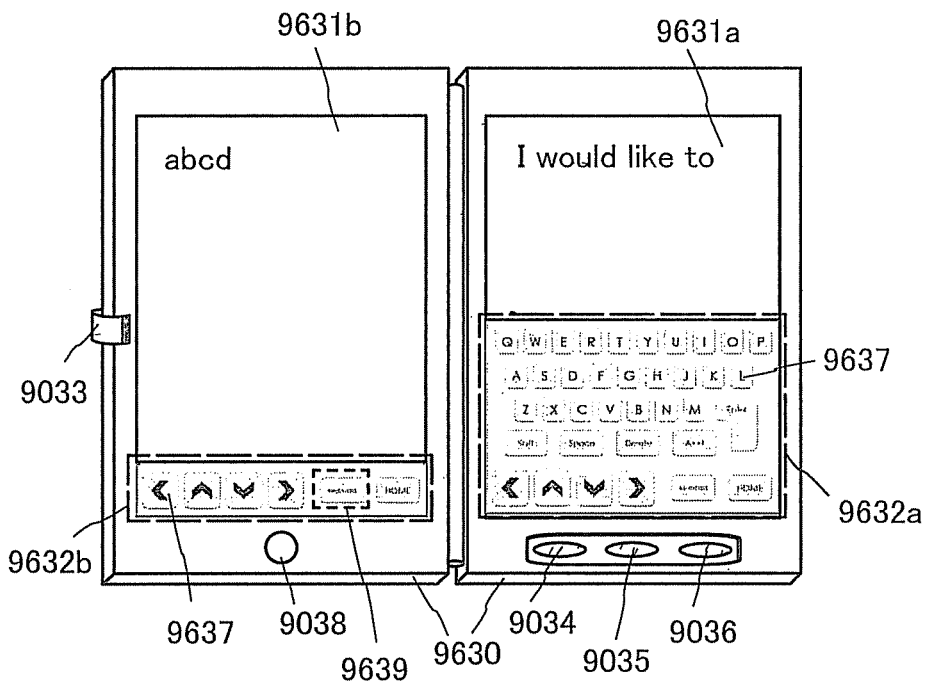
FIGS. 9A to 9C illustrate an example of an electronic device.
Figure 9B:
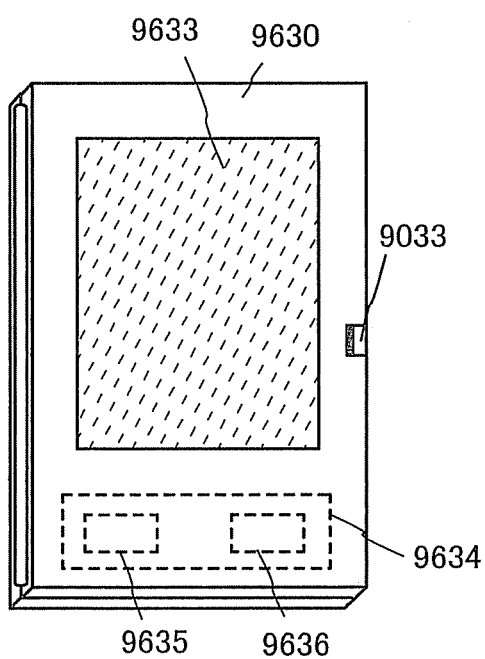

FIGS. 9A and 9B illustrate an example of a foldable tablet. FIG. 9A illustrates the tablet which is unfolded. The tablet includes a housing 9630, a display portion 9631*a*, a display portion 9631*b*, a display mode switch 9034, a power switch 9035, a power-saving mode switch 9036, a clasp 9033, and an operation switch 9038. Note that in the tablet, one or both of the display portion 9631*a* and the display portion 9631*b* is/are formed using a light-emitting device which includes a light-emitting element including the iridium complex described in Embodiment 1.

Part of the display portion 9631*a* can be a touchscreen region 9632*a* and data can be input when a displayed operation key 9637 is touched. Although half of the display portion 9631*a* has only a display function and the other half has a touchscreen function, one embodiment of the present invention is not limited to the structure. The whole display portion 9631*a* may have a touchscreen function. For example, a keyboard is displayed on the entire region of the display portion 9631*a* so that the display portion 9631*a* is used as a touchscreen; thus, the display portion 9631*b* can be used as a display screen.

Like the display portion 9631*a*, part of the display portion 9631*b* can be a touchscreen region 9632*b*. When a switching button 9639 for showing/hiding a keyboard on the touchscreen is touched with a finger, a stylus, or the like, the keyboard can be displayed on the display portion 9631*b*.

Touch input can be performed in the touchscreen region 9632*a* and the touchscreen region 9632*b* at the same time.

The display mode switch 9034 can switch the display between portrait mode, landscape mode, and the like, and between monochrome display and color display, for example. The power-saving mode switch 9036 can control display luminance in accordance with the amount of external light in use of the tablet detected by an optical sensor incorporated in the tablet. Another detection device including a sensor for detecting inclination, such as a gyroscope or an acceleration sensor, may be incorporated in the tablet, in addition to the optical sensor.

Although FIG. 9A illustrates an example in which the display portion 9631*a* and the display portion 9631*b* have the same display area, one embodiment of the present invention is not limited to the example. The display portion 9631*a* and the display portion 9631*b* may have different display areas and different display quality. For example, higher definition images may be displayed on one of the display portions 9631*a* and 9631*b*.

FIG. 9B illustrates the tablet which is folded. The tablet includes the housing 9630, a solar cell 9633, a charge and discharge control circuit 9634, a battery 9635, and a DC-to-DC converter 9636. As an example, FIG. 9B illustrates the charge and discharge control circuit 9634 including the battery 9635 and the DC-to-DC converter 9636.

Since the tablet is foldable, the housing 9630 can be closed when the tablet is not in use. As a result, the display portion 9631*a* and the display portion 9631*b* can be protected, thereby providing a tablet with high endurance and high reliability for long-term use.

The tablet illustrated in FIGS. 9A and 9B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar cell 9633 provided on a surface of the tablet can supply power to the touchscreen, the display portion, a video signal processing portion, or the like. Note that the solar cell 9633 is preferably provided on one or two surfaces of the housing 9630, in which case the battery 9635 can be charged efficiently.

Figure 9C:
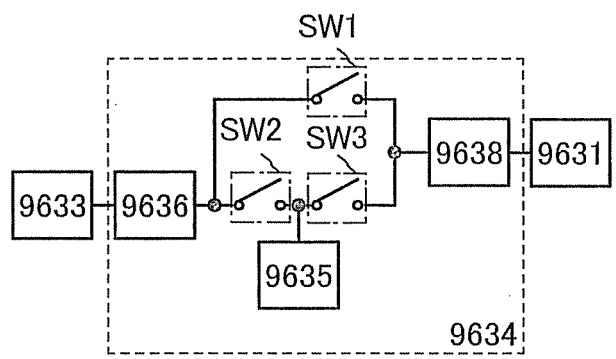

The structure and operation of the charge and discharge control circuit 9634 illustrated in FIG. 9B will be described with reference to a block diagram of FIG. 9C. FIG. 9C illustrates the solar cell 9633, the battery 9635, the DC-to-DC converter 9636, a converter 9638, switches SW1 to SW3, and the display portion 9631. The battery 9635, the DC-to-DC converter 9636, the converter 9638, and the switches SW1 to SW3 correspond to the charge and discharge control circuit 9634 illustrated in FIG. 9B.

First, description is made on an example of the operation in the case where power is generated by the solar cell 9633 with the use of external light. The voltage of the power generated by the solar cell is raised or lowered by the DC-to-DC converter 9636 so as to be voltage for charging the battery 9635. Then, when power from the solar cell 9633 is used for the operation of the display portion 9631, the switch SW1 is turned on and the voltage of the power is raised or lowered by the converter 9638 so as to be voltage needed for the display portion 9631. When images are not displayed on the display portion 9631, the switch SW1 is turned off and the switch SW2 is turned on so that the battery 9635 is charged.

Although the solar cell 9633 is described as an example of a power generation means, the power generation means is not particularly limited, and the battery 9635 may be charged by another power generation means such as a piezoelectric element or a thermoelectric conversion element (Peltier element). The battery 9635 may be charged by a non-contact power transmission module capable of performing charging by transmitting and receiving power wirelessly (without contact), or any of the other charge means used in combination, and the power generation means is not necessarily provided.

One embodiment of the present invention is not limited to the tablet having the shape illustrated in FIGS. 9A to 9C as long as the display portion 9631 is included.

EXAMPLE 1

Synthesis Example 1

In this example, a synthesis method of tris{2-[4-(1-adamantyl)-3-methyl-4H-1,2,4-triazol-5-yl-κN]phenyl-κC}-iridium(III) (abbreviation: [Ir(Mptz-Adm1)$_3$]) described in Embodiment 1 and represented by Structural Formula (101) will be described. The structure of. [Ir(Mptz-Adm1)$_3$] is shown below.

[Chemical formula 40]

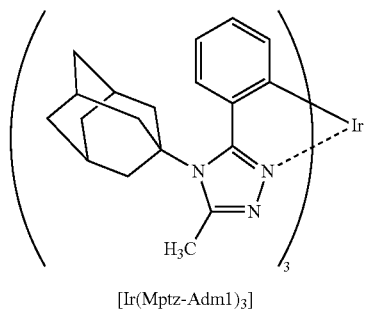

[Ir(Mptz-Adm1)$_3$]

Step 1: Synthesis of N-(1-Adamantyl)benzamide

In a 500-mL three-neck flask were put 15.0 g (80 mmol) of 1-adamantanamine hydrochloride, 16.2 g (160 mmol) of triethylamine, and 250 mL of tetrahydrofuran (THF), and the mixture was stirred. To this mixed solution, a mixed solution of 11.2 g (80 mmol) of benzoyl chloride and 50 mL of THF was added dropwise under cooling with ice, and the mixture was stirred at room temperature for 6 days. After the stirring, this mixture was dissolved in chloroform, and washed with water, a saturated aqueous solution of sodium hydrogen carbonate, and saturated brine. After the washing, the aqueous layer and the organic layer were separated, and anhydrous magnesium sulfate was added to the organic layer for drying. The obtained mixture was subjected to gravity filtration, and the filtrate was concentrated to give a solid. This solid was washed with a mixed solvent of ethyl acetate and hexane to give 15.0 g of a white solid in a yield of 73%.

The obtained white solid was identified as N-(1-adamantyl)benzamide by a nuclear magnetic resonance (NMR) method. A synthesis scheme of Step 1 is shown in (a-1).

[Chemical formula 41]

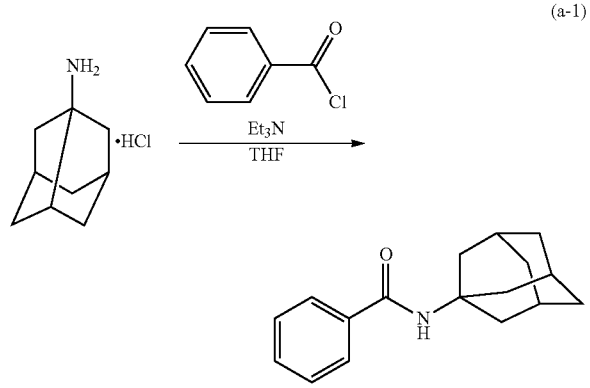

(a-1)

Step 2: Synthesis of N-(1-Adamantyl)benzenecarbothioamide

In a 500-mL three-neck flask were put 14.9 g (58 mmol) of N-(1-adamantyl)benzamide obtained in Step 1, 11.8 g (29 mmol) of 2,4-bis(4-methoxyphenyl)-1,3-dithia-2,4-diphosphetane 2,4-disulfide (Lawesson's reagent), and 120 mL of toluene, and the mixture was heated and refluxed at 120° C. for 7 hours. After the stirring, the precipitated solid was suction-filtered, and washed with toluene to give 12.5 g of a yellow solid in a yield of 79%. The obtained yellow solid was identified as N-(1-adamantyl)benzenecarbothioamide by $^1$H NMR measurement. A synthesis scheme of Step 2 is shown in (b-1).

[Chemical formula 42]

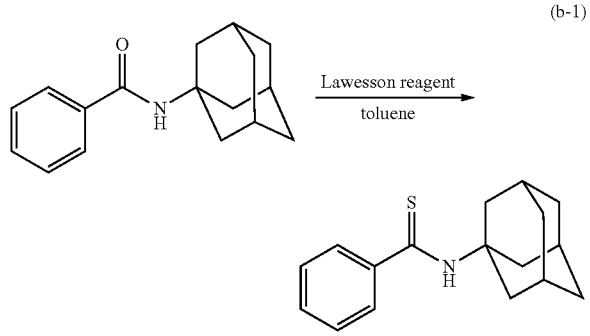

(b-1)

Step 3: Synthesis of N-[(Ethylsulfanyl)phenylmethylidene]-1-adamantanamine

In a 300-mL three-neck flask were put 3.1 g (46 mmol) of sodium ethoxide and 13 g (46 mmol) of N-(1-adamantyl)benzenecarbothioamide obtained in Step 2, 80 mL of ethanol was added thereto, and the mixture was stirred at room temperature for 3 hours. After the stirring, 3.7 mL of iodoethane was added to the mixture, and the mixture was stirred at 60° C. for 5 hours. After the stirring, 40 mL of ethanol was added to this mixture and the mixture was stirred at 60° C. for 9 hours. After the stirring, ethanol was distilled off to give a yellow solid. This yellow solid was dissolved in dichloromethane, and washed with water, a saturated aqueous solution of sodium hydrogen carbonate, and saturated brine. After the washing, the organic layer and the aqueous layer were separated, and anhydrous magnesium sulfate was added to the organic layer for drying. This mixture was subjected to gravity filtration and the obtained filtrate was concentrated to give 11 g of a yellow solid in a yield of 78%. It was confirmed by gas chromatography mass spectrometry (GC/MS) that the molecular weight of the yellow solid is 299, which is the same as that of N-[(ethylsulfanyl)phenylmethylidene]-1-adamantanamine, an objective substance. A synthesis scheme of Step 3 is shown in (c-1).

[Chemical formula 43]

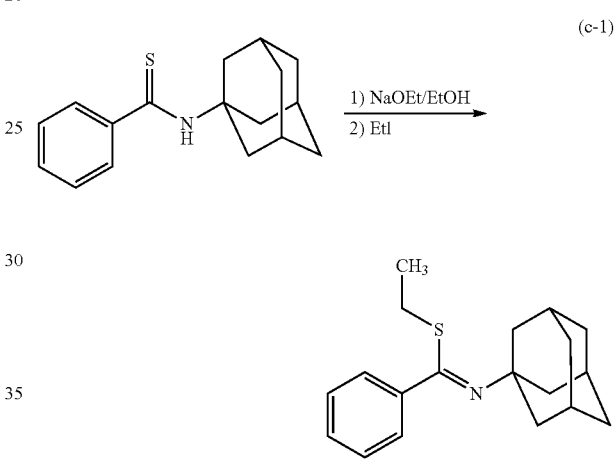

(c-1)

Step 4: Synthesis of 4-(1-Adamantyl)-3-methyl-5-phenyl-4H-1,2,4-triazole

In a 200-mL three-neck flask were put 5.4 g (18 mmol) of N-[(ethylsulfanyl)phenylmethylidene]-1-adamantanamine obtained in Step 3, 1.3 g (18 mmol) of acetohydrazide, and 30 mL of 1-butanol, and the mixture was heated and refluxed under a nitrogen stream at 130° C. for 16 hours. The reacted solution was concentrated to give a residue. This residue was purified by silica gel column chromatography. Ethyl acetate was used as a developing solvent. The obtained fraction was concentrated to give an oily substance. This oily substance was subjected to extraction with dichloromethane, and the obtained solution of the extract was washed with water and a saturated aqueous solution of sodium hydrogen carbonate. After the washing, anhydrous magnesium sulfate was added to the organic layer for drying. The obtained mixture was subjected to gravity filtration, and the filtrate was concentrated to give a white solid. A mixed solvent of ethyl acetate and hexane was added to this solid, and suction filtration was carried out to give 0.63 g of a white solid in a yield of 12%. The obtained white solid was identified as 4-(1-adamantyl)-3-methyl-5-phenyl-4H-1,2,4-triazole by $^1$H NMR measurement. A synthesis scheme of Step 4 is shown in (d-1).

[Chemical formula 44]

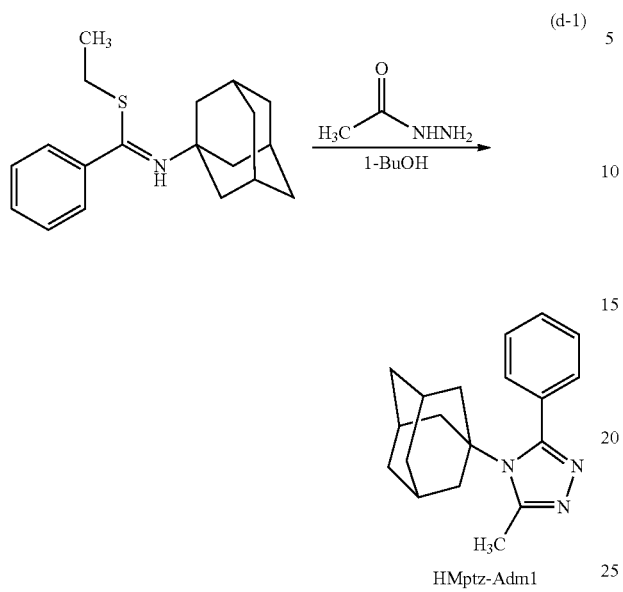

(d-1)

Step 5: Synthesis of Tris{2-[4-(1-adamantyl)-3-methyl-4H-1,2,4-triazol-5-yl-κN]phenyl-κC}iridium (III) (abbreviation: [Ir(Mptz-Adm1)₃])

In a reaction container equipped with a three-way cock were put 1.3 g (4.3 mmol) of 4-(1-adamantyl)-3-methyl-5-phenyl-4H-1,2,4-triazole and 0.420 g (0.859 mmol) of tris(acetylacetonato)iridium(III), and heating was performed at 250° C. for 84 hours. The obtained reaction mixture was dissolved in dichloromethane and purification by alumina column chromatography was performed. Dichloromethane was used as a developing solvent. The obtained fraction was concentrated to give a solid. A small amount of ethyl acetate was added to the obtained solid, and suction filtration was carried out to give 0.1 g of a white solid. Because the obtained solid contained impurities, purification by silica column chromatography was performed. As the developing solvent, a mixed solvent of dichloromethane and hexane in a ratio of 1:1 was used. The obtained fraction was concentrated to give a solid. A small amount of ethyl acetate was added to the obtained solid, and suction filtration was carried out to give 40 mg of a pale yellow solid in a yield of 4%. A synthesis scheme of Step 5 is shown in (e-1).

[Chemical formula 45]

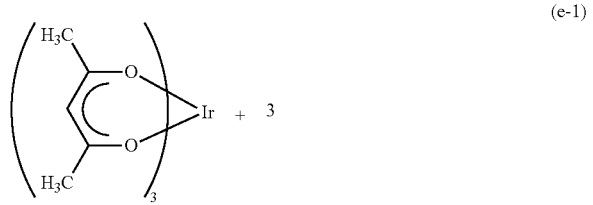

(e-1)

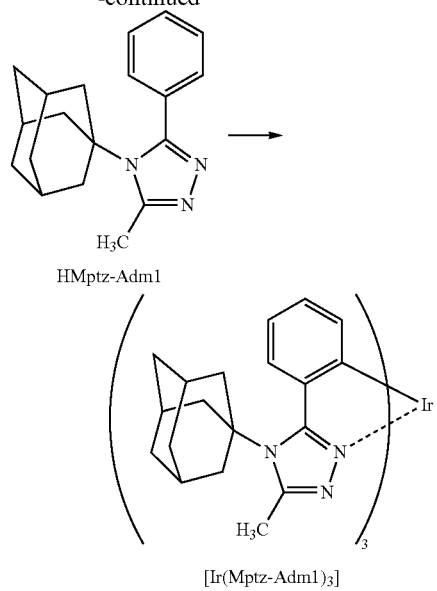

The obtained pale yellow solid was subjected to nuclear magnetic resonance (NMR) measurement. The measurement data are shown below.

$^1$H NMR. δ(CD₂Cl₂): 1.75 (br, 18H), 2.00 (s, 9H), 2.21-2.25 (br, 27H), 6.57 (d, 3H), 6.71 (t, 3H), 6.81 (t, 3H), 7.51 (d, 3H).

Figure 10A:
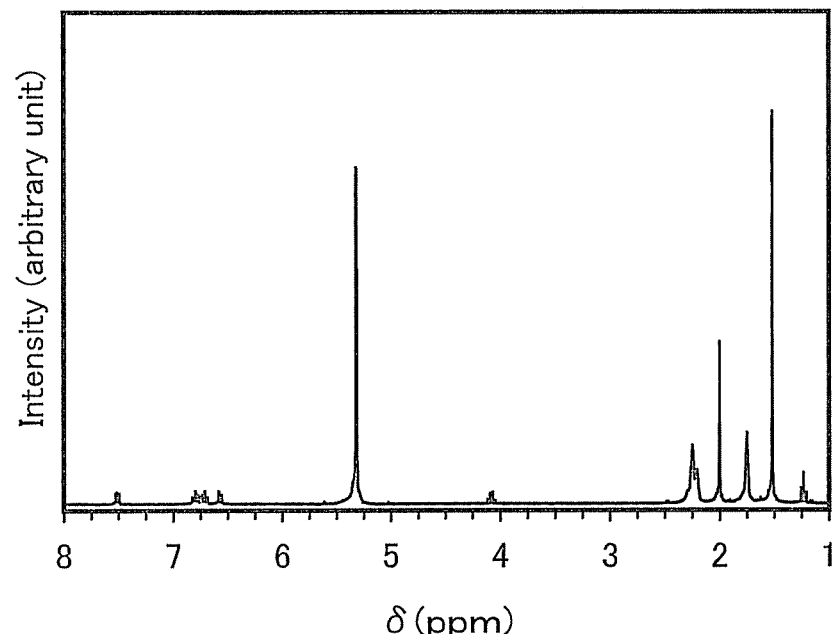
FIGS. 10A and 10B are $^1$H NMR charts of [Ir(Mptz-Adm1)$_3$], an iridium complex represented by Structural Formula (100).
Figure 10B:
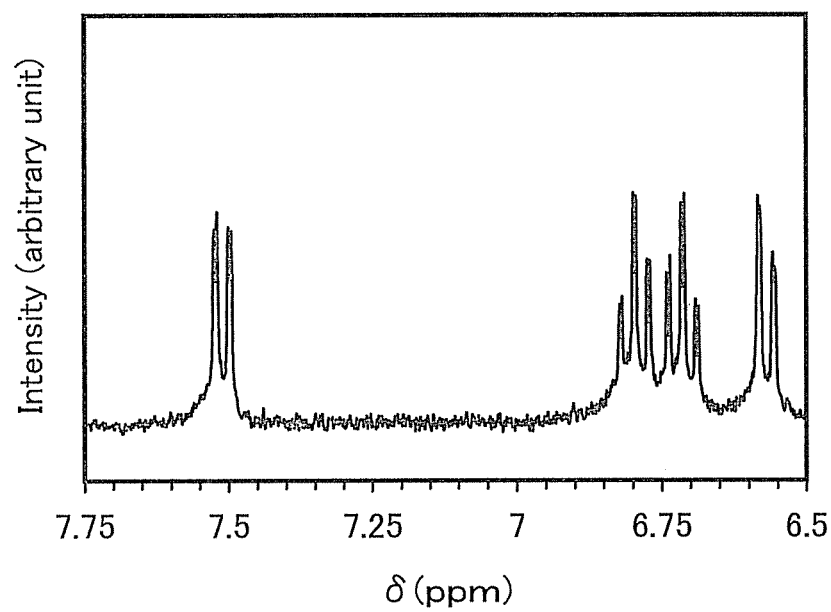

In addition, the $^1$H-NMR charts are shown in FIGS. 10A and 10B. FIG. 10B is an enlarged chart showing a range of 6.5 ppm to 7.75 ppm of FIG. 10A. The measurement results confirmed that [Ir(Mptz-Adm1)₃] that was the objective substance was obtained.

Then, thermogravimetry-differential thermal analysis (TG-DTA) was performed. The measurement was performed using a thermogravimetry/differential thermal analysis apparatus (TG/DTA-320, manufactured by Seiko Instruments Inc.). Accordingly, it was revealed that the 5% weight loss temperature (the temperature at which the weight becomes 95% of that at the start of the measurement) of [Ir(Mptz-Adm1)₃] was 473° C. under atmospheric pressure and 367° C. in high vacuum (a rate of temperature increase: 10° C./min).

Figure 11:
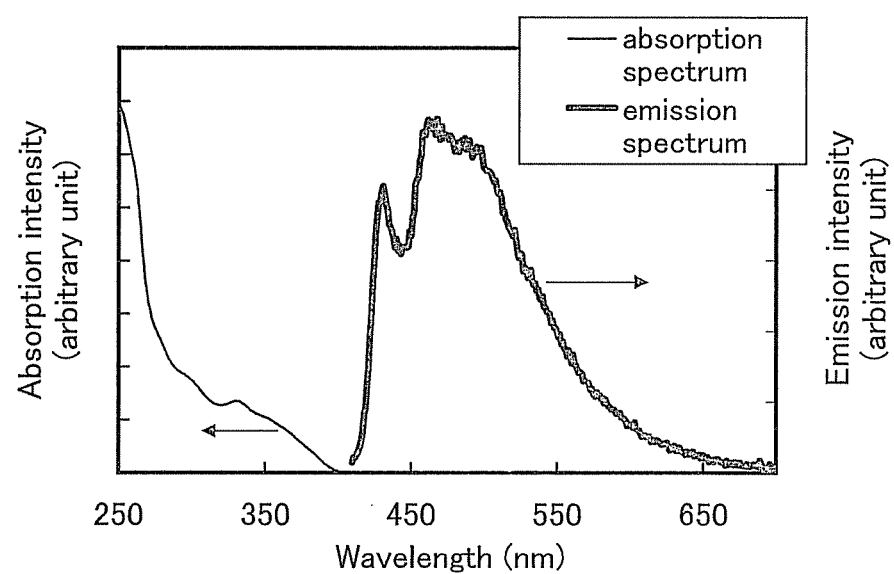
FIG. 11 shows an ultraviolet-visible absorption spectrum and an emission spectrum of [Ir(Mptz-Adm1)$_3$], an iridium complex represented by Structural Formula (100), in a dichloromethane solution of [Ir(Mptz-Adm1)$_3$].

Next, an ultraviolet-visible absorption spectrum (hereinafter, simply referred to as absorption spectrum) and an emission spectrum of a dichloromethane solution of [Ir(Mptz-Adm1)₃] were measured. The absorption spectrum was measured with the use of an ultraviolet-visible light spectrophotometer (V-550, manufactured by JASCO Corporation) in the state where the dichloromethane solution (0.11 mmol/L) was put in a quartz cell at room temperature. The emission spectrum was measured with the use of a fluorescence spectrophotometer (F5920, manufactured by Hamamatsu Photonics Corporation) in the state where the degassed dichloromethane solution (0.11 mmol/L) was put in a quartz cell at room temperature. FIG. 11 shows measurement results of the absorption spectrum and the emission spectrum. The horizontal axis represents wavelength and the vertical axes represent absorption intensity and emission intensity. Note that the absorption spectrum in FIG. 11 is a result obtained by subtraction of a measured absorption spectrum of only dichloromethane that was put in a quartz cell from the measured absorption spectrum of the dichloromethane solution (0.11 mmol/L) in a quartz cell.

As shown in FIG. 11, [Ir(Mptz-Adm1)₃], the iridium complex of one embodiment of the present invention, has emission peaks at 431 nm and 464 nm, and green light was observed from the dichloromethane solution.

EXAMPLE 2

Synthesis Example 2

In this example, a synthesis method of tris{2-[4-(2-adamantyl)-3-methyl-4H-1,2,4-triazol-5-yl-κN]phenyl-κC}iridium(III) (abbreviation: [Ir(Mptz-Adm2)₃]) represented by Structural Formula (100) in Embodiment 1 will be described. The structure of [Ir(Mptz-Adm2)₃] is shown below.

[Chemical formula 46]

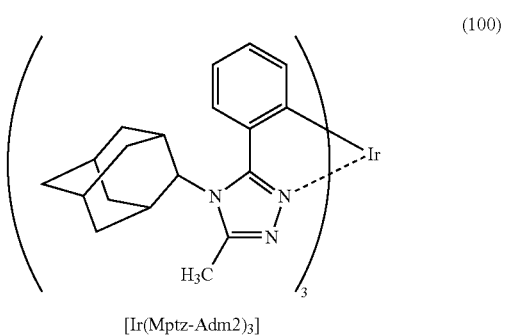

[Ir(Mptz-Adm2)₃]

Step 1: Synthesis of N-(2-Adamantyl)benzamide

First, 60.0 g (321 mmol) of 2-adamantanamine hydrochloride that is a raw material was divided into three 20-g batches and was reacted as follows. In a 500-mL three-neck flask were put 20.0 g (107 mmol) of 2-adamantanamine hydrochloride, 21.7 g (214 mmol) of triethylamine, and 300 mL of tetrahydrofuran (THF), and the mixture was stirred. To this mixed solution, a mixed solution of 15.0 g (107 mmol) of benzoyl chloride and 50 mL of THF was added dropwise under cooling with ice, and the mixture was stirred at room temperature for 24 hours. After the stirring, three batches of the reacted solution were poured into 400 mL of water and the mixture was stirred for 30 minutes. After the stirring, 1 L of chloroform was added and the organic layer and the aqueous layer were separated. The organic layer was washed with water, a saturated 20, aqueous solution of sodium hydrogen carbonate, and saturated brine. After the washing, the organic layer and the aqueous layer were separated, and anhydrous magnesium sulfate was added to the organic layer for drying. The obtained mixture was subjected to gravity filtration, and the filtrate was concentrated to give a solid. A small amount of hexane was added to this solid, and suction filtration was carried out to give 77.8 g of a white solid in a yield of 95%. The obtained white solid was identified as N-(2-adamantyl)benzamide by a nuclear magnetic resonance (NMR) method. A synthesis scheme of Step 1 is shown in (a-2).

[Chemical formula 47]

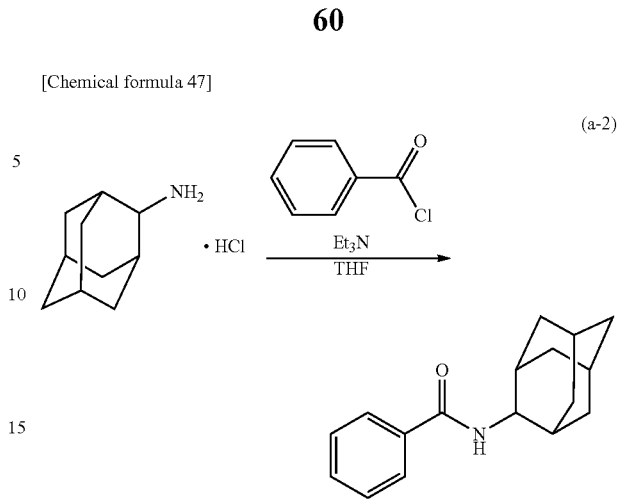

Step 2: Synthesis of N-(2-Adamantyl)benzenecarbothioamide

In a 500-mL three-neck flask were put 16.0 g (64 mmol) of N-(2-adamantyl)benzamide obtained in Step 1, 13.0 g (32 mmol) of 2,4-bis(4-methoxyphenyl)-1,3-dithia-2,4-diphosphetane 2,4-disulfide (Lawesson's reagent), and 100 mL of toluene, and the mixture was heated and refluxed at 120° C. for 8 hours. After the heating and refluxing, this reacted solution was purified by silica gel column chromatography using toluene as a developing solvent. The obtained fraction was concentrated to give a yellow solid. The obtained solid was recrystallized with toluene, so that 14 g of a yellow solid, which was an objective substance, was obtained in a yield of 80%. The obtained yellow solid was identified as N-(2-adamantyl)benzenecarbothioamide by a nuclear magnetic resonance (NMR) method. A synthesis scheme of Step 2 is shown in (b-2).

[Chemical formula 48]

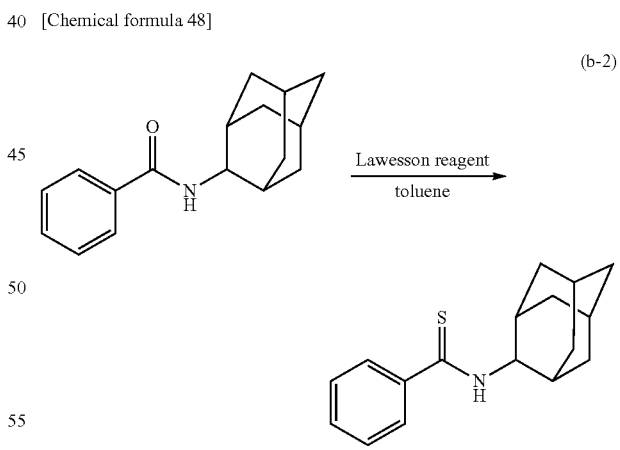

Step 3: Synthesis of N-[(Ethylsulfanyl)phenylmethylidene]-2-adamantanamine)

In a 500-mL three-neck flask were put 8.4 g (124 mmol) of sodium ethoxide and 33.5 g of N-(2-adamantyl)benzenecarbothioamide synthesized in Step 2, 200 mL of ethanol was added thereto, and the mixture was stirred at room temperature for 12 hours. After the stirring, 10.0 mL of iodoethane was added to the mixture, and the mixture was stirred at 60° C. for 8 hours. After the stirring, ethanol was distilled off to give a yellow solid. This solid was dissolved in dichloromethane, and washed with water, a saturated aqueous solution of sodium hydrogen carbonate, and saturated brine. After the washing, the organic layer and the aqueous layer were separated, and anhydrous magnesium sulfate was added to the organic layer for drying. This mixture was subjected to gravity filtration and the obtained filtrate was concentrated to give 34.2 g of a yellow solid in a yield of 92%. It was confirmed by gas chromatography mass spectrometry (GC/MS) that the molecular weight of the yellow solid is 299, which is the same as that of N-[(ethylsulfanyl)phenylmethylidene]-2-adamantanamine, an objective substance. A synthesis scheme of Step 3 is shown in (c-2).

[Chemical formula 49]

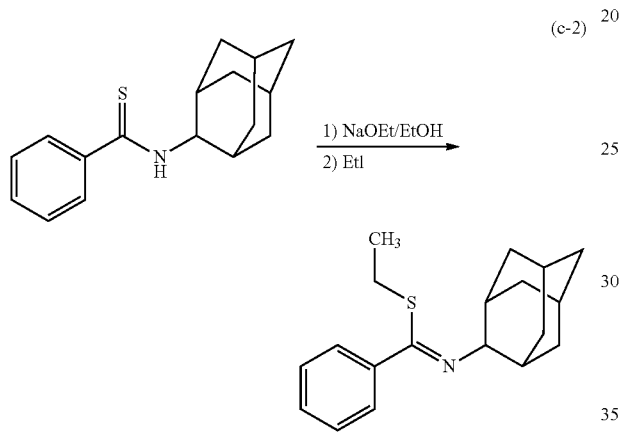

Step 4: Synthesis of 4-(2-Adamantyl)-3-methyl-5-phenyl-4H-1,2,4-triazole

In a 500-mL three-neck flask were put 34.2 g (117 mmol) of N-[(ethylsulfanyl)phenylmethylidene]-2-adamantanamine synthesized in Step 3, 8.6 g (117 mmol) of acetohydrazide, and 90 mL of 1-butanol, and the mixture was heated and refluxed under a nitrogen stream at 130° C. for 26 hours. The reacted solution was concentrated to give a solid. This solid was purified by silica gel column chromatography. Ethyl acetate was used as a developing solvent. The obtained fraction was concentrated to give an oily substance. This oily substance was subjected to extraction with dichloromethane, and the obtained solution of the extract was washed with water and a saturated aqueous solution of sodium hydrogen carbonate. After the washing, the organic layer and the aqueous layer were separated, and anhydrous magnesium sulfate was added to the organic layer for drying. The obtained mixture was subjected to gravity filtration, and the filtrate was concentrated to give a white solid. A mixed solvent of ethyl acetate and hexane was added to this solid, and suction filtration was carried out to give 4.1 g of a white solid in a yield of 12%. The obtained white solid was identified as 4-(2-adamantyl)-3-methyl-5-phenyl-4H-1,2,4-triazole by a nuclear magnetic resonance (NMR) method. A synthesis scheme of Step 4 is shown in (d-2).

[Chemical formula 50]

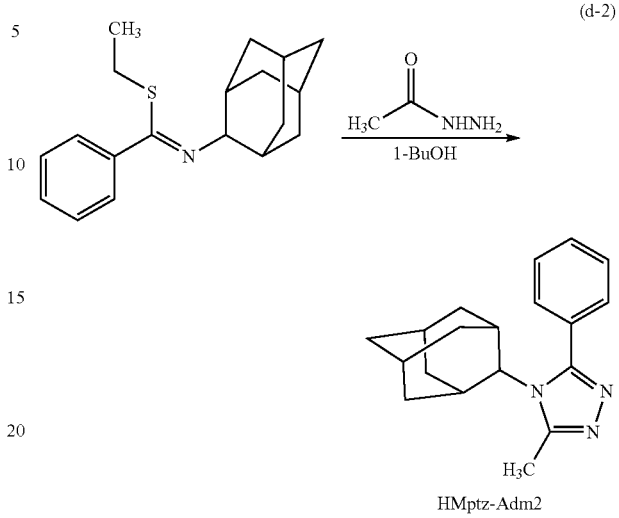

Step 5: Synthesis of Tris{2-[4-(2-adamantyl)-3-methyl-4H-1,2,4-triazol-5-yl-κN]phenyl-κC}iridium (III) (abbreviation: [Ir(Mptz-Adm2)₃])

In a reaction container equipped with a three-way cock were put 4.1 g (14.0 mmol) of 4-(2-adamantyl)-3-methyl-5-phenyl-4H-1,2,4-triazole and 1.37 g (2.8 mmol) of tris(acetylacetonato)iridium(III), and heating was performed at 250° C. for 48 hours. The obtained reaction mixture was dissolved in dichloromethane and purification by silica column chromatography (neutral silica) was performed. As the developing solvent, a mixed solvent of dichloromethane and hexane in a ratio of 1:1 was used. The obtained fraction was concentrated to give a solid. The obtained solid was recrystallized with ethyl acetate to give 78 mg of a yellow solid in a yield of 3%. A synthesis scheme of Step 5 is shown in (e-2).

[Chemical formula 51]

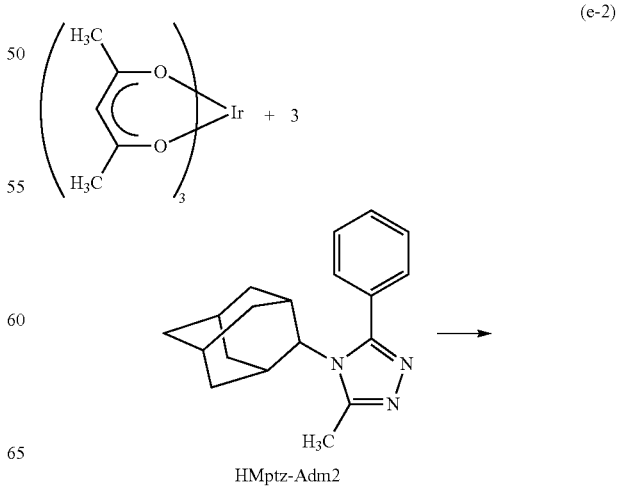

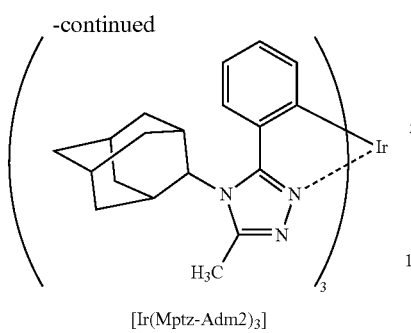

[Ir(Mptz-Adm2)₃]

The obtained yellow solid was subjected to nuclear magnetic resonance (NMR) measurement. The measurement data are shown below.

¹H-NMR. δ(CDCl₃): 1.60-1.64 (br, 6H), 1.71 (s, 9H), 1.80 (br, 6H), 1.93-2.01 (br, 18H), 2.17-2.21 (br, 3H), 2.36-2.41 (br, 6H), 2.61-2.66 (br, 3H), 4.90 (br, 3H), 6.68 (d, 3H), 6.77 (t, 3H), 6.88 (t, 3H), 7.31 (d, 3H).

Figure 12A:
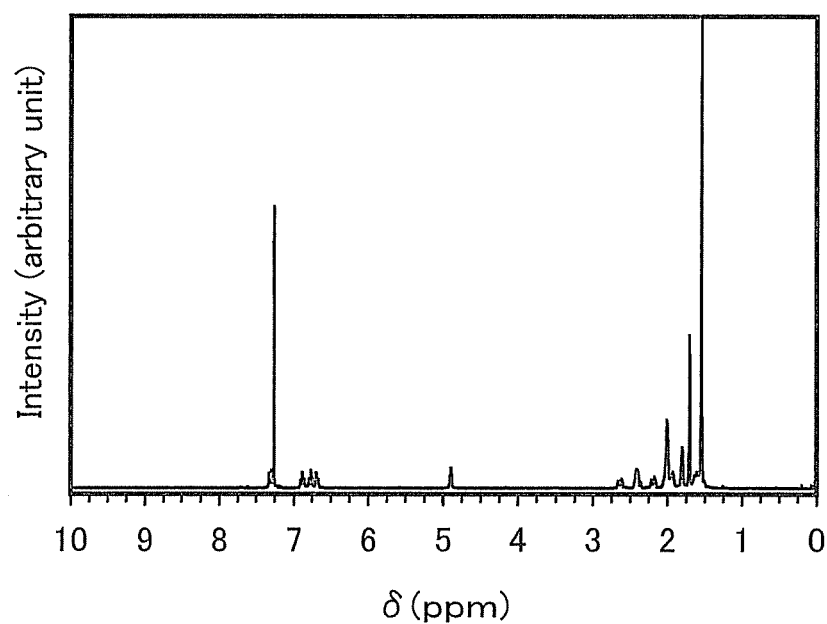
FIGS. 12A and 12B are $^1$H NMR charts of [Ir(Mptz-Adm2)$_3$], an iridium complex represented by Structural Formula (101).
Figure 12B:
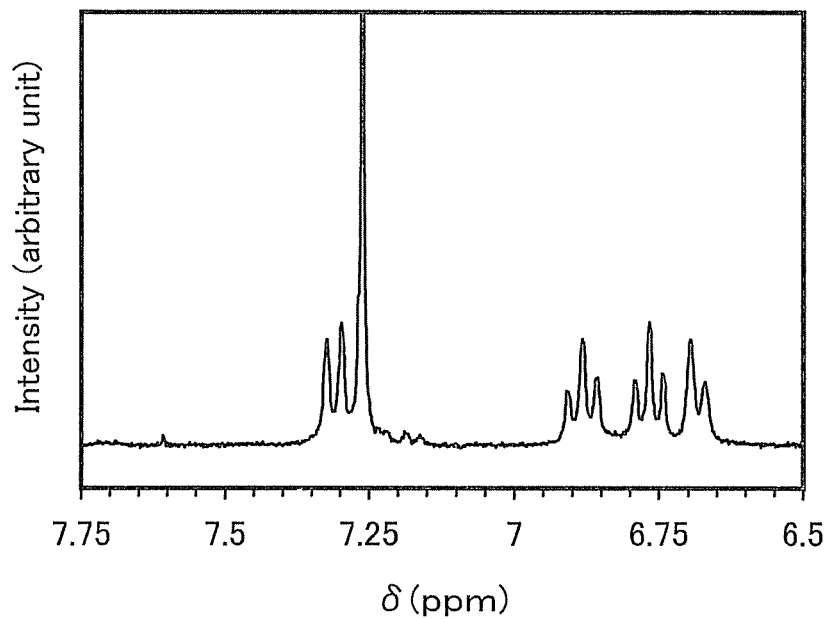

In addition, the ¹H-NMR charts are shown in FIGS. 12A and 12B. FIG. 12B is an enlarged chart showing a range of 6.5 ppm to 7.75 ppm of FIG. 12A. The measurement results confirmed that [Ir(Mptz-Adm2)₃] (abbreviation) that was the objective substance was obtained.

Then, thermogravimetry-differential thermal analysis (TG-DTA) was performed. The measurement was performed using a thermogravimetry/differential thermal analysis apparatus (TG/DTA-320, manufactured by Seiko Instruments Inc.). Accordingly, it was revealed that the 5% weight loss temperature (the temperature at which the weight becomes 95% of that at the start of the measurement) of [Ir(Mptz-Adm2)₃] was 312° C. under atmospheric pressure and 275° C. in high vacuum (a rate of temperature increase: 10° C./min). The results showed that [Ir(Mptz-Adm2)₃] is a material having high heat resistance and a moderate sublimation property.

Figure 13:
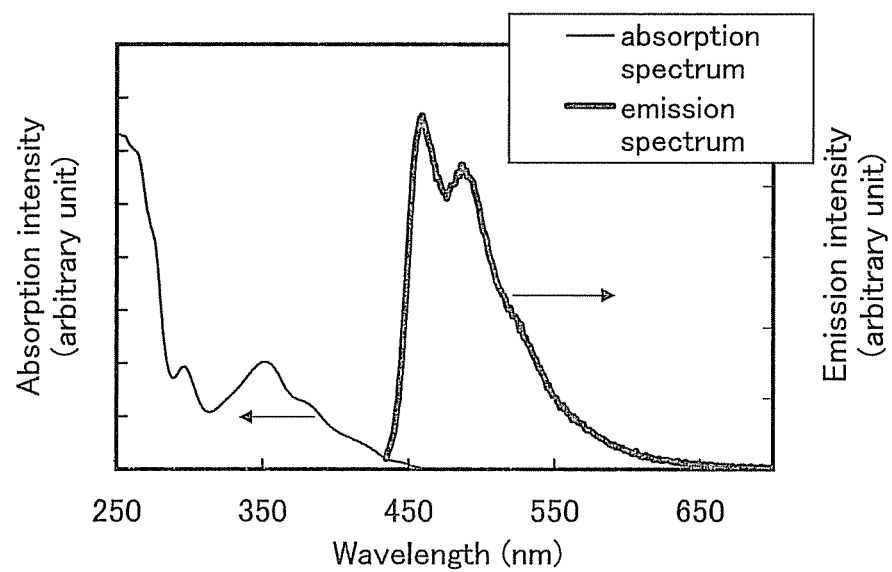
FIG. 13 shows an ultraviolet-visible absorption spectrum and an emission spectrum of [Ir(Mptz-Adm2)$_3$], an iridium complex represented by Structural Formula (101), in a dichloromethane solution of [Ir(Mptz-Adm2)$_3$].

Next, an ultraviolet-visible absorption spectrum (hereinafter, simply referred to as absorption spectrum) and an emission spectrum of a dichloromethane solution of [Ir(Mptz-Adm2)₃] were measured. The absorption spectrum was measured with the use of an ultraviolet-visible light spectrophotometer (V-550, manufactured by JASCO Corporation) in the state where the dichloromethane solution (0.13 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.13 mmol/L) was put in a quartz cell at room temperature. FIG. 13 shows measurement results of the absorption spectrum and the emission spectrum. The horizontal axis represents wavelength and the vertical axes represent absorption intensity and emission intensity. Note that the absorption spectrum in FIG. 13 is a result obtained by subtraction of a measured absorption spectrum of only dichloromethane that was put in a quartz cell from the measured absorption spectrum of the dichloromethane solution (0.13 mmol/L) in a quartz cell.

As shown in FIG. 13, [Ir(Mptz-Adm2)₃], the iridium complex described in Embodiment 1, has emission peaks at 459 nm and 487 nm, and blue light was observed from the dichloromethane solution.

As described above, [Ir(Mptz-Adm2)₃] synthesized in this example, the iridium complex described in Embodiment 1, is a light-emitting substance which emits blue phosphorescence. Note that the yield in the case of complex formation of tris(4,5-dimethyl-3-phenyl-4H-1,2,4-triazolato)iridium(III) (abbreviation: [Ir(Mptz-Me)₃]), a substance in which the adamantyl group of the ligand of [Ir(Mptz-Adm2)₃] is substituted with a methyl group, was rather poor.

Example 3

In this example, a light-emitting element was fabricated which includes tris{2-[4-(2-adamantyl)-3-methyl-4H-1,2,4-triazol-5-yl-κN]phenyl-κC}iridium(III) (abbreviation: [Ir(Mptz-Adm2)₃]), the iridium complex described in Embodiment 1, as an emission center substance. Shown below are molecular structures of organic compounds used in this example.

[Chemical formula 52]

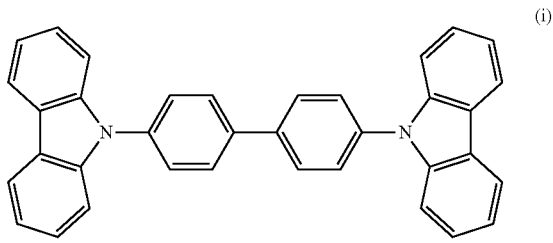

CBP (i)

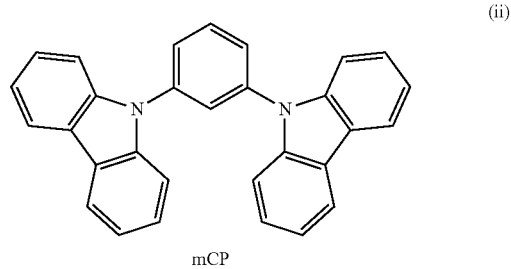

mCP (ii)

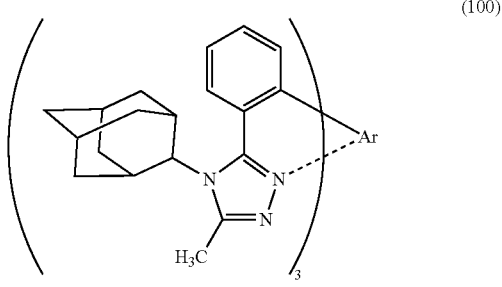

[Ir(Mptz-Adm2)₃]

(100)

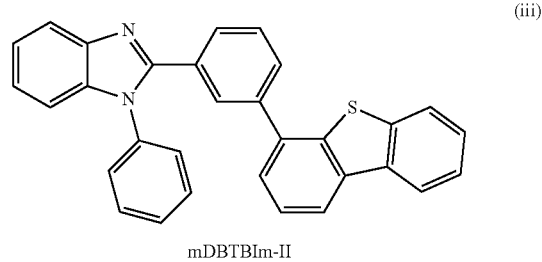

mDBTBIm-II (iii)

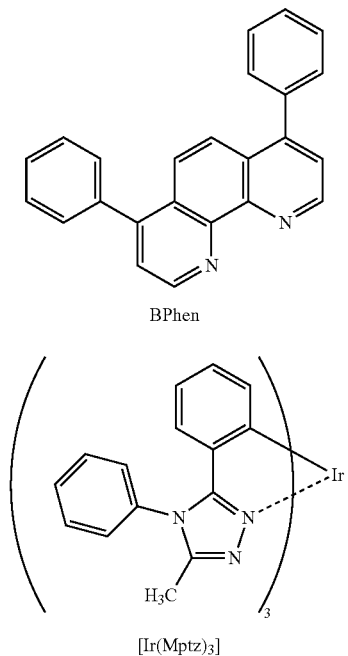

BPhen (iv)

[Ir(Mptz)₃] (v)

<<Fabrication of Light-Emitting Element 1 and Comparative Light-Emitting Element 1>>

First, a glass substrate, over which a film of indium tin oxide containing silicon (ITSO) was formed to a thickness of 110 nm as the first electrode 101, was prepared. A surface of the ITSO was covered with a polyimide film so that an area of 2 mm×2 mm of the surface was exposed. As pretreatment for forming the light-emitting element over the substrate, the surface of the substrate was washed with water and baked at 200° C. for 1 hour, and then a UV ozone treatment was performed for 370 seconds. Then, the substrate was transferred into a vacuum evaporation apparatus where the pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed to a holder provided in the vacuum evaporation apparatus such that the surface of the substrate over which the first electrode 101 was formed faced downward.

After the pressure in the vacuum evaporation apparatus was reduced to $10^{-4}$ Pa, 4,4'-bis(N-carbazolyl)biphenyl (abbreviation: CBP), which is represented by Structural Formula (i), and molybdenum(VI) oxide were co-evaporated so that the weight ratio of CBP to molybdenum oxide was 2:1; thus, the hole-injection layer 111 was formed. The thickness thereof was set to 60 nm. Note that the co-evaporation is an evaporation method in which a plurality of different substances are concurrently vaporized from the respective different evaporation sources.

Next, 1,3-bis(N-carbazolyl)benzene (abbreviation: mCP) which is represented by Structural Formula (ii) was deposited by evaporation to a thickness of 20 nm, so that the hole-transport layer 112 was formed.

Further, the light-emitting layer 113 was formed over the hole-transport layer 112 by forming a stacked layer in such a way that mCP and tris{2-[4-(2-adamantyl)-3-methyl-4H-1,2,4-triazol-5-yl-κN]phenyl-κC}iridium(III) (abbreviation: [Ir(Mptz-Adm2)₃]) represented by Structural Formula (100), which is one of the iridium complexes in Embodiment 1, were deposited by evaporation to a thickness of 30 nm so that the weight ratio of mCP to [Ir(Mptz-Adm2)₃] was 1:0.06, and thereover, 2-[3-(dibenzothiophen-4-yl)phenyl]-1-phenyl-1H-benzimidazole (abbreviation: mDBTBIm-II) represented by Structural. Formula (iii) and [Ir(Mptz-Adm2)₃] were deposited by evaporation to a thickness of 10 nm so that the weight ratio of mDBTBIm-II to [Ir(Mptz-Adm2)₃] was 1:0.06.

Next, bathophenanthroline (abbreviation: BPhen) represented by Structural Formula (iv) was deposited by evaporation to a thickness of 15 nm, so that the electron-transport layer 114 was formed.

Further, lithium fluoride was deposited by evaporation to a thickness of 1 nm over the electron-transport layer 114, so that the electron-injection layer 115 was formed. Lastly, an aluminum film was formed to a thickness of 200 nm as the second electrode 103 functioning as a cathode. Thus, the light-emitting element 1 was completed.

In fabrication of the comparative light-emitting element 1, [Ir(Mptz-Adm2)₃] used for the light-emitting layer 113 of the light-emitting element 1 was substituted with tris(5-methyl-3,4-diphenyl-4H-1,2,4-triazolato)iridium(III) (abbreviation: [Ir(Mptz)₃]), an iridium complex represented by Structural Formula (v). [Ir(Mptz)₃] is a substance in which the adamantyl group of the ligand of [Ir(Mptz-Adm2)₃] is substituted with a phenyl group.

Note that in the above evaporation processes, evaporation was all performed by a resistance heating method.

The element structures of the completed light-emitting elements are shown below.

TABLE 1

| | Functional Layer | | | | | |
|---|---|---|---|---|---|---|
| | Hole-injection Layer | Hole-transport Layer | Light-emitting Layer Thickness | | Electron-transport Layer | Electron-injection Layer |
| | 60 nm | 20 nm | 30 nm | 10 nm | 15 nm | 1 nm |
| Light-emitting Element 1 | CBP:MoOx (4:2) | mCP | mCP:Ir (Mptz-Adm2)₃ (1:0.06) | mDBTBIm-II:Ir (Mptz-Adm2)₃ (1:0.06) | BPhen | LiF |
| Comparative Light-emitting Element 1 | CBP:MoOx (4:2) | mCP | mCP:Ir (Mptz)₃ (1:0.06) | mDBTBIm-II:Ir (Mptz)₃ (1:0.06) | BPhen | LiF |

<<Operation Characteristics of Light-Emitting Elements>>

The light-emitting elements thus obtained were sealed in a glove box under a nitrogen atmosphere without being exposed to the air. Then, the operation characteristics of these light-emitting elements were measured. Note that the measurements were carried out at room temperature (in an atmosphere kept at 25° C.).

Figure 14:
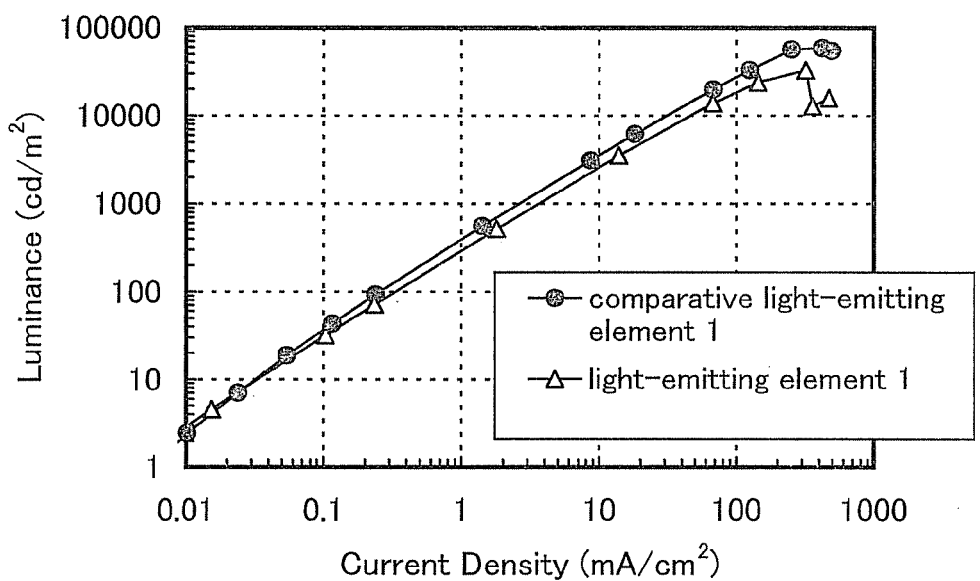
FIG. 14 shows current density-luminance characteristics of light-emitting elements fabricated in Example 4.
Figure 15:
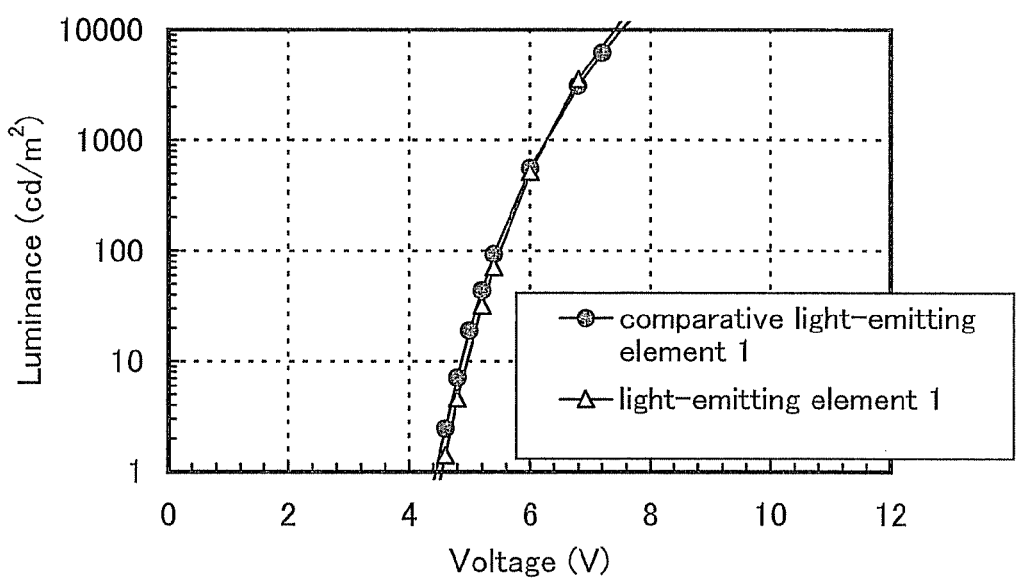
FIG. 15 shows voltage-luminance characteristics of light-emitting elements fabricated in Example 4.
Figure 16:
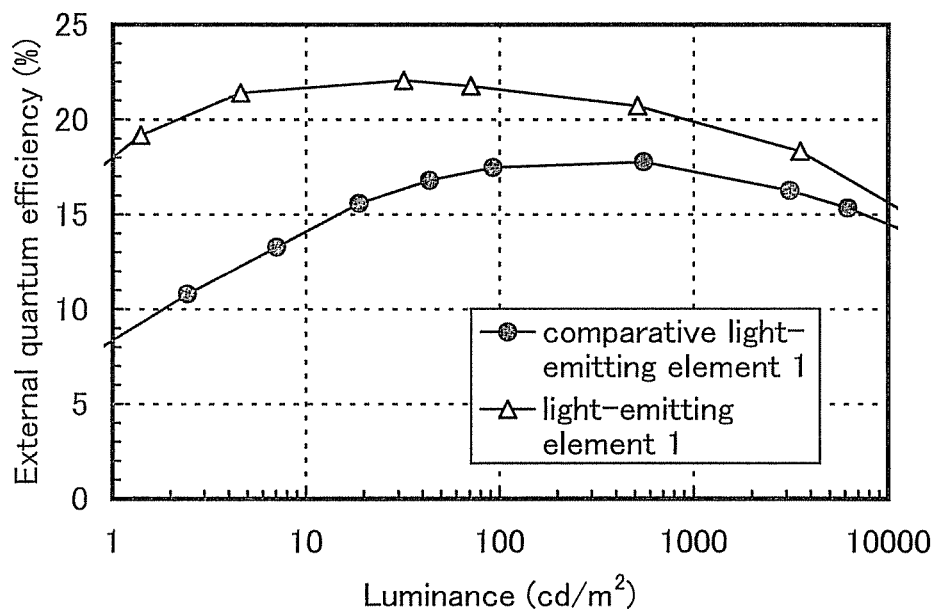
FIG. 16 shows luminance-external quantum efficiency characteristics of light-emitting elements fabricated in Example 4.
Figure 17:
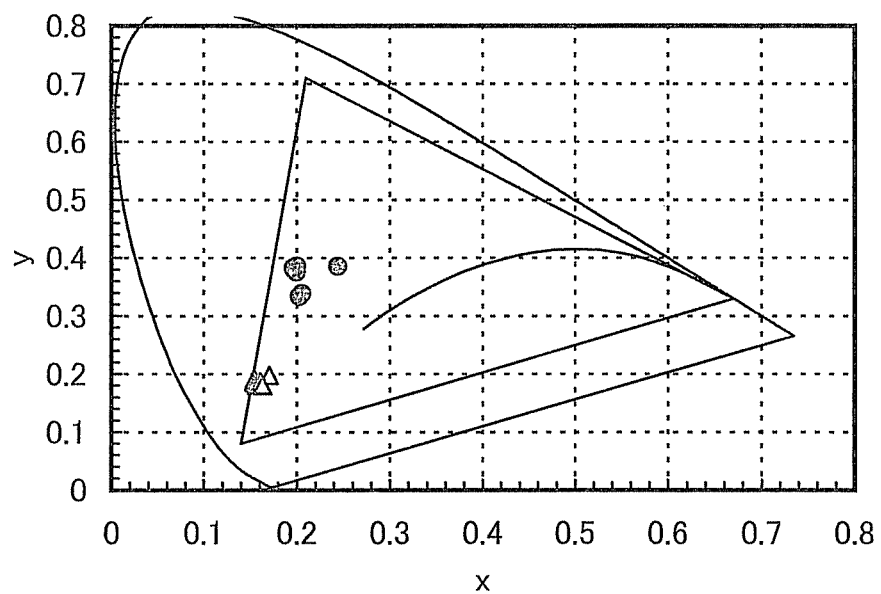
FIG. 17 shows chromaticity characteristics of light-emitting elements fabricated in Example 4.

FIG. 14 shows current density-luminance characteristics of the light-emitting element 1 and the comparative light-emitting element 1, FIG. 15 shows voltage-luminance characteristics of the light-emitting element 1 and the comparative light-emitting element 1, and FIG. 16 shows luminance-external quantum efficiency characteristics of the light-emitting element 1 and the comparative light-emitting element 1. In FIG. 14, the vertical axis represents luminance (cd/m$^2$) and the horizontal axis represents current density (mA/cm$^2$). In FIG. 15, the vertical axis represents luminance (cd/m$^2$) and the horizontal axis represents voltage (V). In FIG. 16, the vertical axis represents external quantum efficiency (%) and the horizontal axis represents luminance (cd/m$^2$). Further, chromaticity characteristics are shown in FIG. 17, in which chromaticities at points of measurement are plotted in chromaticity coordinates. In FIG. 17, ● (a dot) indicates the chromaticity of the comparative light-emitting element 1 and Δ (a triangle) indicates the chromaticity of the light-emitting element 1.

FIG. 14 and FIG. 15 show the favorable luminance-current efficiency characteristics and voltage-luminance characteristics of the light-emitting element 1 and the comparative light-emitting element 1 of this example. Thus, the elements were found to have high emission efficiency. In addition, FIG. 16 shows that the light-emitting element 1 has much higher external quantum efficiency than the comparative light-emitting element 1.

Figure 18:
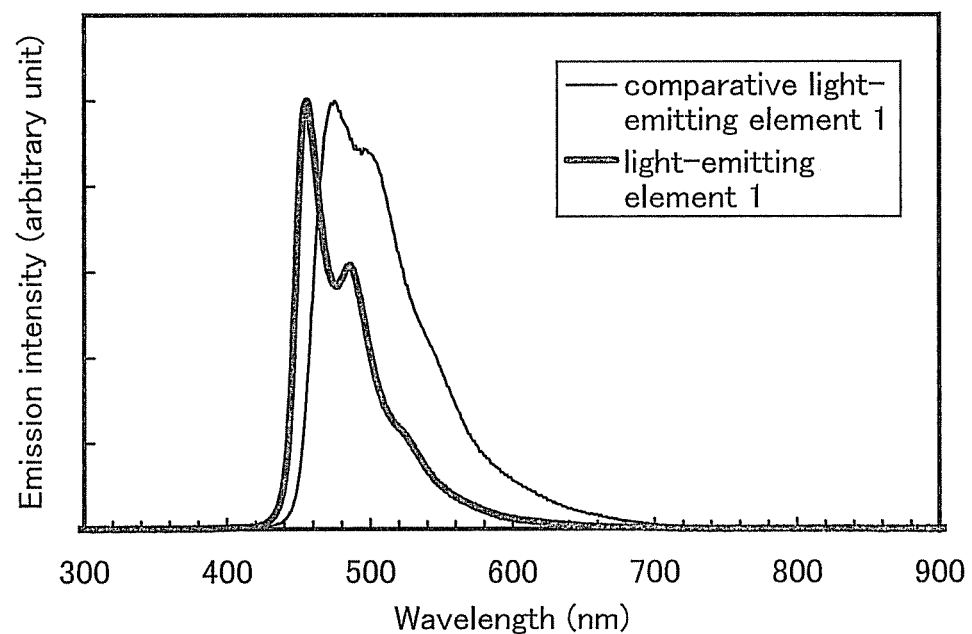
FIG. 18 shows emission spectra of light-emitting elements fabricated in Example 4.

FIG. 18 shows an emission spectrum when a current of 0.1 mA was made to flow in the fabricated light-emitting elements. In FIG. 18, the vertical axis represents emission intensity (arbitrary unit), and the horizontal axis represents wavelength (nm). The emission intensity is shown as a value relative to the greatest emission intensity assumed to be 1. FIG. 18 shows that the light-emitting element 1 of this example emits blue light with a maximum emission wavelength at around 457 nm, and the comparative light-emitting element 1 emits blue green light with a maximum emission wavelength at around 479 nm. The light-emitting element 1 has a shorter emission peak wavelength and a half width of the emission peak is smaller making the spectrum sharp. Thus, favorable blue light emission was obtained. The reason for this is that in [Ir(Mptz-Adm2)$_3$] in which the substituent bonded to the 4-position of the ligand is an adamantyl group, conjugation is less extended than in [Ir(Mptz)$_3$] in which the substituent is a phenyl group, so that the emission-wavelength extension was suppressed in [Ir(Mptz-Adm2)$_3$].

FIG. 17 also shows that the light-emitting element 1 emits more favorable blue light than the comparative light-emitting element 1.

From the above, it was found that the light-emitting element 1 using [Ir(Mptz-Adm2)$_3$] that is the iridium complex described in Embodiment 1 is a light-emitting element which has favorable emission efficiency and is capable of emitting favorable blue light.

EXAMPLE 4

Synthesis Example 3

In this example, a synthesis method of tris{2-[1-(2-adamantyl)-1H-benzimidazol-2-yl-κN3]phenyl-κC}iridium (III) (abbreviation: [Ir(pbi-Adm2)$_3$]) represented by Structural Formula (136) in Embodiment 1 will be described. The structure of [Ir(pbi-Adm2)$_3$] is shown below.

[Chemical formula 53]

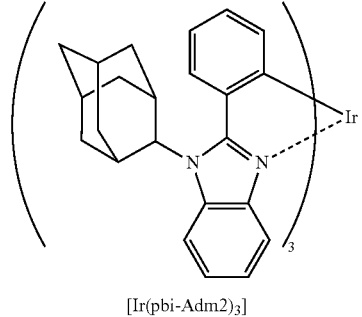

[Ir(pbi-Adm2)$_3$]

Step 1: Synthesis of N-(2-Adamantyl)-2-nitroaniline

In a 500-ml three-neck flask were put 10.0 g (53.3 mmol) of 2-adamantanamine hydrochloride, 34.7 g (106.5 mmol) of cesium carbonate, 150 ml of dimethyl sulfoxide (DMSO), and 7.5 g (53.3 mmol) of 2-fluoronitrobenzene, and the mixture was stirred under a nitrogen stream at room temperature for 24 hours. After the stirring, water was added to this reactant and the aqueous layer was subjected to extraction with chloroform. The obtained solution of the extract combined with the organic layer was washed with water and saturated brine, followed by drying with magnesium sulfate. The obtained mixture was subjected to gravity filtration, and the filtrate was concentrated to give an orange solid. Hexane was added to this solid and suction filtration was performed to give 10.6 g of an orange solid in a yield of 73%. The obtained orange solid was identified as N-(2-adamantyl)-2-nitroaniline by a nuclear magnetic resonance (NMR) method. A synthesis scheme of Step 1 is shown in (a-3).

[Chemical formula 54]

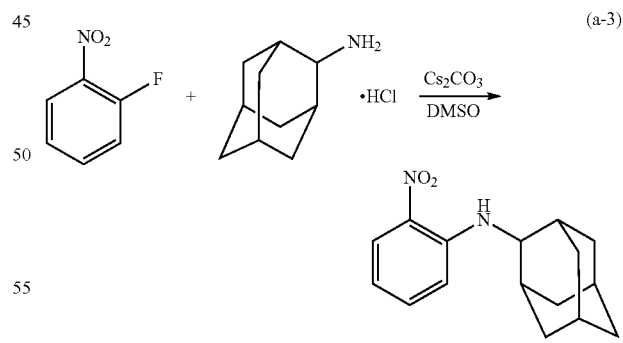

Step 2: Synthesis of N-(2-Adamantyl)-2-aminoaniline

In 1000-ml three-neck flask were put 7.9 g (29.1 mmol) of N-(2-adamantyl)-2-nitroaniline obtained in Step 1, 5.2 g (0.29 mol) of water, and 380 ml of ethanol, and the mixture was stirred. To this mixture was added 26.7 g (0.14 mol) of tin(II) chloride and the mixture was stirred under a nitrogen stream at 80° C. for 8 hours. After the stirring, this mixture was poured into 400 mL of a 2N aqueous solution of sodium hydroxide and the aqueous layer was subjected to extraction with chloroform. The obtained solution of the extract combined with the organic layer was washed with water and saturated brine, followed by drying with magnesium sulfate. The obtained mixture was subjected to gravity filtration, and the filtrate was concentrated to give a black oily substance. Hexane was added to this oily substance and irradiation with ultrasonic waves was performed. The precipitated solid was subjected to suction filtration to give 5.5 g of a brown solid in a yield of 78%. The obtained brown solid was identified as N-(2-adamantyl)-2-aminoaniline by a nuclear magnetic resonance (NMR) method. A synthesis scheme of Step 2 is shown in (b-3).

[Chemical formula 55]

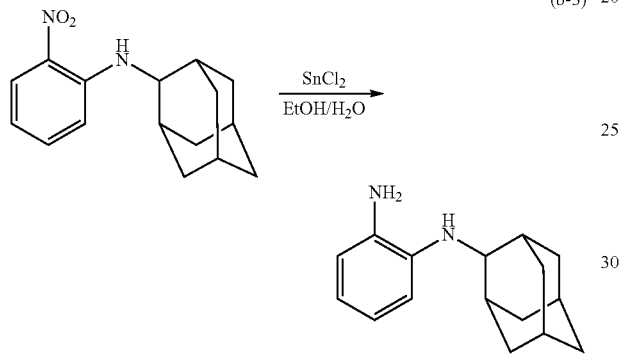

Step 3: Synthesis of N-[2-(2-Adamantylamino)phenyl]benzamide

In a 500-mL three-neck flask were put 5.5 g (22.6 mmol) of N-(2-adamantyl)-2-aminoaniline synthesized in Step 2, 3.4 g (33.9 mmol) of triethylamine, and 150 mL of tetrahydrofuran (THF), and the mixture was stirred. To this mixed solution, a mixed solution of 3.2 g (22.6 mmol) of benzoyl chloride and 25 mL of THF was added dropwise under cooling with ice, and the mixture was stirred at room temperature for 2 hours. After the stirring, the reacted solution was poured into 200 mL of water and the mixture was stirred for 30 minutes. After the stirring, chloroform was added and the organic layer and the aqueous layer were separated. The organic layer was washed with water, a saturated aqueous solution of sodium hydrogen carbonate, and saturated brine. After the washing, anhydrous magnesium sulfate was added to the organic layer for drying. The obtained mixture was subjected to gravity filtration, and the filtrate was concentrated to give a black oily substance. Hexane was added to this oily substance and irradiation with ultrasonic waves was performed. The precipitated solid was subjected to suction filtration to give 6.8 g of a white solid in a yield of 87%. The obtained white solid was identified as N-[2-(2-adamantylamino)phenyl]benzamide by a nuclear magnetic resonance (NMR) method. A synthesis scheme of Step 3 is shown in (c-3).

[Chemical formula 56]

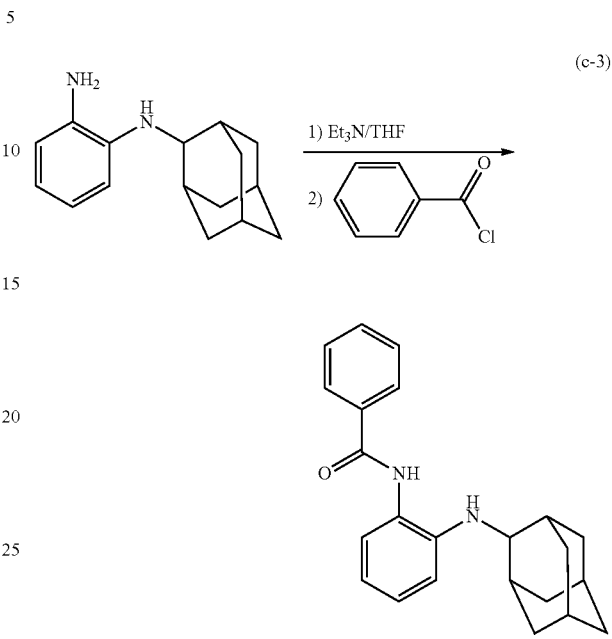

Step 4: Synthesis of 1-(2-Adamantyl)-2-phenyl-1H-benzimidazole (abbreviation: Hpbi-Adm2)

In a 500-ml three-neck flask equipped with a Dean-Stark tube were put 6.8 g (19.7 mmol) of N-[2-(2-adamantylamino)phenyl]benzamide synthesized in Step 3, 100 ml of xylene (dehydrated), and 0.375 g (1.97 mmol) of p-toluenesulfonic acid monohydrate, and the mixture was refluxed under a nitrogen stream at 150° C. for 6 hours. Because the reaction proceeded at a slow pace, the reaction temperature was changed to 170° C. and the mixture was refluxed for 18 hours. After the predetermined time elapsed, water was added to the reactant and the aqueous layer and the organic layer were separated. The aqueous layer was subjected to extraction with chloroform. The obtained solution of the extract combined with the organic layer was washed with water, a saturated aqueous solution of sodium hydrogen carbonate, and saturated brine, followed by drying with magnesium sulfate. This mixture was separated by gravity filtration, and the obtained filtrate was concentrated to give a yellow solid. The obtained solid was purified by silica column chromatography. A mixed solvent of toluene and ethyl acetate in a ratio of 7:1 was used as a developing solvent. The obtained fraction was concentrated to give a white solid. A mixed solvent of toluene and hexane was added to this solid, and suction filtration was carried out to give 1.1 g of a white solid in a yield of 17%. The obtained white solid was identified as 1-(2-adamantyl)-2-phenyl-1H-benzimidazole (abbreviation: Hpbi-Adm2) by a nuclear magnetic resonance (NMR) method. A synthesis scheme of Step 4 is shown in (d-3).

[Chemical formula 57]

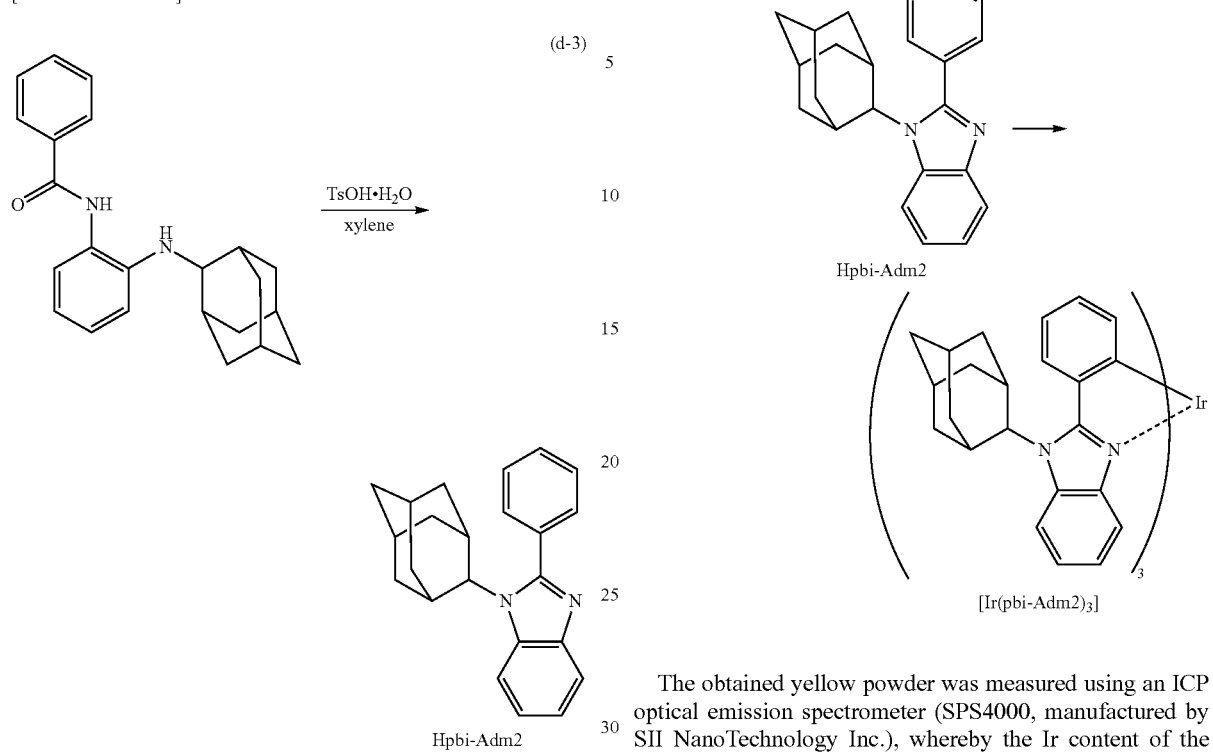

(d-3)

Step 5: Synthesis of Tris{2-[1-(2-adamantyl)-1H-benzimidazol-2-yl-κN3]phenyl-κC}iridium(III) (abbreviation: [Ir(pbi-Adm2)₃])

In a reaction container equipped with a three-way cock were put 1.9 g (5.8 mmol) of 1-(2-adamantyl)-2-phenyl-1H-benzimidazole and 0.569 g (1.16 mmol) of tris(acetylacetonato)iridium(III), and heating was performed at 250° C. for 43.5 hours. Dichloromethane was added to the obtained reaction mixture and irradiation with ultrasonic waves was performed. The precipitated solid was subjected to suction filtration to give a yellow solid. Methanol was added to this yellow solid and irradiation with ultrasonic waves was performed. Suction filtration was carried out to give a yellow solid. Further, the yellow solid was washed with water, methanol, hexane, and ethyl acetate in that order to give 0.62 g of a yellow powder in a yield of 46%. A synthesis scheme of Step 5 is shown in (e-3).

[Chemical formula 58]

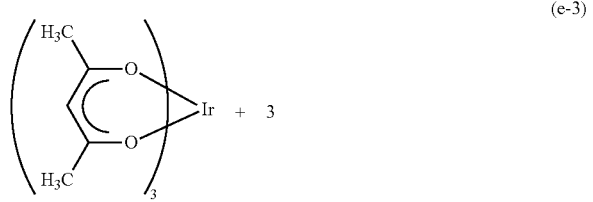

(e-3)

The obtained yellow powder was measured using an ICP optical emission spectrometer (SPS4000, manufactured by SII NanoTechnology Inc.), whereby the Ir content of the sample was found. The measurement data are shown below.

TABLE 2

| | Analytical Values | | (unit: weight %) |
|---|---|---|---|
| Element | n = 1 | n = 2 | Average |
| Ir | 16.4 | 16.5 | 16.5 |

Note:
1. An analytical value when the number of repetitions n was 1 and an analytical value when the number of repetitions n was 2 were obtained (the number of repetitions n means the number of times of pretreatment and then measurement were performed on samples).
2. The maximum number of significant digits of the analytical values is two, and the third digit is shown for reference.

Next, measurement by matrix-assisted laser desorption-ionization mass spectrometry (MALDI-MS) was performed in order to find the molecular weight of the sample. The measurement was performed in a positive mode. By MALDI-MS, an ion was detected at m/z 1174.4 in a mass spectrum. Because the mass number and isotope distribution were substantially consistent with a compositional formula ($C_{69}H_{69}IrN_6$) estimated by a calculation, it was presumed that the sample is a compound whose compositional formula is $C_{69}H_{69}IrN_6$. This presumption was consistent with the analysis result by ICP optical emission spectrometry. For this reason, it was confirmed that the sample is the objective substance.

Figure 19:
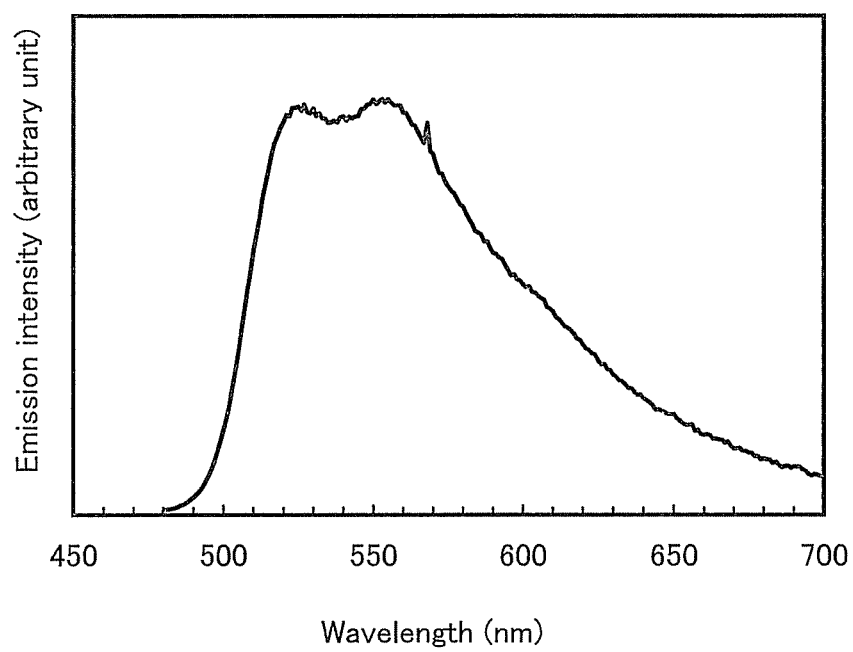
FIG. 19 shows an emission spectrum of a powder of [Ir(pbi-Adm2)$_3$], an iridium complex represented by Structural Formula (136).

Then, an emission spectrum of [Ir(pbi-Adm2)₃] was measured. The measurement of the emission spectrum was performed under the following conditions: a fluorescence spectrophotometer (FS920, manufactured by Hamamatsu Photonics K. K.) was used, a small amount of powder of [Ir(pbi-Adm2)₃] was put on a quartz glass, and the temperature was set to room temperature. FIG. 19 shows measurement results of the emission spectrum.

As shown in FIG. 19, [Ir(pbi-Adm2)₃], the iridium complex described in Embodiment 1, has emission peaks at 527 nm and 553 nm, and green light was observed from the powder.

Next, [Ir(pbi-Adm2)₃] obtained in this example was analyzed by liquid chromatography mass spectrometry (LC/MS).

The LC/MS analysis was carried out with Acquity UPLC (produced by Waters Corporation) and Xevo G2 T of MS (produced by Waters Corporation).

In the MS analysis, ionization was carried out by an electrospray ionization (ESI) method. At this time, the capillary voltage and the sample cone voltage were set to 3.0 kV and 30 V, respectively, and detection was performed in a positive mode. A component which underwent the ionization under the above-described conditions was collided with an argon gas in a collision cell to dissociate into product ions. Energy (collision energy) for the collision with argon was 70 eV. The mass range for the measurement was m/z=100 to 1200. The results are shown in FIGS. 20A and 20B.

Figure 20A:
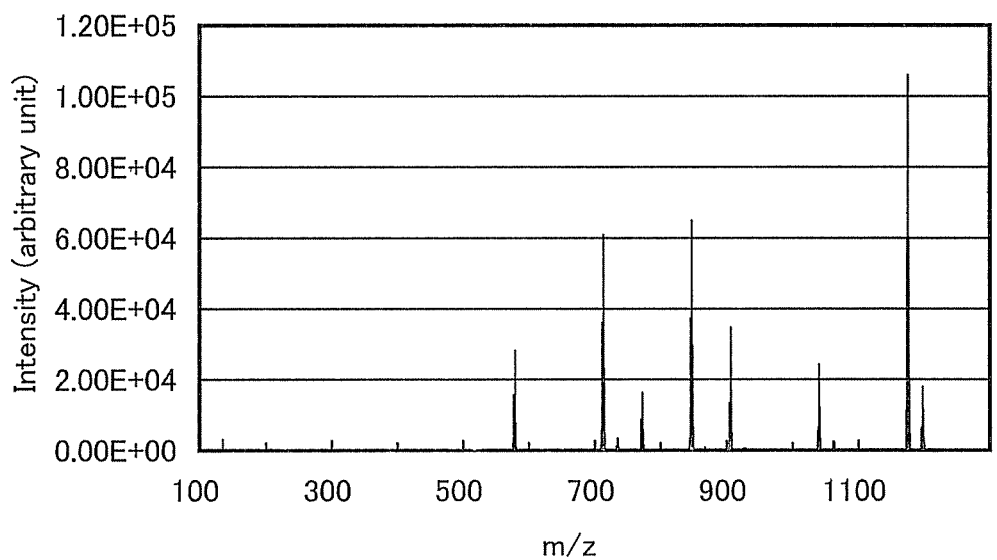
FIGS. 20A and 20B show LC/MS measurement results of [Ir(pbi-Adm2)$_3$], an iridium complex represented by Structural Formula (136).
Figure 20B:
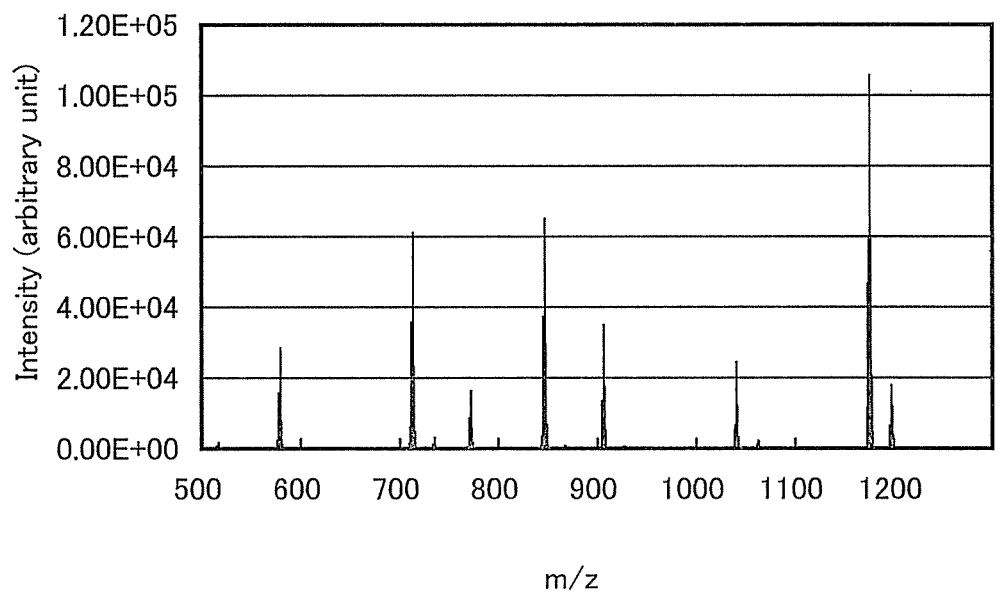

The results in FIGS. 20A and 20B show that product ions of [Ir(pbi-Adm2)₃], the organometallic complex that is one embodiment of the present invention represented by Structural Formula (136), were detected mainly around m/z 1040.41, m/z 906.30, m/z 847.33, m/z 772.19, m/z 713.22, and m/z 579.11.

It is presumed that the product ions around m/z 1040.41, m/z 906.30, and m/z 772.19 are respectively a cation in a state where one adamantyl group and a proton were eliminated from the compound represented by Structural Formula (136), a cation in a state where two adamantyl groups and a proton were eliminated therefrom, and a cation in a state where three adamantyl groups and a proton were eliminated therefrom, which suggests that [Ir(pbi-Adm2)₃], the organometallic complex that is one embodiment of the present invention, includes an adamantyl group. Further, it is presumed that the product ion around m/z 847.33 is a cation in a state where a proton and one Hpbi-Adm2 that is the ligand were eliminated from the compound represented by Structural Formula (136), which suggests that the compound includes Hpbi-Adm2 as a ligand. It is also presumed that the product ions around m/z 713.22 and m/z 579.11 are cations in a state where one ligand (Hpbi-Adm2), one or two adamantyl groups, and a proton were eliminated from the compound represented by Structural Formula (136), which suggests that [Ir(pbi-Adm2)₃], the organometallic complex that is one embodiment of the present invention, includes an adamantyl group.

Reference Example

A synthesis example of tris(5-methyl-3,4-diphenyl-4H-1,2,4-triazolato)iridium(III) (abbreviation: [Ir(Mptz)₃]), which was used for a material of the comparative light-emitting element 1, will be described.

Synthesis Example of [Ir(Mptz)₃]

Step 1: Synthesis of 3-Methyl-4,5-diphenyl-4H-1,2,4-triazole (abbreviation: HMptz)

In a round-bottom flask provided with a reflux pipe were put 5.04 g of thioacetanilide, 5.44 g of benzoylhydrazine, and 50 mL of 1-butanol, and the air in the flask was replaced with argon. This reaction container was subjected to irradiation with microwaves (2.45 GHz, 100 W) for 2 hours and 45 minutes to perform heating. Then, water was added to this solution and the organic layer was subjected to extraction with dichloromethane. The obtained organic layer was washed with water and dried with magnesium sulfate. After the drying, the solution was filtered. The solvent of this solution was distilled off, and the obtained residue was purified by silica gel column chromatography using ethyl acetate as a developing solvent, so that 3-methyl-4,5-diphenyl-4H-1,2,4-triazole (abbreviation: HMptz) was obtained (pale yellow powder, 18% yield). A synthesis scheme of Step 1 is shown below.

[Chemical formula 59]

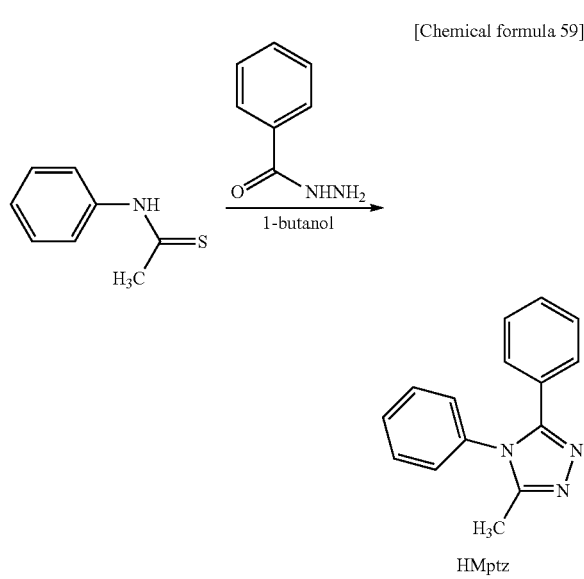

Step 2: Synthesis of Tris(5-methyl-3,4-diphenyl-4H-1,2,4-triazolato)iridium(III) (abbreviation: [Ir(Mptz)₃])

In a reaction container equipped with a three-way cock were put 1.40 g of the ligand HMptz, which was prepared in Step 1 above, and 0.58 g of tris(acetylacetonato)iridium(III), and the air in the reaction container was replaced with argon. Then, heating was performed at 250° C. for 17 hours and 30 minutes to cause a reaction. The reactant was dissolved in dichloromethane, and the solution was filtered. The solvent of the obtained filtrate was distilled off and purification was conducted by silica gel column chromatography using ethyl acetate as a developing solvent. Further, recrystallization was carried out with a mixed solvent of dichloromethane and hexane, so that the organometallic complex [Ir(Mptz)₃] was prepared (yellow powder, 22% yield). A synthesis scheme of Step 2 is shown below.

[Chemical formula 60]

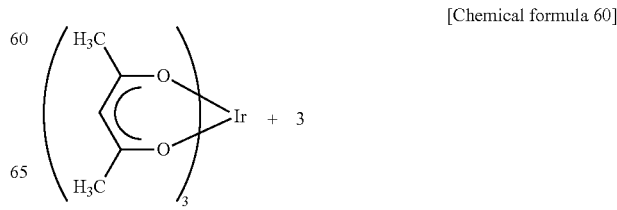

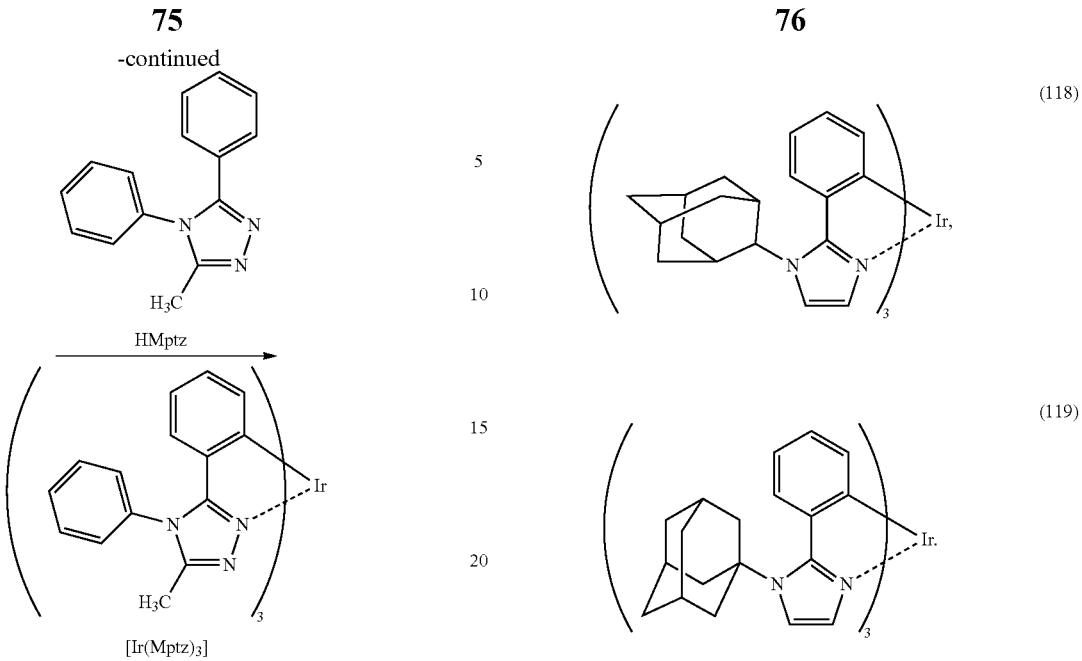

[Ir(Mptz)₃]

Analysis results by nuclear magnetic resonance (¹H-NMR) spectrometry of the yellow powder prepared in Step 2 described above are shown below. These results reveal that the organometallic complex [Ir(Mptz)₃] was obtained.

¹H NMR. δ(CDCl₃): 2.17 (s, 9H), 6.38 (d, 3H), 6.54 (t, 3H), 6.72 (dt, 3H), 6.87 (dd, 3H), 7.34 (m, 3H), 7.51 (brm, 3H), 7.57 (m, 9H).

This application is based on Japanese Patent Application serial no. 2011-282431 filed with Japan Patent Office on Dec. 23, 2011, the entire contents of which are hereby incorporated by reference.

What is claimed is:

1. An iridium complex represented by Formula (G5),

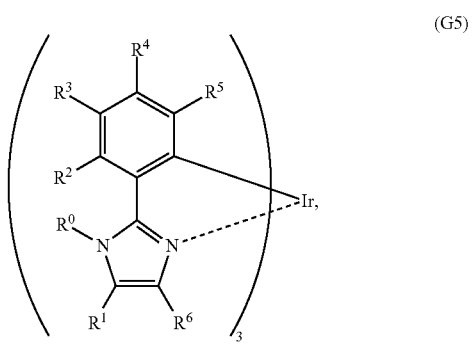

wherein $R^0$ represents a substituted or unsubstituted tricycloalkyl group having a bridge structure and having 9 or 10 carbon atoms, and
wherein $R^1$ to $R^6$ separately represent any one of hydrogen, a substituted or unsubstituted alkyl group having 1 to 6 carbon atoms, and an unsubstituted phenyl group.

2. The iridium complex according to claim 1, wherein $R^0$ represents an adamantyl group or a noradamantyl group.

3. The iridium complex according to claim 1, the iridium complex being represented by Formula (118) or Formula (119), 4. A light emitting-element comprising a light-emitting layer between a pair of electrodes,
wherein the light-emitting layer comprises the iridium complex according to claim 1.

5. A light-emitting device comprising the light-emitting element according to claim 4.

6. A lighting device comprising the light-emitting element according to claim 4.

7. An iridium complex represented by Formula (G6),

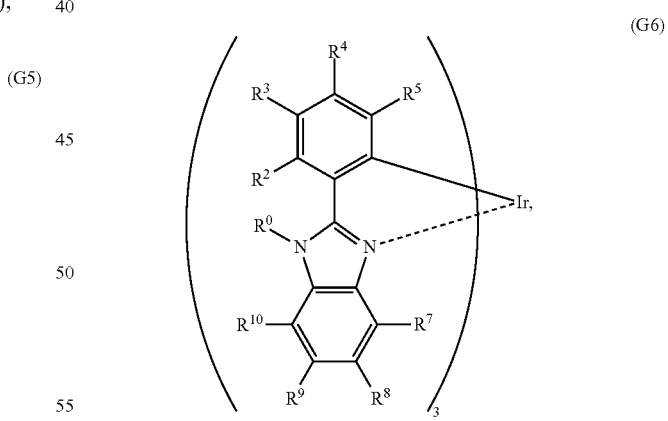

wherein $R^0$ represents a substituted or unsubstituted tricycloalkyl group having a bridge structure and having 9 or 10 carbon atoms, and
wherein $R^2$ to $R^5$ and $R^7$ to $R^{10}$ separately represent any one of hydrogen, a substituted or unsubstituted alkyl group having 1 to 6 carbon atoms, and a substituted or unsubstituted phenyl group.

8. The iridium complex according to claim 7, wherein $R^0$ represents an adamantyl group or a noradamantyl group.

9. The iridium complex according to claim 7, the iridium complex being represented by Formula (136) or Formula (137),

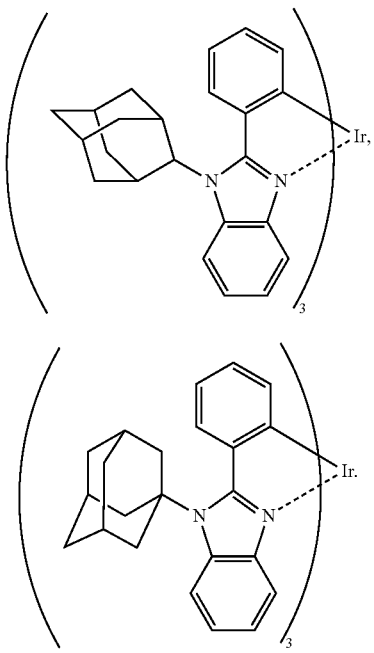

10. A light-emitting element comprising a light-emitting layer between a pair of electrodes,
wherein the light-emitting layer comprises the iridium complex according to claim 7.

11. A light-emitting device comprising the light-emitting element according to claim 10.

12. A lighting device comprising the light-emitting element according to claim 10.

13. An iridium complex represented by Formula (G1),

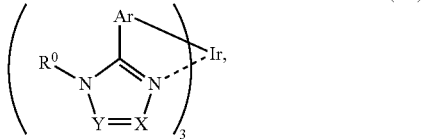

wherein Ar represents a substituted or unsubstituted arylene group having 6 to 12 carbon atoms,
wherein R⁰ represents a substituted or unsubstituted tricycloakyl group having a bridge structure and having 9 or 10 carbon atoms,
wherein X and Y separately represent nitrogen.

14. The iridium complex according to claim 13, wherein R⁰ represents an adamantyl group or a noradamantyl group.

15. The iridium complex according to claim 13, the iridium complex being represented by Formula (156),

16. A light-emitting element comprising element comprising a light-emitting layer between a pair of electrodes,
wherein the light-emitting layer comprises the iridium complex according to claim 13.

17. A light-emitting device comprising the light-emitting element according to claim 16.

18. A light device comprising the light-emitting element according to claim 16.

* * * * *

UNITED STATES PATENT AND TRADEMARK OFFICE
CERTIFICATE OF CORRECTION

| | | |
|---|---|---|
| PATENT NO. | : 9,768,396 B2 | Page 1 of 1 |
| APPLICATION NO. | : 13/722050 | |
| DATED | : September 19, 2017 | |
| INVENTOR(S) | : Hideko Inoue et al. | |

It is certified that error appears in the above-identified patent and that said Letters Patent is hereby corrected as shown below:

In the Claims

Column 78, Lines 12 to 13, Claim 13; Change "tricycloakyl" to --tricycloalkyl--.

Column 78, Line 32, Claim 16; Change "A light-emitting element comprising element" to --A light-emitting element--.

Column 78, Line 38, Claim 18; Change "A light device" to --A lighting device--.

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*